United States Patent
Penhasi et al.

(10) Patent No.: US 6,632,451 B2
(45) Date of Patent: *Oct. 14, 2003

(54) DELAYED TOTAL RELEASE TWO PULSE GASTROINTESTINAL DRUG DELIVERY SYSTEM

(75) Inventors: Adel Penhasi, Bat Yam (IL); Moshe Flashner, Petah Tikva (IL); E. Itzhak Lerner, Petah Tikva (IL)

(73) Assignee: Dexcel Pharma Technologies Ltd., Hadera (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/325,748

(22) Filed: Jun. 4, 1999

(65) Prior Publication Data

US 2002/0110593 A1 Aug. 15, 2002

(51) Int. Cl.[7] .................................................. A61K 9/02
(52) U.S. Cl. .................. 424/464; 424/465; 424/468; 424/471; 424/473; 424/474; 424/479; 424/482; 424/484; 424/489
(58) Field of Search ................................. 424/464, 465, 424/468, 471, 473, 474, 479–482, 484–489

(56) References Cited

U.S. PATENT DOCUMENTS 3,921,636 A 11/1975 Zaffaroni ..................... 128/260

(List continued on next page.)

FOREIGN PATENT DOCUMENTS

| CA | 2020802 | 1/1991 |
| EP | 077956 | 4/1983 |

(List continued on next page.)

OTHER PUBLICATIONS

Agyilirah, G.A. and G.S. Banker, "Polymers for Enteric Coating Applications," In: *Polymers for Controlled Drug Delivery*, Tarcha, P.J., ed., CRC Press, Inc., Boca Raton, F.L., publ., pp. 39–66 (1991).

(List continued on next page.)

*Primary Examiner*—Thurman K. Page
*Assistant Examiner*—Lakshmi S. Channavajjala
(74) *Attorney, Agent, or Firm*—D'vorah Graeser

(57) ABSTRACT

A two pulse gastrointestinal delivery system is provided. The system comprises a desired agent in combination with a swellable core material, the core being surrounded by an inner coat of a water-insoluble or relatively water-insoluble coating material in which particulate water-insoluble material is embedded. The inner coat is additionally surrounded by an outer coat that contains additional amounts of the desired agent. When the delivery device enters the gastrointestinal tract, the outer coat releases the desired agent contained therein and disintegrates, exposing the inner coat. The particulate matter in the inner coat takes up liquid, thus forming channels interconnecting the drug-containing core with the outside of the delivery device. Through these channels liquid enters the core which then swells to the point at which the inner coat is broken. When the integrity of the inner coat is destroyed, the core then disintegrates, immediately releasing all or most of the drug at a specific site. By controlling parameters in the device, such as the core material, carrier material in the coating, and particulate matter, the location of release of both pulses of the drug can be carefully controlled. The invention is also directed to a method of using the device for the treatment of disease by the release of drugs in the gastrointestinal tract in a location- and time-dependent manner.

36 Claims, 24 Drawing Sheets

U.S. PATENT DOCUMENTS

| | | | |
|---|---|---|---|
| 4,016,100 A | 4/1977 | Suzuki et al. | 252/316 |
| 4,107,288 A | 8/1978 | Oppenheim et al. | 424/22 |
| 4,138,362 A | 2/1979 | Vassiliades et al. | 252/316 |
| 4,169,804 A | 10/1979 | Yapel, Jr. | 252/62.53 |
| 4,169,885 A | 10/1979 | Raaf et al. | 424/16 |
| 4,252,786 A | 2/1981 | Weiss et al. | 424/19 |
| 4,277,364 A | 7/1981 | Shasha et al. | 252/316 |
| 4,279,812 A | 7/1981 | Cioca | 260/123.7 |
| 4,307,717 A | 12/1981 | Hymes et al. | 128/156 |
| 4,327,725 A | 5/1982 | Cortese et al. | 128/260 |
| 4,344,857 A | 8/1982 | Shasha et al. | 252/316 |
| 4,348,384 A | 9/1982 | Horikoshi et al. | 424/101 |
| 4,349,530 A | 9/1982 | Royer | 424/19 |
| 4,359,483 A | 11/1982 | Kaetsu et al. | 427/2 |
| 4,432,966 A | 2/1984 | Zeitoun et al. | 424/21 |
| 4,442,655 A | 4/1984 | Stroetmann | 53/428 |
| 4,492,684 A | 1/1985 | Goosen et al. | 424/19 |
| 4,568,536 A | 2/1986 | Kronenthal et al. | 424/22 |
| 4,569,837 A | 2/1986 | Suzuki et al. | 424/28 |
| 4,610,870 A | 9/1986 | Jain et al. | 424/19 |
| 4,619,913 A | 10/1986 | Luck et al. | 514/2 |
| 4,627,850 A | 12/1986 | Deters et al. | 604/892 |
| 4,675,381 A | 6/1987 | Bichon | 530/345 |
| 4,678,516 A | 7/1987 | Alderman et al. | 106/197.1 |
| 4,703,108 A | 10/1987 | Silver et al. | 530/356 |
| 4,794,002 A | 12/1988 | Henis et al. | 424/488 |
| 4,803,075 A | 2/1989 | Wallace et al. | 424/423 |
| 4,871,549 A | 10/1989 | Ueda et al. | 424/492 |
| 4,891,223 A | 1/1990 | Ambegaonkar et al. | 424/408 |
| 4,897,270 A | 1/1990 | Deutsch et al. | 424/465 |
| 4,904,474 A | 2/1990 | Theeuwes et al. | 424/424 |
| 5,162,117 A * | 11/1992 | Stupak et al. | 424/475 |
| 5,204,121 A | 4/1993 | Bücheler et al. | 424/495 |
| 5,229,131 A | 7/1993 | Amidon et al. | 424/451 |
| 5,260,068 A | 11/1993 | Chen | 424/451 |
| 5,260,069 A | 11/1993 | Chen | 424/451 |
| 5,401,774 A | 3/1995 | Pamukcu et al. | 514/569 |
| 5,422,121 A | 6/1995 | Lehmann et al. | 424/464 |
| 5,425,950 A * | 6/1995 | Dandiker et al. | 424/480 |
| 5,464,633 A | 11/1995 | Conte et al. | 424/480 |
| 5,472,708 A | 12/1995 | Chen | 424/451 |
| 5,498,608 A | 3/1996 | Johnson et al. | 514/150 |
| 5,508,040 A | 4/1996 | Chen | 424/451 |
| 5,514,663 A | 5/1996 | Mandel | 514/33 |
| 5,525,634 A | 6/1996 | Sintov et al. | 514/777 |
| 5,531,735 A | 7/1996 | Thompson | 604/891.1 |
| 5,593,697 A | 1/1997 | Barr et al. | 424/490 |
| 5,614,220 A | 3/1997 | Hirakawa et al. | 424/480 |
| 5,622,948 A | 4/1997 | Dunn et al. | 514/236.5 |
| 5,631,022 A | 5/1997 | Mandel et al. | 424/456 |
| 5,643,959 A | 7/1997 | Pamukcu et al. | 514/569 |
| 5,651,983 A | 7/1997 | Kelm et al. | 424/452 |
| 5,654,009 A | 8/1997 | Hata et al. | 424/490 |
| 5,656,290 A | 8/1997 | Kelm et al. | 424/456 |
| 5,679,638 A | 10/1997 | Teicher et al. | 514/6 |
| 5,686,105 A | 11/1997 | Kelm et al. | 424/452 |
| 5,686,106 A | 11/1997 | Kelm et al. | 424/463 |
| 5,686,589 A | 11/1997 | Brendel et al. | 536/20 |
| 5,688,776 A | 11/1997 | Bauer et al. | 514/54 |
| 5,780,055 A | 7/1998 | Habib et al. | 424/464 |
| 5,840,329 A | 11/1998 | Bai | 424/458 |
| 5,840,332 A * | 11/1998 | Lerner et al. | |
| 5,874,418 A | 2/1999 | Stella et al. | 514/58 |

FOREIGN PATENT DOCUMENTS

| | | |
|---|---|---|
| EP | 0 077 956 | 5/1983 |
| EP | 0 210 540 | 2/1987 |
| EP | 0 305 918 A1 | 3/1989 |
| EP | 0 250 374 | 5/1991 |
| EP | 0 485 157 A2 | 5/1992 |
| EP | 0 485 158 A2 | 5/1992 |
| EP | 0 485 171 A2 | 5/1992 |
| EP | 0 485 172 A2 | 5/1992 |
| EP | 0 485 173 A2 | 5/1992 |
| EP | 0 485 840 | 5/1992 |
| EP | 0 508 586 A1 | 10/1992 |
| EP | 0 572 942 | 12/1993 |
| EP | 0 576 675 | 1/1994 |
| EP | 0 612 520 | 8/1994 |
| EP | 0 671 167 A1 | 9/1995 |
| GB | 1085739 | 10/1967 |
| GB | 2 203 143 A | 10/1988 |
| WO | WO 92/16191 | 10/1992 |
| WO | WO 92/17165 | 10/1992 |
| WO | WO 93/09771 | 5/1993 |
| WO | WO 94/12160 | 6/1994 |
| WO | WO 94/28882 | 12/1994 |
| WO | WO 97/02020 | 1/1997 |
| WO | WO 97/03659 | 2/1997 |
| WO | WO 97/25979 | 7/1997 |
| WO | WO 98/51287 | 11/1998 |
| WO | WO 99/18938 | 4/1999 |

OTHER PUBLICATIONS

Andreasen, E., "Studies on the Thymolymphatic System," *Acta Pathol. Et Microbiol. Scand.* 49(*suppl.*):81–82 (1943).

Antonin, K.-H. et al., "Oxprenolol absorption in man after single bolus dosing into two segments of the colon compared with that after oral dosing," *Br. J. clin. Pharmac.* 19:137S–142S (1985).

Appel, L.E. et al., "Formulation and Optimization of a Modified Microporous Cellulose Acetate Latex Coating for Osmotic Pumps," *Pharms. Res.* 9(12):1664–1667 (1992).

Ashford, M. et al., "An in vitro investigation into the suitability of pH–dependent polymers for colonic targeting," *Intl. J. Pharma.* 91:241–245 (1993).

Banaker, U.V., "Drug Delivery Systems of the 90's, Innovations in Controlled Release," *Amer. Pharmacy NS27*(2):39–48 (1987).

Cárdenas, L. and J.D. Clements, "Oral Immunization Using Live Attenuated Salmonella spp. as Carriers of Foreign Antigens," *Clin. Microbiol. Rev.* 5(3):328–342 (1992).

Cargill, R. et al., "Controlled Gastric Emptying. 1. Effects of Physical Properties on Gastric Residence Times of Nondisintegrating Geometric Shapes in Beagle Dogs," *Pharma. Res.* 5(8):533–536 (1988).

Cargill, R. et al., "Controlled Gastric Emptying. II. In Vitro Erosion and Gastric Residence Times of an Erodible in Beagle Dogs," *Pham. Res.* 6(6):506–509 (1989).

Chien, Y.W., "Potential Developments and New Approaches in Oral Controlled–Release Drug Delivery Systems," *Drug Dev. & Indust. Pharm.* 9(7):1291–1330 (1983).

Cornes, J.S., "Part II The effect of age on Peyer's patches," *GUT* 6(3):230–233 (1965).

Cummings, J.H., "Progress report Laxative abuse," *GUT* 15:758–766 (1974).

Desai, S. and S. Bolton, "A Floating Controlled–Release Drug Delivery System: In Vitro–in Vivo Evaluation," *Pharma. Res.* 10(9):1321–1325 (1993).

Ermak, T.H. et al., "Strategies for Oral Immunization and Induction of Gastric Immunity," *Proceed. Intern. Symp. Control. Rel. Bioact. Mater.* 22:196–197 (1995).

Fairbairn, J.W., "The Active Constituents of the Vegetable Purgatives Containing Anthracene Derivatives," *J. Pharmacy & Pharmacol. 1(10)*:683–694 (1949).

Fara, J.W., "Colonic Drug Absorption and Metabolism," *Third International Conference on Drug Absorption*, Edinburgh (1988).

Forni, F. et al., "Papaverine hydrochloride release from ethyl cellulose–walled microcapsules," *J. Microencaps. 5(2)*:139–146 (1988).

Godbillon, J. et al., "Investigation of drug absorption from the gastronintestinal tract of man. III. metoprotol in the colon," *Br. J. clin. Pharmac. 19*:113S–118S (1985).

Gröning, R. and G. Heun, "Oral Dosage Forms with Controlled Gastrointestinal Transit," *Drug Dev. & Indust. Pharmacy 10(4)*:527–529 (1984).

Hardcastle, J.D. and J.L. Wilkins, "The action of sennosides and related compounds on human colon and rectum," *GUT 11*:1038–1042 (1970).

Ingani, H.M. et al., "Conception and in vivo investigation of peroral sustained release floating dosage forms with enhanced gastrointestinal transit," *Intl. J. Pharma. 35*:157–164 (1987).

Jimoh, A.G. et al., "Pulsatile Release of FSH for Superovulation in Cattle," *Theriogenology 43*:645–656 (1995).

Kenyon, C.J. et al., "The effect of food on the in vivo behaviour of enteric coated starch capusules," *Intl. J. Pharma. 112*:207–213 (1994).

Khan, A.K. et al., "An Experiment to Determine the Active Therapeutic Moiety of Sulphasalazine," *The Lancet 2*:892–895 (1977).

Klotz, U., "Clinical Phamacokinetics of Sulphasalazine, Its Metabolites and Other Prodrugs of 5–Aminosalicylic Acid," *Clin. Pharmacokinetics 10*:285–302 (1985).

Laakso, R. and S. Eerikäinen, "Effects of core components on indomethacine release from film–coated granules," *Intl. J. Pharma. 67*:79–88 (1991).

Levine, D.S. et al., "Coating of Oral Beclomethasone Dipropionate Capsules with Cellulose Acetate Phthalate Enhances Delivery of Topically Active Antiinflammatory Drug to the Terminal Ileum," *Gastroenterology 92(4)*:1037–1044 (1987).

Lin, S.Y. and J.W. Ayres, "Calcium Alginate Beads as Core Carriers of 5–Aminosalicylic Acid," *Pharma. Res. 9(9)*:1128–1131 (1992).

Lindholm, T. and M. Juslin, "Controlled Release Tablets," *Pharm. Ind. 44(9)*:937–941 (1982).

Longer, M.A. and J.R. Robinson, "Fundamental aspects of bioadhesion," *Pharmacy Intl. 7(5)*:114–117 (1986).

Mardini, H.A.L. et al., "Effect of polymer coating on faecal recovery of ingested 5–amino salicylic acid in patients with ulcerative colitis," *GUT 28*:1084–1089 (1987).

Mayersohn, M., "Principles of Drug Absorption," *In: Modern Pharmaceutics*, Banaker, G.S. and Rhodes, C.T., eds., Marcel Dekker, Inc., New York, publ., pp. 23–85 (1979).

McNeil, N.I. et al., "Mucosal surface pH of the large intestine of the rat and of normal and inflamed large intestine in man," *GUT 28*:707–713 (1987).

Morimoto, K. et al., "Enhancement of rectal absorptioin of insulin in polyacrylic acid aqueous gel bases containing long chain fatty acid in rats," *Intl. J. Pharma. 14*:149–157 (1983).

Park, K. and J.R. Robinson, "Bioadhesive polymers as platforms for oral–controlled drug delivery: method to study bioadhesion," *Intl. J. Pharma. 19*:107–127 (1984).

Rasmussen, S.N. et al., "5–Aminosalicylic Acid in a Slow––Release Preparation: Bioavailability, Plasma Level, and Excretioin in Humans," *Gastroenterolgy 83(5)*:1062–1070 (1982).

Ritschel, W.A. et al., "Biopharmazeutische Entwicklung und Beurteilung von magensaftresistent überzogenen Arzneiformen und solchen mit verlängerter Wirksamkeit," *In: Angewandte Biophamazie*, Wissenschaftliche Verlagsgesellschaft MBH, Stuggart, West Germany, publ., pp. 396–402 (1973).

Ritschel, W.A. and R. Udeshi, "Drug Release Mechanisms from Matrix and Barrier Coated Tablets Prepared with Acrylic Resin, with and without Addition of Channeling Agents," *Pharm. Ind. 49(7)*:734–739 (1987).

Ritschel, W.A., "Targeting in the Gastrointestinal Tract: New Approaches," *Meth. Find. Exp. Clin. Pharamcol. 13(5)*:313–336 (1991).

Rubinstein, A., "Microbially Controlled Drug Delivery to the Colon," *Biopharma. & Drug Disp. 11*:465–475 (1990).

Safwat, S.M., "Preparation and Characterization of Controlled–Release Tenoxicam Tablets," *Eur. J. Pharm. Biopharm. 40(5)*:321–326 (1994).

Sheth, P.R. and J. Tossounian, "The Hydrodynamically Balanced System (HBS™): A Novel Drug Delivery System for Oral Use," *Drug Dev. & Indust. Pharmacy 10(2)*:313–339 (1984).

Smart, J.D. et al., "An in–vitro investigation of mucosa–adhesive materials for use in controlled drug delivery," *J. Pharm. Pharmacol. 36*:295–299 (1984).

Stevens, C.E., "Physiological implications of microbial digestion in the large intestine of mammals: relation to dietary factors," *Am. J. Clin. Nutr. 31*:S161–S168 (1978).

Sun, Y.–M. et al., "Fluidized–bed spray coated porous hydrogel beads for substained release of diclofenac sodium," *J. Controlled Rel. 47*:247–260 (Sep. 1997).

Sutinen, R. et al., "Water–activated and pH–controlled release of weak bases from silicon reservoir devices," *Intl. J. Pharma. 62*:113–118 (1990).

U.S. Pharmacopeia XXII, National Formulary XVII, p. 1789 (1990).

U.S. Pharmacopeia XXII, National Formulary XVII, p. 1579 (1990).

Adkin, D.A. et al., "The Use of Scintigraphy to Provide "Proof of Concept" for Novel Polysaccharide Preparations Designed for Colonic Drug Delivery," *Pharm. Res. 14(1)*:103–107 (Jan. 1997).

Bedi, A. et al., "Inhibition of Apoptosis during Development of Colorectal Cancer," *Cancer Res. 55(9)*:1811–1816 (1995).

Bright, J.J. and A. Khar, "Apoptosis: Programmed Cell Death in Health and Disease," *Bioscience Reports 14(2)*:67–81 (1994).

Brogden, R.N. et al., "Sulindac: A Review of its Pharmacological Properties and Therapeutic Efficacy in Rheumatic Diseases," *Drugs 16(2)*:97–114 (1978).

Craven, P.A. and F.R. DeRubertis, "Effects of aspirin on 1,–2–dimethylhydrazine–induced colonic carcinogenesis," *Carcinogenesis 13(4)*:541–546 (1992).

Davis, S.S. et al., "Transit of pharmaceutical dosage forms through the small intestine," *GUT 27(8)*:886–892 (1986).

DiSario, J.A. et al., "Sulindac Induces Regression and Prevents Progression of Sporadic Colorectal Adenomas," *Gastroenterology 112(suppl)*:A555 (Apr. 1997).

DuBois, R.N. et al., "Nonsteroidal Anti–Inflammatory Drugs, Eicosanoids, and Colorectal Cancer Prevention," *Gastroenterology Clinics of North America* 25(4):773–791 (Dec. 1996).

Duggan, D.E. et al., "The disposition of sulindac," *Clin. Pharm. Therapeutics* 21():326–335 (1977).

Fenoglio, C.M. and R.R. Pacal, "Colorectal Adenomas and Cancer," *Cancer* 50(11):2601–2608 (1982).

Gazzaniga, A. et al., "Oral colon–specific drug delivery: design strategies," *S.T.P. Pharma Pratiques* 4(5):336–343 (1994).

Giardiello, F.M. et al., "Treatment of Colonic and Rectal Adenomas with Sulindac in Familial Adenomatous Polyposis," *New England J. Med.* 328(18):1313–1316 (1993).

Gowen, G., "Complete Regression of Villous Adenomas of the Colon Using Piroxicam, a Nonsteroidal Anti–Inflammatory Drug," *Dis. Colon Rectum* 39(1):101–102 (Jan. 1996).

Hanif, R. et al., "Effects of Nonsteroidal Anti–inflammatory Drugs on Proliferation and on Induction of Apoptosis in Colon Cancer Cells by a Prostaglandin–Independent Pathway," *Biochem. Pharm.* 52(2):237–245 (Jul. 1996).

Hixson, L.J. et al., "NSAID Effect on Sporadic Colon Polyps," *Am. J. Gastroenterology* 88(10):1652–1656 (1993).

Kelloff, G.J. et al., "Clinical development plan: sulindac," *J. Cell Biochem. Suppl* 20:240–251 (1994).

Kerr, J.F.R. et al., "Apoptosis: A Basic Biological Phenomenon with Wide–Ranging Impications in Tissue Kinetics," *Br. J. Cancer* 26(4):239–257 (1972).

Knutson, C.O. and M.H. Max, "Diagnostic and Therapeutica Colonoscopy," *Arch. Surg.* 114(4):430–435 (1979).

Konishi, F. and B.C. Morson, "Pathology of colorectal adenomas: a colonoscopic survey," *J. Clin. Path.* 35(8):830–841 (1982).

Labayle, D. et al., "Sulindac Causes Regression of Rectal Polyps in Familial Adenomatous Polyposis," *Gastroenterology* 101(3):635–639 (1991).

Ladenheim, J. et al., "Effect of Sulindac on Sporadic Colonic Polyps," *Gastroenterology* 108(4):1083–1087 (1995).

Lee, F.D., "Importance of apoptosis in the histopathology of drug related lesions in the large intestine," *J. Clin. Path.* 46(2):118–122 (1993).

Lee, S.H. et al., "Selective Expression of Mitogen–inducible Cyclooxygenase in Macrophages Stimulated with Lipopolysaccharide," *J. Biol. Chem.* 267(36):25934–25938 (1992).

Leserman, L.D. et al., "Cell–specific drug from liposomes bearing monoclonal antibodies," *Nature* 293(5829):226–228 (1981).

Lockshin, R.A. and C. M. Williams, "Programmed Cell Death–I. Cytology of Degeneration in the Intersegmental Muscles of the Pernyi Silkmoth," *J. Insect Physiol.* 11(2):123–133 (1965).

Logan, R.F.A. et al., "Effect of aspirin and non–steroidal anit–inflammatory drugs on colorectal adenomas: case–control study of subjects participating in the Nottingham faecal occult blood screening programme," *Br. Med. J.* 307(6899):285–289 (1993).

Masferrer, J.L. et al., "Endogenous glucocorticoids regulate an inducible cyclooxygenase enzyme," *Proc. Natl. Acad. Sci. USA* 89(9):3917–3921 (1992).

Maskens, A.P., "Histogenesis of Adenomatous Polyps in the Human Large Intestine," *Gastroenterology* 77(6):1245–1251 (1979 ).

Meade, E.A. et al., "Differential Inhibition of Prostaglandin Endoperoxide Synthase (Cyclooxygenase) Isozymes by Aspirin and Other Non–steroidal Anti–inflammatory Drugs," *J. Biol. Chem.* 268(9):6610–6614 (1993).

Mitchell, J.A. et al., "Selectivity of nonsteroidal antiinflammatory drugs as inhibitors of constitutive and inducible cyclooxygenase," *Proc. Natl. Acad. Sci. USA* 90(24):11693–11697 (1994).

Miyamoto, T. et al., "Purification of Prostaglandin Ensoperoxide Synthetase from Bovine Vesicular Gland Microsomes," *J. Biol. Chem.* 251(9):2629–2636 (1976).

Moorghen, M. et al., "A Protective Effect of Sulindac Against Chemically–Induced Primary Colonic Tumours in Mice," *J. Path.* 156(4):341–347 (1988).

Morson, B.C., "Evolution of Cancer of the Colon and Rectum," *Cancer* 34(3):845–849 (1974).

Nakada, I. et al., "Prednisolone therapy for intra–abdominal desmoid tumors in a patient with familial adenomatous polyposis," *J. Gastroenterology* 32(2):255–259 (Apr. 1997).

Neugut, A.I. et al., "The Effect of Calcium and Vitamin Supplements on the Incidence and Recurrence of Colorectal Adenomatous Polyps," *Cancer* 78(4):723–728 (Aug. 1996).

Northway, M.G. et al., "Piroxicam Decreases Postirradiation Colonic Neoplasia in the Rat," *Cancer* 66(11):2300–2305 (1990).

Oshima, M. et al., "Suppression of Intestinal Polyposis in $Apc^{\Delta 716}$ Knockout Mice by Inhibition of Cyclooxygenase 2 (COX–2)," *Cell* 87(5):803–809 (Nov. 1996).

Pasrichia, P.J. et al., "The Effects of Sulindac on Colorectal Proliferation and Apoptosis in Familial Adenomatous Polyposis," *Gastroenterology* 109(3):994–998 (1995).

Peleg, I.I. et al., "Aspirin and nonsteroidal Anti–inflammatory Drug Use and the Risk of Subsequent Colorectal Cancer," *Arch. Internal Med.* 154(4):394–399 (1994).

Piazza, G.A. et al., "Antineoplastic Drugs Sulindac Sulfide and Sulfone Inhibit Cell Growth by Inducing Apoptosis," *Cancer Res.* 55(14):3110–3116 (1995).

Piazza, G.A. et al. "Selective Apoptosis of Neoplastic Cells Accompanies Polyp Regression in Familial Adenomatous Polyposis (FAP) Patients Treated with FGN–1 (Sulidac Sulfone): Evidence for a Cyclooxygenase Independent Mechanism," *Gastroenterology* 112(4 Suppl):A638 (Apr. 1997).

Pritchard, D.M. and A.J.M. Watson, "Apoptosis and Gastrointestinal Pharmacology," *Pharmacol. Ther.* 72(2):149–169 (Nov. 1996).

Rao, C.V. et al., "Chemoprevention of Colon Carcinogenesis by Dietary Administration of Piroxicam, α–Difluoromethylornithine, 16α–Fluro–5–androsten–17–one, and Ellagic Acid Individually and in Combination," *Cancer Res.* 51(17):4528–4534 (1991).

Reddy, B.S. et al., "Dose–related Inhibition of Colon Carcinogenesis by Dietary Piroxicam, a Nonsteroidal Antiinflammatory Drug, during Different Stages of Rat Colon Tumor Development," *Cancer Res* 47(20):5340–5346 (1987).

Reddy, B.S. et al., "Chemoprevention of Colon Carcinogenesis by Concurrent Administration of Piroxicam, a Nonsteroidal Antiinflammatory Drug with D, L–α–Difluromethylornithine, an Ornithine Decarboxylase Inhibitor, in Diet," *Cancer Res.* 50(9):2562–2568 (1990).

Reddy, B.S. et al., "Inhibition of colon carcinogenesis by prostaglandin synthesis inhibitors and related compounds," *Carcinogenesis* 13(6):1019–1023 (1992).

Reddy, B.S. et al., "Inhibitory effect of aspirin n azoxymethane–induced colon carcinogenesis in F344 rats," *Carcinogenesis* 14(8):1493–1497 (1993).

Rex, D.K. et al., "Colonscopic Miss Rates of Adenomas Determined by Back–to–Back Colonscopies," *Gastroenterology* 112(1):24–28 (Jan. 1997).

Rex, D.K. et al., "Relative Sensitivity of Colonoscopy and Barium Enema for Detection of Colorectal Cancer in Clinical Practice," *Gastroenterology* 112(1):17–23 (Jan. 1997).

Riendeau, D. et al., "Comparison of the cyclooxygenase–1 inhibitory properties of nonsteroidal anti–inflammatry drugs (NSAIDS) and selective COX–2 inhibitors, using sensitive microsomal and platelet assays," *Can. J. Physiol. Pharmacol.* 75(9):1088–1095 (Sep. 1997).

Rosenberg, L. et al., "A Hypothesis: Nonsteroidal Anti–Inflammatory Drugs Reduce the Incidence of Large–Bowel Cancer," *J. Natl. Cancer Institute* 83(5):355–358 (1991).

Saffran, M. et al., "A New Approach to the Oral Administration of Insulin and Other Peptide Drugs," *Science* 233:1081–1084 (1986).

Savill, J., "Apoptosis in disease," *Eur. J. Clin. Invest.* 24(11):715–723 (1994).

Schatzkin, A. et al., "The Polyp Prevention Trial I: Rationale, Design, Recruitment, and Baseline Participant Characteristics," *Cancer Epidemiology, Biomarkers and Prevention* 5(5):375–383 (May 1996).

Shiff, S.J. et al., "Nonsteroidal Antiinflammatory Drugs Inhibit the Proliferation of Colon Adenocarcinoma Cells: Effects on Cell Cycle and Apoptosis," *Exper. Cell Res.* 222(1):179–188 (Jan. 1996).

Schottenfeld, D. and S.J. Winawer, "Large Intestine," in:*Cancer Epidemiology and Prevention*, Schottenfeld, J.D. and J.F. Fraumeni, eds., W.B. Saunders Company, Philadelphia, publ., pp. 703–727 (1982).

Schussheim, A. et al., "Sulindac–Induced Regression of Adenomatous Colonic Polyps in a Child with a History of Hepatoblastoma," *J. Pediatric Gastroenterology and Nutrition* 17(4):445–448 (1993).

Simmons, D.L. et al., "Identification of a phorbol ester–repressible v–src–inducible gene," *Proc. Natl. Acad. Sci. USA* 86(4):1178–1182 (1989).

Sinicrope, F.A. et al., "Spontaneous Apoptotic Indices in Human Colon Carcinomas," *Program of the Annual Meeting of the Am. Gastroenterological Association*:A657 (Apr. 1997).

Skinner, S.A. et al., "Sulindac Inhibits the Rate of Growth and Appearance of Colon Tumors in the Rat," *Arch. Surg.* 126(9):1094–1096 (1991).

Strong, H.A. et al., "Sulindac metabolism: The importance of an intact colon," *Clin. Pharm. Therapeutics* 38(4):387–393 (1985).

Suh, O. et al., "Aspirin Use, Cancer, and Polyps of the Large Bowel," *Cancer* 72(4);1171–1177 (1993).

Swanson, B.N. et al., "Sulindac disposition when given once and twice daily," *Clin. Pharm. Therapeutics* 32(3):397–403 (1982).

Taha, A.S. et al., "Famotidine for the Prevention of Gastric and Duodenal Ulcers Caused by Nonsteroidal Antiinflammatory Drugs," *New England J. Med.* 334(22):1435–1439 (May 1996).

Thompson, C.B., "Apoptosis in the Pathogenesis and Treatment of Disease," *Science* 267:1456–1462 (1995).

Thun, M.J. et al., "Aspirin Use and Reduced Risk of Fatal Colon Cancer," *New England J. Med.* 325(23):1593–1596 (1991).

Tsujii, M. and R.N. DuBois, "Alterations in Cellular Adhesion and Apoptosis in Epithelial Cells Overexpressing Prostaglandin Endoperoxide Synthase 2," *Cell* 83(3):493–501 (1995).

Tsukada, K. et al., "Noncytotoxic Drug Therapy for Intra–Abdominal Desmoid Tumor in Patients with Familial Adenomatous Polyposis," *Dis. Colon Rectum* 35(1):29–33 (1992).

Vane, J.R. and R.M. Botting, "New insights into the mode of action of anti–inflammatory drugs," *Inflam. Res.* 44(1):1–10 (1995).

Waddell, W.R. et al., "Nonsteroid Antiinflammatory Drugs and Tamoxifen for Desmoid Tumors and Carcinoma of the Stomach," *J. Surg. Oncol.* 22(3):197–211 (1983).

Waddell, W.R. et al., "Sulindac for Polyposis of the Colon," *Am. J. Surg.* 157(1):175–179 (1989).

Winawer, S.J. et al., "Colorectal Cancer Screening: Clinical Guideline and Rationale," *Gastroenterology* 112(2):594–642 (Feb. 1997).

English Language abstract of WO 97/03659, Derwent World Patents Index (Dialog File 351), WPI Accession No. 97–145197.

Kwan, K.C. and D.E. Duggan, "Pharmacokinetics of Sulindac," *Acta Rhum. Belgica* 1:168–178 (1977).

Rankin, G.B., "Indications, Contraindications, and Complications of Colonoscopy," in: *Gastroenterologic Endoscopy*, Sivak, M.V., ed., W.B. Saunders Co., Philadelphia, publ., pp. 868–880 (1987).

European Search Report for International application No. PCT/US 98/20779, mailed on Jan. 19, 1999.

Bigard, M.A. et al., "One–week triple therapy using omeprazole, amoxycillin and clarithromycin for the eradication of *Helicobacter pylori* in patients with non–ulcer dyspepsia: influence of dosage of omeprazole and clarithromycin," *Ailment Pharmacol. Ther.* 12:383–388 (Apr. 1998).

Boschi, S. et al., "Bioavailability of a New Formulation of the Association Sulfamethoxazole–Trimethorprim," *Int. J. Clin. Pharm. Res.* 1(13):175–181 (Jul. 1981).

Conte, U. et al., "ibuprofen Delayed Release Dosage Forms: A Proposal for the Preparation of an In Vitro/In Vivo Pulsatile System," *Eur. J. Pharm. Biopharm.* 38(6):209–212 (Dec. 1992).

Conte, U. and L. Maggi, "Geomatrix® Tablets fo rthe Pulsatile Release of Drugs," *Proceed. Int'l Symp. Control. Rel. Bioact. Mater.* 24:291–292 (1997).

Gazzaniga, A. et al., "Chronotopic® Drug Delivery Systems For Time (*Delayed–Pulsatile*) And/Or Site Specific Release, "0 *Proceed. Intern. Symp. Control. Rel. Bioact. Mater.* 21:744–745 (1994).

Gupta, S.K. et al., "Multiple–Dose Pharmacokinetics and Pharmacodynamics of OROS and Immediate–Release Amitriptyline Hydrochloride Formulations," *J. Clin. Pharmacol.* 38:60–67 (Jan. 1998).

Hessemer, V. et al., "Influence of the Vasodilator Drug Isosorbide Dinitrate on Ocular Circulation," *Arch. Opthalmol.* 115:324–327 (Mar. 1997).

Ishino, R. et al., "Design and Preparation of Pulsatile Release Tablet as a New Oral Drug Delivery System," *Chem. Pharm. Bull.* 40(11):3036–3041 (Nov. 1992).

Ishino, R. et al., "Absorption of Diltiazem in Beagle Dog from Pulsatile Release Tablet," *Chem. Pharm. Bull.* 40(11):3094–3096 (Nov. 1992).

Koëter, G.H. et al., "Pharmacokinetics of Sustained Release Theorphylline in Low and High Multidose Regimens," *Br. J. clin. Pharmac.* 12:647–651 (Nov. 1981).

Krögel, I. and R. Bodmeier, "Pulsatile Drug Release form an Insoluble Capsule Body Controlled by an Erodible Plug," *Pharmaceut. Res.* 15(3):474–481 (Mar. 1998).

Lin, S.–Y. et al., "Theophylline Bioavailability After Single Oral Administration of Sustained–Release Microcapusles," *Curr. Therapeut. Res.* 42(4):564–573 (Oct. 1987).

Lippold, B.C. and J.E. Möckel, "Pulsatile Release from Laminated Methylhydroxy–propyl Cellulose Matrices with KCL as Model Drug," *Acta Pharm. Technol.* 36(2):97–98 (1990).

Munday, D.L., "Bimodal in vitro release from polymeric matrix tablets containing centralised drug cores," *S.T.P. Pharma Sci.* 6(3):182–187 (May–Jun. 1996).

Otsuka, M. and Y. Matsuda, "Controlled Drug Release of Highly Water–Soluble Pentoxifylline from Time–Limit Disintegration–Type Wax Matrix Tablets," *Pharmaceut. Res.* 11(3):351–354 (Mar. 1994).

Robert, D. et al., "Epilim® Chrono: A Multidose, Crossover Comparison of Two Formulatons of Valproate in Healthy Volunteers," *Biopharmaceut. & Drug Dispos.* 17(2):175–182 (Mar. 1996).

Rohatagi, S. et al., "Pharmacokinetic Evaluation of a Selegiline Pulsatile Oral Delivery System," *Biophamaceut. & Drug Dispos.* 18(8):665–680 (Nov. 1997).

Sarna, S.K, "Physiology and Pathophysiology of Colonic Motor Activity," *Digestive Dis. Sci.* 36(6):827–862 (Jun. 1991).

Sarna, S.K., "Physiology and Pathophysiology of Colonic Motor Activity," *Digestive Dis. Sci.* 36(7):998–1018 (Jul. 1991).

Schwartz, J. et al., "Impact of Ciprofloxacin on Theophylline Clearance and Steady–State Concentrations in Serum," *Antimicrobial Agents Chemother.* 32(1):75–77 (Jan. 1988).

Stevens, R.E. et al., "Controlled, Multidose, Pharmacokinetic Evaluation of two Extended–Release Carbamazepine Formulations (Carbatrol and Tegretol–XR)," *J. Pharmaceut. Sci.* 87(12):1531–1534 (Dec. 1998).

Warren, R.J. et al., "Pharmaceutical Applications of Internal Reflectance Spectroscopy," *Microchem. J.* 12(4):555–567 (Dec. 1967).

* cited by examiner

DELAYED TOTAL RELEASE TWO PULSE GASTROINTESTINAL DRUG DELIVERY SYSTEM

FIELD OF THE INVENTION

The invention is in the field of drug delivery. Specifically, the invention is directed to a drug delivery system that provides enterally-administered pharmaceuticals in a two pulse fashion.

BACKGROUND OF THE INVENTION

The ability to deliver a drug in a manner that targets the drug for absorption at a specific region of the gastrointestinal tract is desirable for many reasons. Such a delivery system would allow the medical practitioner to locally treat gastrointestinal diseases. Local treatment of gastrointestinal diseases would avoid systemic side effects of drugs or inconvenient and painful direct delivery of drugs. In addition, such a delivery system could potentially increase the efficiency of a drug, thus allowing a reduction of the minimum effective dose of the drug. A delivery system that could target a drug to a specific region of the gastrointestinal tract would thus be useful for the treatment of a wide variety of diseases and conditions.

WO 97/25979 describes a drug-delivery device for the targeting of various parts of the gastrointestinal tract. A core containing a drug is coated with a hydrophobic polymer which contains hydrophilic, non-water-soluble particles embedded therein. These particles serve as channels for aqueous medium entering the core and for the release of drugs by diffusion through these channels. This delivery system can target various parts of the gastrointestinal tract and slowly release its drug load.

U.S. Pat. No. 5,525,634 describes a delivery device that contains a drug in combination with a matrix. The matrix contains a saccharide-containing polymer. The matrix-drug combination can be coated or uncoated. The polymer is resistant to chemical and enzymatic degradation in the stomach and susceptible to enzymatic degradation in the colon by colonic bacteria.

EP 485,840 (Röhm GmbH), discloses a gastrointestinal delivery device containing, as a coating, a mixture of a polysaccharide and Eudragit®™. However, this formulation does not allow control of the rate of liquid entry into the formulation. Therefore, control of the site of release of the drug cannot be achieved. Further, the polysaccharide is not provided in particulate form.

U.S. Pat. No. 4,627,850 (Deters et al.) discloses an osmotic capsule for the controlled rate delivery of a drug comprising outer and inner walls each formed of a different polymeric material, the inner wall defining a space containing the drug, with a passageway through the walls connecting the exterior of the outer wall with the interior of the inner wall.

U.S. Pat. No. 4,904,474 (Theuwes et al.) discloses a colonic drug delivery device comprising means for delaying the delivery in the drug and in the small intestine and means for delivering the drug in the colon. This device comprises osmotic means for forcing the active pharmaceutical agent out from the compartment in which it is contained through an exit provided in said compartment, into the colon. The means for delaying delivery in the stomach or in the small intestine are pH-resistant coatings. The delay in delivery of the drug is time-based.

U.S. Pat. No. 5,593,697 describes a pharmaceutical implant containing a biologically active material, an excipient comprised of at least one water soluble material and at least one water insoluble material, and a polymer film coating adapted to rupture at a predetermined period of time after implantation.

U.S. Pat. No. 4,252,786 describes a controlled release tablet for the administration of medicinal agents over a prolonged period of time.

U.S. Pat. Nos. 5,260,069 and 5,472,708 describe a dosage form for delivering drugs, and particularly drugs that cannot be released by diffusion through a porous coating, such as water insoluble drugs.

U.S. Pat. No. 4,897,270 describes a pharmaceutical tablet comprising a tablet core and a film coat to mask the taste of the core. The core disintegrates immediately following rupture of the film coat.

U.S. Pat. No. 5,204,121 describes a drug release system in pellet form where the pellets consist of a core containing the active compound. The core is surrounded by a polymer-containing jacket and a undigestible lacquer layer that is permeable to water. The outer lacquer layer does not dissolve but is said to carry water to the migration controlling jacket layer which then brings the liquid in contact with the drug containing core.

U.S. Pat. No. 4,891,223 describes compositions for the sustained release of a pharmaceutical, comprising a drug-containing core, a first coating containing a polymer swellable upon penetration of the surrounding media, and a second coating, enveloping the first coating, comprising a polymer that is water-soluble and that forms a semi-permeable barrier. The outer coating is said to permit diffusion of the media, into the first coating and then diffusion of the dissolved drug into the surrounding media. The second coating must have requisite stretchability to prevent rupture of a second coating due the swelling of the first coating until a specific time in the release pattern.

U.S. Pat. No. 4,327,725 describes a variation of a basic osmotic device for drug release. The structure of the device is an active agent enclosed in a hydrogel layer that is enclosed in a semi-permeable membrane. The semi-permeable membrane allows diffusion of external fluid but does not allow diffusion of the solution of active agent to the surrounding environment. The hydrogel swells with absorption of external fluid and exerts pressure on the solution of active agent in the external fluid. The solution of the active agent in the external fluid is then delivered to the surrounding media through a single specially constructed passageway through the hydrogel layer and the membrane.

Some pulsatile delivery systems exist in the art. U.S. Pat. No. 5,162,117 describes a two pulse tablet of flutamide for the treatment of prostate cancer. The first pulse is contained in an immediate release layer while the second pulse is obtained from a core which contains a solid dispersion of the flutamide in a carrier. The pulses are separated by a film layer of an enteric coating at 4–15% weight percent of the core. The enteric coating slowly dissolves after the delivery of the first pulse of drug allowing the release of the second pulse. Enteric coatings as a delaying layer suffer from disadvantages of lack of parameters to control the precise timing of the delivery of the second pulse and are limited to delivering the second pulse to the small intestine. The slightly acidic environment of the human colon can cause the enteric coating to stop dissolving upon colon entry and may cause the second dose to be undelivered if the delay time between the pulses is longer than the time of transit through the small intestine. This disadvantage would be magnified if the first dose were to be limited to delivery to the small intestine and not to the stomach in which case the delay to the second pulse would be limited to about 3–4 hours.

U.S. Pat. No. 5,260,069 describes a capsule which contains a plurality of pellets with varying delay times to drug release. By mixing pellets of different delay times one can obtain pulsatile delivery of the drug. The delay time to drug delivery of the pellets is controlled by the pellets containing a swelling agent and the drug and being surrounded by a membrane that contains a water insoluble film and a water soluble film. The water soluble component of the film dissolves slowly thereby weakening the membrane. Water entry into the pellets causes them to swell and burst the weakened membrane. U.S. Pat. No. 5,260,068 describes a unit dosage form that contains populations of pellets or particles that have different delay times to drug delivery. The drug is contained in the pellet along with an osmotic agent. The pellets are coated with a water permeable, water-insoluble film that allows water diffusion into the pellet. The osmotic agent dissolves in the water causing the pellet to swell and eventually burst to release drug. Differences in the water permeability of the film coating afford the differences in delay time.

These systems suffer from the disadvantage of not being able to control the water entry into the system, and not having a variable parameter that can provide such control. These systems suffer from a further disadvantage in that the pellets naturally spread as they travel through the GI tract. This makes the delivery of the dose less site specific and therefore less efficacious.

WO 98/51287 describes a pulsatile system based on multiple particles in a dosage form. The drug release from the particle is controlled by combinations of controlled release layers, swelling layers and coating layers. The controlled release layer is a slightly crosslinked poly(acrylic acid) polymer of high molecular weight admixed with a water soluble polymer. This system too suffers from the disadvantage of not having many parameters for tailoring the rate of water entry into the pellets. The system suffers from a further disadvantage of the natural spread of the pellets as they travel through the GI tract making the delivery of the dose less site specific and therefore less efficacious.

Lippold, B. C. and Moekel, J. E. (*Acta Pharm. Technol.* 36(2):97–98 (1990)) describe a two pulse tablet system consisting of a triple laminate of hydroxypropylmethylcellulose (HPMC) prepared by successive direct compressions. The drug was contained in the inner core and the outer layer with a drug free layer separating the two drug containing layers. The thickness of the drug free layer controlled the time between doses within the range of 2.5 to 6.5 hours. This system is based on erosion of the spacer layer and offers less control over time of drug delivery than other systems, Furthermore, the lag time attainable is limited.

Ishino R. et. al. (*Chem. Pharm. Bull.* 40(11):3036–3041 (1992)) describe a single pulse tablet based on the dry pressing of a partially water permeable layer onto a swellable core which contains drug. The outer shell consisted of hydrogenated castor oil and polyethylene glycol 6000 and could control lag time by changing the thickness or the relative composition of the pressed outer layer.

Conte, U. et. al., (*Eur. J. Pharm. Biopharm.*, 38(6): 209–212 (1992)) describe a two pulse tablet for ibuprofen which consists of three layers. The inner core which contains drug is overlaid with a gelling barrier of hydroxypropylmethylcellulose which is drug free. The outer layer contains a drug. Different molecular weights and/or viscosities of the HPMC control the rate of penetration of water through the gelling layer and the rate of erosion of the gelling layer thereby controlling the lag time between pulses. This system is based on erosion of the spacer layer or permeation of the water through the gel layer and offers less control over time of drug delivery than other systems. Furthermore, the lag time attainable is limited.

Otsuka, M. and Matsuda, Y. (*Pharm. Res.* 11(3):351–354 (1994)) describe a pulse tablet based on a dry coat. The first pulse is delivered by a dry coated outer layer that is pressed on a disintegrating wax matrix core. The core delivers the second pulse. This system does not offer many parameters for controlling the lag time between pulses.

Munday, D. L. (*S. T. P. Pharma Sci.* 6(3):182–7 (1996)) describes a matrix tablet capable of a bimodal release pattern. Core tablets containing theophylline are pressed in a matrix containing HPMC, lactose and theophylline. The rates of release from each component can be controlled and a bimodal pattern of release can be obtained. There is no teaching as to separating pulses of the drug delivery by controlled amounts of lag time.

WO 99/18938 describes an immediate release gastrointestinal drug delivery system. This system is composed of a drug-containing core that is surrounded by a hydrophobic polymer material into which hydrophilic particulates are embedded. Upon exposure to the gastrointestinal environment, the insoluble hydrophilic particles swell. As a result of this swelling, channels form that serve as conduits for the controlled entry of liquid into the core. The core then swells or otherwise imparts pressure on the coat. At a predetermined time, the coat bursts and the drug is released from the core.

Thus, there is a need for a drug delivery system that provides more than one pulse of a drug, that would allow strict control over the lag time between pulses of the drug, be controllable within wide ranges of lag times and thereby allow the temporal and spatial separation of doses of the same drug or of two different drugs wherever high concentration of a drug for a relatively short period of time is desired. Such a system could improve patient compliance to a drug regimen or offer opportunities of treatment otherwise not attainable.

SUMMARY OF THE INVENTION

Recognizing the problems with current methods for delivering efficacious levels of multiple drugs to specific regions of the gastrointestinal tract, and cognizant of the need for drug delivery systems that facilitate patient compliance, the inventors investigated alternate mechanisms for the administration of desired agents to the gastrointestinal tract. These efforts have culminated with the characterization of a unique double pulse drug delivery system that is not only capable of providing one or more desired agents in a desired temporal and spatial manner to specific areas of the gastrointestinal tract, but is also capable of delivering highly concentrated pulses of such agents.

Thus, in a first embodiment, the invention is directed to a double pulse delivery system or device for targeted delivery to one or more specific locations in the gastrointestinal tract or alimentary canal. The double pulse delivery device contains a core material that is encapsulated by an inner coat, which is, in turn encapsulated by outer coat. A third coat, such as an enteric coat or a coat to mask taste or to ease swallowing, is optionally present. The desired agents are incorporated into the outer coat and core. The agent in the outer coat is released in a burst (i.e. immediate) or in a sustained release fashion, as desired. Release of the agent from the outer coat activates a series of steps that results in a bursting of the core, and, as a result, release of the agent contained therein. The release of the desired agent from the outer coat and the release of the desired agent from the core can be adjusted as desired to achieve a predetermined temporal and spatial release of the agents in the patient's gastrointestinal tract.

In a further embodiment, the invention is directed to a method of treating a patient in need of the same by administering the double pulse delivery system or device as above to the patient.

In a further embodiment, the invention is directed to a method of preparing a double pulse delivery system.

DETAILED DESCRIPTION OF THE PREFERRED EMBODIMENTS

Definitions

Figure 1:
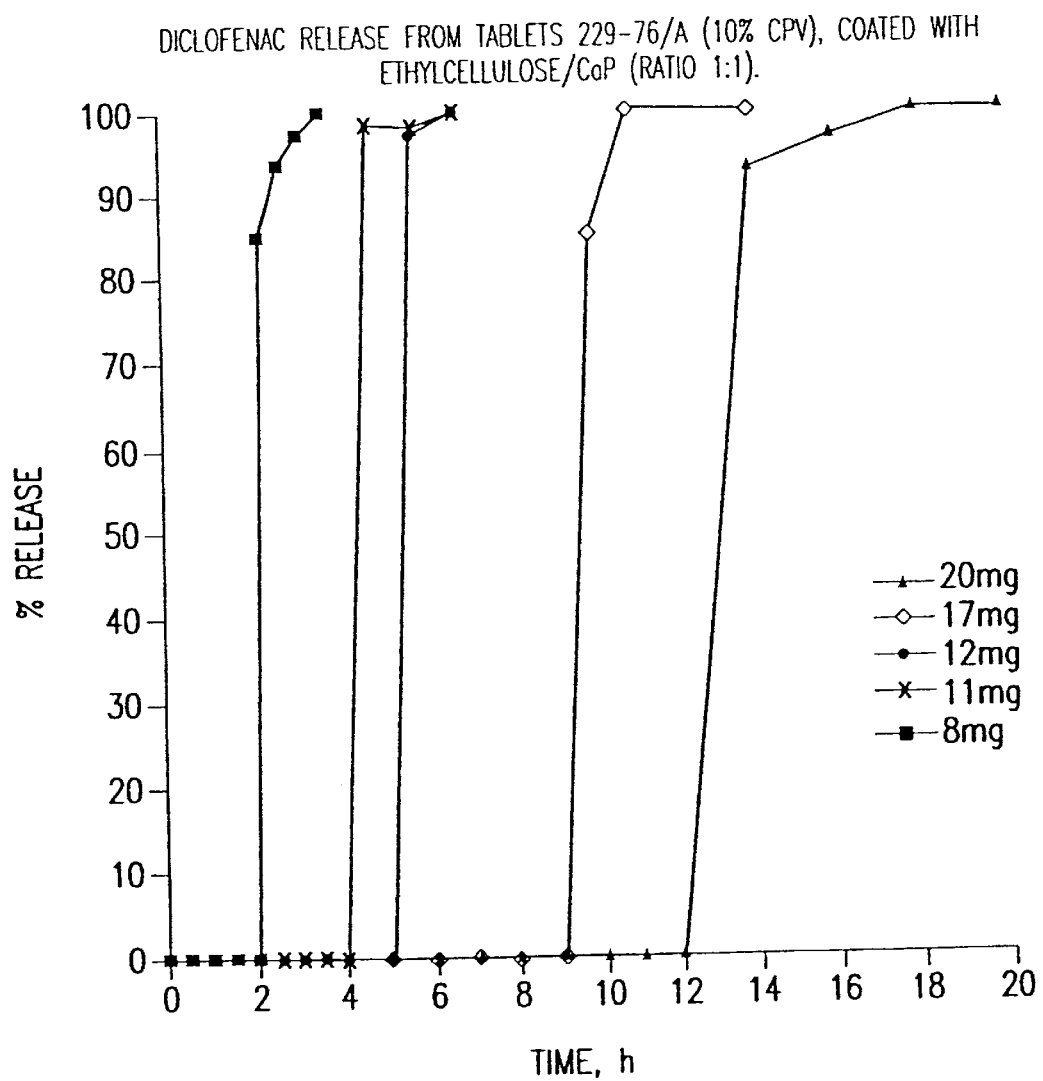
FIG. 1. Diclofenac release from tablets 229-76/A (10% CPV), coated with ethylcellulose/CaP (ratio 1:1).

In the description that follows, a number of terms used in pharmacology are extensively utilized in order to provide a clear and consistent understanding of the specification and claims, and the scope to be given such terms, the following definitions are provided. Where not specifically indicated, the terms used herein are used according to their normal and/or art-recognized meaning.

For example, the terms "colon," "large intestine," "small intestine," "stomach," "rectum" and "ileum" are all used according to their art-recognized meanings.

By "coat" is intended a layer that covers something else. Therefore, a formulation that is described as a "coated" core is one in which a core material is surrounded by, and thus covered by, a defined, separate layer that constitutes the "coat." In the context of the invention, "coat," "coating," "film," "layer," "covering," and the like are interchangeable.

By "press coat" is intended a coat that is applied by surrounding a core with a powder, mixture of powders, or a granulate and using pressure to form the coat.

By "spray coat" is intended a coat that is formed by spraying a solution or a suspension of the material to be coated onto the core. The coat is formed by drying the solution or the suspension on the core material.

By delivering a desired agent, for example, a drug, as a "pulse" is intended a delivery method that provides a brief, sudden increase in an otherwise constant amount of the agent to a patient in need of the same. Thus, a "pulse" of a desired agent results in a brief, sudden release of a desired amount of an agent from a delivery system such that as a result of this release, there is a rapid increase in the concentration of the agent at the desired site in the patient. Such increase is over and above whatever level of the agent had been previously present, if any, prior to the "pulse." The increase is not sustained in a prolonged fashion unless repeated pulses are provided. Preferably, the pulse is the result of an immediate release or a short sustained release of the drug.

By delivering a desired agent such as a drug in a "pulsating" manner is intended the delivery of a drug in a manner that provides more than one, that is, repeated sudden releases of desired concentrations of the drug, so that repeated rapid increases in drug concentrations can be detected that are over and above whatever level of the drug had been present, if any, immediately prior to each release.

By a coating being "burst" open is intended that the coating comes open or flies apart suddenly, as from internal pressure, in a manner that breaks, shatters, or explodes the integrity of the coating, thus exposing anything the coating had previous surrounded to the local environment.

By the term "immediate" release or delivery is intended the delivery of a desired agent in a manner that is the result of a burst in which the structure containing such agent releases all or essentially all the agent at the same time.

By the term "short sustained" release or delivery is intended the delivery of a desired agent in a manner in which the structure containing such agent does not releases all or essentially all the agent at the same time, nor over a "prolonged" period of time, but rather releases the agent over a relatively short period of time, for example, less than five hours.

By the term "prolonged" release or delivery is intended the delivery of a desired agent in a manner in which the structure containing such agent releases all or essentially all of the agent, for example, for a period of time that is five hours or longer.

By a "lag time" or "delay time" is intended a time period between two events. For example, by a lag time between two pulses of release of a desired agent is intended that there is a period of time after the initiation of a first release of a desired agent and before the initiation of the second release of a desired agent.

By "low methoxy" pectin is intended pectin wherein the percent of the acid groups existing as their methyl ester is less than 40%.

By the term "delivery device" or "delivery system" is intended a preparation that is contrived to deliver a desired agent, such as a drug. The preparation can be a combination of simple or complex formulations of chemicals, with or without excipients, as noted herein. The delivery can be controlled in that the site, time, rate of release and/or actual release and delivery of a desired agent may be preset by the composition of the formulation or preparation. Such control can occur by physical and/or chemical means. In the context of the invention, "delivery device" and "delivery system" are interchangeable.

By the term "drug" is intended any pharmaceutical or physiological agent, composition, bioactive compound, or combination thereof, useful in the diagnosis, cure, mitigation, treatment, or prevention of a disease, or for any other medical purpose. The term "drug" is intended to be interpreted broadly and is not limited in terms of chemical composition or biological activity.

By the term "core" is intended the central part of anything. With respect to the present invention, the term "core" in particular refers to that part of the two pulse drug delivery system that is surrounded by the particulate-containing coat and which contains at least one desired agent, for example a drug, that is to be released from the delivery system.

By the term "particulate" is intended a composition composed of separate particles. In the context of the present invention, these separate particles, the particulates, are particles of a hydrophilic but insoluble polymer and are embedded in the inner coat material that surround the core. It is the taking up of liquid by these particles that creates channels, pores, or networks that allow swelling of the inner core. When the insoluble polymer swells, the individual particles of that polymer swell but stay as individual particles. They do not coalesce into a single gel (i.e., coherent gel) that would prevent the core (tablet) from disintegrating (i.e., behaving as a hydrogel).

By the term "water-insoluble" is intended not susceptible to being dissolved (in water). Within the context of the present invention, the property of water-insolubility is important as follows. Both the hydrophobic film and the hydrophilic particulates that make up the inner coat are water-insoluble and insoluble in the fluids of the gastrointestinal tract. This property is important for the hydrophobic coat so as to prevent the premature dissolution of the inner coat and the subsequent non-controlled release of the drug. This property is furthermore important for the hydrophilic particulates so that the channels formed remain intact and continue to allow liquid flow to control the timed release of the drug. The premature dissolution of the particulates would result in empty channels that would cause undesirable accelerated water uptake and/or premature drug release.

By the term "water-soluble" is intended susceptible of being dissolved (in water). The term "hydrophobic" when applied to a film means, besides its normal definition, relatively non-permeable to water and to water-soluble compounds.

The term "hydrophilic" when applied to a film, means, besides its normal definition, relatively permeable to water and to water-soluble compounds.

By the term "embedded" or "embed" is intended the firm fixation of a material in a medium. Within the context of the present invention, this term refers to particulate matter fixed in the coating medium.

The term "microcapsule," "microparticle," and "microsphere" are used in the art-recognized sense as spheroidal or partly spheroidal particles in the submicron to approximate 1000 micron range. The preferred ranges are from 1 to 200 microns, and especially from 2 to 100 microns.

By the term "channel" is intended a conduit through which a desired substance can flow. In the context of the present invention, channels are the connections formed from the uptake of water and swelling of the particulate matter in the inner coating. To pass the aqueous medium, the particulates swell or otherwise absorb water so that there is continuous contact among a series of swollen particulate matter that results in a conduits through which the aqueous medium outside of the delivery system or device can pass and ultimately be brought into contact with the core material in the device.

By the term "administer" to a patient is intended the introduction of the delivery system or device of the present invention into a subject. When administration is for the purpose of treatment, administration may be for either prophylactic or therapeutic purposes. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of this substance serves to attenuate any actual symptom.

By the term "animal" is intended any living creature that contains a gastrointestinal tract or alimentary canal and in which the devices of the present invention can be effective.

Foremost among such animals are humans; however, the invention is not intended to be so limiting, it being within the contemplation of the present invention to apply the compositions of the invention to any and all animals which may experience the benefits of the invention. Thus, the delivery system and methods of the invention are not limited to administration to humans and are especially useful for veterinary administration of drugs to any animal, including (but not limited to) pets such as dogs, cats, horses, fish and birds, zoo animals, wild animal control and treatment, and agriculturally important animals of the food and dairy industry such as cattle, milk cows, swine and poultry.

The invention is a two pulse delivery system for the delivery of one or more desired agents to the gastrointestinal tract. The two pulse delivery system of the invention is a modification of the gastrointestinal drug delivery system of WO 99/18938, U.S. application Ser. No. 09/163,202, filed Sep. 30, 1998 and U.S. application Ser. No. 08/948,235, filed Oct. 9, 1997 (each incorporated herein by reference in their entirety). The two pulse delivery system of the invention utilizes a formulation that provides a "first pulse" of a desired agent in a burst or sustained release manner, in addition to the gastrointestinal drug delivery system of U.S. application Ser. No. 09/163,202. Following release of the first pulse of the desired agent, the gastrointestinal drug delivery system of U.S. application Ser. No. 09/163,202, filed Sep. 30, 1998 (incorporated herein by reference) provides a second pulse of a desired agent.

All of the two pulse systems known in the art are limited in the amount of spatial and temporal control they provide in the delivery of the desired agents. The delivery system of the invention is unique in being able to control the time of release of the two pulses of the desired agent(s), and thereby the site of the release of each pulse, and the nature of the release of the first pulse as an immediate or short sustained release. WO99/18938 provides a single dose core system rather than a two pulse system. The pores of the delivery system described in WO 99/18938 are of a very minute and delicate nature. The nature of the system, in which the particulates on the surface of the coat must be able to absorb water for the system to function properly, lends itself to a high potential for a detrimental permanent clogging of the particulates if the coat that contains the particulates is surrounded by a further coat.

In addition, the particulate containing layer is susceptible to a problem with capping when surrounded by an additional layer. Capping occurs when the two layers unintentionally separate immediately after ingestion, rather than remaining together to retain the integrity of the delivery system until a desired time after ingestion. Capping is especially a concern when a short sustained release is desired (rather than an immediate release).

Contrary to the expectations regarding potential problems with clogging and capping of the delivery system of WO 99/18938, the inventors have discovered that the delivery system of WO 99/18938 can be further coated in a manner that does not clog—that is, destroy the particulate's ability to be exposed to water upon removal of the outer coat. In addition the outer drug containing coat of the current invention does not destroy the particulate's ability to swell upon dissolution or disintegration of the outer coat. In addition, the outer drug containing coat of the invention can be designed to obviate the capping problem. Accordingly, according to the invention, one or more agents can now be independently or otherwise separately delivered in a desired temporal, spatial and immediate or short-sustained release manner to the gastrointestinal tract and colon.

Thus, the drug delivery system of the invention serves as a means to target enterally administered drugs to various regions of the gastrointestinal tract. Accordingly, a subject in need of treatment with the desired agent, may conveniently obtain such treatment by orally ingesting the compositions of the invention.

Structurally, the double pulse delivery system of the invention contains a core material that is surrounded by two different coats (an inner coat and an outer coat). The core is adjacent to and completely surrounded by an "inner" coat. A second coat, an "outer" coat, is adjacent to and completely surrounds the inner coat. The inner coat is a distinct layer that surrounds a swellable core. The inner coat physically separates the core from the outer coat. The core and the outer coat each contain at least one desired agent. The outer coat is preferably pressed, or sprayed, over the inner coat.

The first pulse of the desired agent is present in, and delivered from, the outer coat. The first pulse can be released in an immediate release or a controlled release fashion. The outer coat can be designed to disintegrate, that is, to be a disintegrating layer. A "disintegrating" layer provides an immediate, burst delivery. Thus the outer coat can provide an immediate, burst delivery of the first pulse of the drug. When an immediate release is desired, the outer layer or outer coat generally contains the desired agent in combination with one or more excipients. These excipients can be known excipients of tablets that are well known in the art. Examples of known excipients for a pressed immediate release coat are, lactose, microcrystalline cellulose, povidone, calcium pectinate, ethylcellulose, calcium phosphate, magnesium stearate, silicon dioxide, starch, and disintegrants such as crospovidone. Examples of known excipients that may be used for a sustained release layer are hydroxypropylmethylcellulose, povidone, gelatin, waxes, low methoxy pectin, pectin, lactose, starch, silicone dioxide and magnesium stearate.

A pressed coat can be a disintegrating coat for the immediate delivery of the first pulse in the stomach, or optionally coated with an enteric coat for the immediate delivery of the drug in the upper small intestine. In another preferred embodiment, the pressed coat may be of a formulation that will give a short (one to five hours) sustained release of the first pulse of the drug followed by the second pulse as a burst after the preprogrammed delay time. As above, an enteric coating can optionally be added to this preferred embodiment depending upon whether it is desired that the release start in the stomach or in the upper small intestine.

When a spray coat is used as the outer coat it is generally formulated to contain a drug and film forming agent so that the drug is dispersed in the film that overlays the inner coat of the core. Such film forming agents are known in the art and may be for example hydroxypropylmethylcellulose, povidone, hydroxyethylcellulose, other modified celluloses known in the art, polyacrylates, polymethacrylates, and polymethyl/ethylmethacrylates. The spray coat may be formulated to give a short sustained release by forming a coat that slowly dissolves or to give an immediate release by forming a coat that dissolves quickly. In a more preferred embodiment for a sustained release delivery of the first dose of a desired agent, low methoxy pectin is used in a sustained release pressed outer layer.

The formulation of the outer coat may be the same or similar formulation as the core with the same drug or alternately with another drug. The formulation may also be any standard disintegrating tablet formulation as is well known in the art as long as the formulation adheres to the particulate containing inner coat that is next to it and that separates it from the core. The blend used to produce the pressed coat (for a short sustained release) needs to be designed so that the outer layer adheres well to the particulate containing inner coat which underlies it, so that it does not undergo "capping" or immediately separate from the coated core when wet. Formulations used to produce sustained release tablets may be used. In a preferred embodiment this outer coat layer may comprise lactose 0–50%, most preferably 25–35%, starch 0–50%, most preferably 10–15%, povidone 2–20%, most preferably 8–15%, drug 0.1–50%, most preferably 1–10%, low methoxy pectin 30–60%, most preferably 40–50%, and magnesium stearate 0–2%, most preferably 0.5–1%.

The outer coat can be designed to resist release of the first pulse of the desired agent until and unless a certain physiological condition (for example, a certain pH or enzyme) is present.

Release of the first pulse of the desired agent and the second pulse of the desired agent are separated by a predetermined period of time. The release of the second pulse of the desired agent is delayed relative to the start of the first pulse. The start of the first pulse can be immediately after ingestion of the delivery system or can be delayed by an enteric coat as mentioned above. The delay period is characterized as a time after the start of the release of the first pulse until the start of the release of the second pulse. During this time, the inner coat is still intact and there is no, or relatively little, release of the desired agent that is to be released with the second pulse. The delay period can be adjusted to allow sufficient time for differential spatial positioning of the drug delivery device so that it releases the first pulse of a desired agent at the same or a different site in the gastrointestinal tract than the second pulse of the desired agent.

The inner coat physically separates the outer coat from the core. The inner coat serves to control the rate of liquid entry into the core. The inner coat is composed of a combination of (1) a hydrophobic polymer material that is not soluble, or else is minimally soluble, in an aqueous solution and (2) hydrophilic, non-water-soluble, particulates that are embedded within the material. The inner coat is thus a mixture of insoluble hydrophilic particles embedded in a hydrophobic polymer. Preferably, the hydrophobic polymer used in the inner coat is one that is a relatively rigid hydrophobic polymer. The hydrophobic polymer that is used in the inner coat should be one that resists water entry into the core. The hydrophilic, nonsoluble particles are preferably capable of swelling, but do not necessarily need to as long as they can control the entry of aqueous solution into the core in a controlled manner. The design of the delivery system is such that the inner coat determines the rate of water uptake while the swelling of the core, which depends on the rate of water uptake and on the swelling properties of the core itself, determines the time of breach of the coat.

Upon exposure of the inner coat to the gastrointestinal environment (for example, due to dissolution of the outer coat), the insoluble hydrophilic particles, that is, the particulates, in the inner coat begin to swell or, at a minimum, to absorb the aqueous medium, and especially, water. As a result of the absorption of water, channels form that are capable of serving as conduits for the controlled entry of liquid into the core. The channels allow control of the rate and amount of water entry into the core of the system, such water coming from the outside of the coat into the core. The core preferably has the ability to swell and impart pressure on the structure of the inner coat from the inside as it absorbs water. Drug release from the core can be delayed or prevented until a predetermined time depending upon the particulate formulation that is used.

Factors that influence the rate of liquid intake by the inner coat are the weight percent of hydrophilic particles, the size of the particles, the swelling characteristics of the particles, and the degree of hydrophilicity.

The essential features of the inner coat are that it contain (1) a relatively rigid hydrophobic polymer, and (2) insoluble hydrophilic polymer particles, that preferably swell in liquid, and that allow the entry of liquid into the core in a controlled fashion by means of channels formed thereby. The polymer should be rigid enough so that when it is cast as a film, including the non-soluble hydrophilic particle, the "toughness" parameter—which is the area under the stress-strain curve in which the polymer does not tear (units are energy/area)—will give values of 0.009–0.21 MPa.

Examples of useful relatively rigid hydrophobic polymers for use in the inner coat include, but are not limited to, ethylcellulose, Eudragit® RL™, Eudragit® RS™, shellac and zein. Ethylcellulose is the preferred polymer. Ethylcellulose NE-20 is a highly preferred polymer. Eudragit® RL™ is a dimethylaminoethylacrylate/ethylmethacrylate copolymer, a copolymer based on acrylic and methacrylic acid esters with a low content of quaternary ammonium groups. The molar ratio of the ammonium groups to the remaining neutral (meth)acrylic acid esters is about 1:20. This polymer corresponds to USP/NF "Ammonio Methacrylate Coplymer Type A."

Eudragit® RS™ is an ethylmethacrylate/chlorotrimethylammoniumethyl methacrylate copolymer, a copolymer based on acrylic and methacrylic acid esters with a low content of quaternary ammonium groups. The molar ratio of the ammonium groups to the remaining neutral (meth)acrylic acid esters is 1:40. The is polymer corresponds to USP/NF "Ammonio Methacrylate Copolymer Type B."

Eudragit® L™ is a methacrylic acid/methylmethacrylate or ethylacrylate copolymer, an anionic copolymer based on methacrylic acid and methylmethacrylate or on methacrylic acid and ethylacrylate. The ratio of free carboxyl groups to the ester groups is approximately 1:1. This polymer corresponds to USP/NF "Methacrylic Acid Copolymer Type A and Type C."

The insoluble hydrophilic particles in the inner coat are preferably particles that will swell. Examples of useful substances for such particles includes, but is not limited to, polysaccharides. Such polysaccharides include, but are not limited to particles of calcium pectinate, calcium alginate, calcium xanthate, any metal salt of a polysaccharide containing an acid group where the salt renders the polysaccharide insoluble in water, microcrystalline starch, insoluble starch, any water insoluble polysaccharide (e.g., cellulose or microcrystalline cellulose), any polysaccharide rendered insoluble by interacting with a poly-cation or poly-anion, and any covalently crosslinked polysaccharide where said crosslinking renders the polysaccharide insoluble in water. Such crosslinking agents include, but are not limited to, glutaraldehyde, formaldehyde, epichlorohydrin, diacid chlorides, diisocyananates, diacid anhydrides, and diamines. In a highly-preferred embodiment, the particulate matter is, or contains, calcium pectinate.

The inner and/or outer coat, and especially the water insoluble carrier in the inner coat, may optionally contain a plasticizer to improve its properties as is known in the art.

In alternate embodiments, the inner coat includes, but is not limited to, any combination of a water-insoluble polysaccharide, water-insoluble crosslinked polysaccharide, a water-insoluble polysaccharide metal salt, a water-insoluble crosslinked protein or peptide, a water-insoluble crosslinked hydrophilic polymer in a dried powder form as the particulate and any hydrophobic polymer coating known in the art as the water-insoluble carrier. Specific examples of useful particulate material include, but are not limited to, insoluble starch, microcrystalline starch, microcrystalline cellulose, chitosan, calcium or zinc alginate, calcium xanthate, guar gum borax complex, glutaraldehyde- or formaldehyde-crosslinked guar gum, glutaraldehyde- or formaldehyde-crosslinked dextran, epichlorohydrin-crosslinked dextran, glutaraldehyde- or formaldehyde-crosslinked soluble starch, glutaraldehyde- or formaldehyde-crosslinked hydrolyzed gelatin, glutaraldehyde- or formaldehyde-crosslinked gelatin, glutaraldehyde- or formaldehyde-crosslinked collagen, any insoluble complex of a polysaccharide and a protein or peptide, glutaraldehyde- or formaldehyde-crosslinked hydroxypropylcellulose, glutaraldehyde- or formaldehyde-crosslinked hydroxyethylcellulose, glutaraldehyde- or formaldehyde-crosslinked hydroxypropylmethylcellulose, or any of the carbomers (crosslinked acrylic acid polymers). Specific examples of the water-insoluble carrier include, but are not limited to, Eudragit® RL™, Eudragit® RS™, ethylcellulose, shellac, and zein.

In preferred embodiments, the hydrophilic particles are calcium pectinate while the hydrophobic polymer is ethylcellulose. In most preferred embodiments, the hydrophobic polymer is ethycellulose (Ethocel 20) and the calcium pectinate is of a particle size of less than 149 $\mu$ with a ratio of particles to polymer of 1:1 or calcium pectinate of particle size less than 106 $\mu$ and a particle to polymer ratio of 3:2. The thickness or weight per tablet of the coating determines the lag time between the pulses. For example, when using the latter coating of Ethocel 20, calcium pectinate of particle size less than 106 $\mu$ and a particle to polymer ratio of 3:2, an 8 mg per tablet coating on cores of 5 mm diameter gave a delay time of 1 hour while a coating of 14 mg per tablet gave a delay time of 5 hours.

It should also be recognized that any material can form the embedded particulate if it meets the functional criteria necessary for performance in the two pulse delivery system of the invention. The functional requirement is that the material absorb aqueous medium from the gastrointestinal tract thereafter forming filled channels or networks whereby aqueous medium can flow into the core and allow the core to swell.

The core contains the desired agent that is to be released in the second pulse. The desired agent that is in the core is in combination with a carrier material. The carrier material is a material that swells upon contact with an aqueous medium such as that which is passed through the inner coat, for example, the aqueous medium, or water, from the gastrointestinal tract. Upon entry of aqueous medium or water into the core, which occurs upon formation of channels through the inner coat, the core swells. The swelling core then bursts the inner coat. The unveiled core (which now lacks the protection of the inner coat) then disintegrates, releasing its drug load as a second pulse.

Thus, one essential characteristic of the core is its ability to absorb aqueous medium such as that found in the gastrointestinal tract, and especially water, and, as a result, to swell, preferably considerably. The carrier material in the core must be able to swell to the degree necessary to impart sufficient pressure on the coat that the coat bursts at least in part as a result of the pressure. The core may be designed with a desired rate of swellability, e.g., rapid swelling, moderately rapid, slow, etc.

A further characteristic of the core is that it disintegrates rapidly after it has been unveiled, that is, after the coat that surrounds it has burst. Release of the drug from the core section provides a controlled release of a second pulse of the drug that is in the core, a release that is delayed relative to the release of the first pulse. As with the outer coat, the core can contain one drug, or more than one drug.

The second pulse of the drug is delivered from the coated core as the result of a bursting of the inner coat. Thus, the second pulse is delivered in an immediate delivery fashion, at the time controlled by the characteristics of the coated core in combination with the inner coat. Controlled, delayed release of the drug in the core is achieved, at least in part, by the properties of the inner coat and the core.

Upon being released from the core by the burst, the drug is no longer confined by the coat(s) or core material of the delivery system of the invention. The drug that is released can be in a form that is immediately available to deliver a desired efficacious effect. Alternatively, the drug that is released can be in a form that is may or may not be immediately active, but that provides a delayed, or sustained delivery of efficacious levels of the drug to the patient, preferably at the site of release or distal to the same.

The core can influence the rate of water intake for a given coating thickness. A relatively high concentration of water soluble salts in the core (relative to the outside of the tablet) causes a high osmotic gradient across the coating membrane, enhancing uptake of liquid.

The time at which the core will burst can be varied and set for a predetermined time by the hydrophobic/hydrophilic characteristics of the coating, especially the characteristics of the inner coat. The time of release can be adjusted by varying the number of hydrophilic particulates that are in the inner coat. For example, an inner coat with relatively more particulates will absorb water and form channels faster than a coat with relatively fewer particulates. Similarly, a particulate material that is relatively more hydrophilic will absorb water and form channels faster than a material that is relatively less hydrophilic.

The properties of the core further give it the characteristic that it disintegrates after breach of the inner coat, giving a burst of drug release at a predetermined site in a gastrointestinal tract. The drug may be embedded in the core material or otherwise associated with the core material, for example by dry admixture, or wet granulation. The core can be in the form of a matrix tablet or a capsule containing the desired agent, especially a drug. The core can be in the form of pellets of the pure agent. Alternatively, the core can contain pellets of the desired agent layered onto a separate core material. Alternatively, the core can contain microcapsules that contain the desired agent. More than one of these forms can be present and more than one desired agent can be delivered in the same delivery system. In all of these forms, release of desired agent by the bursting of the core is effective.

Thus, the core has the essential characteristics of being capable of absorbing sufficient liquid so that it swells considerably, and disintegrates rapidly after the coating is breached. By "swelling considerably" is intended that sufficient swelling occurs so as to bring about and result in a pressure that initiates and/or otherwise facilitates disintegration. By "disintegrating rapidly" is intended that the disintegration occurs essentially in a burst, the burst being sufficient to release efficacious amounts of the drug from the delivery device or system.

The essential components of the core are (1) a water insoluble polymer that is capable of swelling considerably but that does not form a strong gel (i.e., hydrogel), (2) a disintegrant, and (3) a hardness enhancer.

Useful water insoluble polymers for use in the core include, but are not limited to, an insoluble metal salt of a polysaccharide such as calcium pectinate or calcium alginate, or a heavily cross-linked polysaccharide such as glutaraldehyde-cross-linked guar gum, pectin, alginic acid, or other vegetable gum. In preferred embodiments, calcium pectinate is the water insoluble polymer. When calcium pectinate is used, it is preferably present in the core at a range of around of 20–70% (weight/weight); more preferably, 30–60%.

If a polymer is cross-linked, the cross-linking should be such that the polymer swells considerably but does not form a coherent gel. The proper degree of cross-linking (i.e., "heavy" within the context of the invention) means that a large percent of the monomer units are cross-linked, or alternatively, that there are many cross-links per polymer chain. The absolute degree of cross-linking is flexible, and is based on the desired result as explained above. Thus, cross-linking can be correlated with hydrogel formation by assays known in the art.

It should be recognized however that any swellable material, is potentially useful as the core material if it meets the functional requirements of the two pulse delivery system of the invention. The functional requirement is simply that upon contact with aqueous matter from the gastrointestinal tract that has reached the core due to contact with channels formed by the particulate matter that has absorbed water, the core swells enough to break the inner coat and disintegrates enough to allow all or most of the drug present in the core to be released in a burst. Any material with this property can be used as empirically determined to cause the necessary amount of swelling.

Disintegrants include, but are not limited to, Crospovidone and microcrystalline starch, although any suitable disintegrant is relevant. These would be known to the ordinary skilled artisan. A reference listing disintegrants and other types of dosage components can be found, for example, in *Pharmaceutical Dosage Forms: Tablets*, Vol. 1, Herbert A. Lieberman, et al., eds., Second Edition, Marcell Dekker Inc., New York, N.Y. (1984). In a highly-preferred embodiment, Crospovidone is the preferred agent. The Crospovidone is preferably present in the core at a range of about 5–12% (weight/weight) and most preferably around 10%.

The core can also contains a hardness enhancer. Useful hardness enhancers include, but are not limited to, microcrystalline cellulose (Emcocel®), starch, polyvinylpyrrolidone, low molecular weight hydroxypropylcellulose, and low molecular weight hydroxypropylmethylcellulose. In a preferred embodiment, microcrystalline cellulose (MCC) is the hardness enhancer. MCC is preferably present in the core at a range of about 20–50% (weight/weight), and most preferably 30–40%.

The core optionally contains lubricants, such as magnesium stearate or talc, glidants, such as fumed silica, binders for granulates, such as ethylcellulose, polyvinylpyrrolidone, and pectin, with ethylcellulose (NF-7) as the binder. However, other binders are known in the art (*Pharmaceutical Dosage Forms: Tablets*, Vol. 1, Herbert A. Lieberman, et al., eds., Second Edition, Marcell Dekker Inc., New York, N.Y. (1984)). Thus, the core material can include normal pharmaceutical additives and excipients. (See *Handbook of Pharmaceutical Excipients*, 2nd ed., Wade, A. and Weller, P. J., eds., American Pharmaceutical Association (1994)).

Combinations of materials are also useful for the core. For example, additional useful core materials include, but are not limited to, combinations of calcium pectinate, microcrystalline starch, starch, polyvinylpyrrolidone, microcrystalline cellulose, calcium phosphate, and cross-linked guar gum. In preferred embodiments, the core material includes a combination of calcium pectinate, microcrystalline starch, starch, microcrystalline cellulose, and calcium phosphate.

In a preferred embodiment, the core material includes calcium pectinate, Crosprovidone, microcrystalline cellulose, starch, or microcrystalline starch or any combination thereof. Alternate core materials include, but are not limited to, carboxymethylcellulose, calcium alginate, cross-linked guar gum, cross-linked polysaccharide, cross-linked vegetable gum, cross-linked hydrophilic polymer, alginic acid, sodium alginate, carrageenan, or any other standard tablet excipient known to those in the art. (See *Handbook of Pharmaceutical Excipients*, 2nd ed., Wade, A. and Weller, P. J., eds., American Pharmaceutical Association (1994)).

The core diameter can range from 1 mm to 15 mm, and is preferably 4–6 mm. The inner coat can range from 2 to 50 $mg/cm^2$ and is preferably from 4 to 30 $mg/cm^2$. The percent of particulate matter in the inner coat can range from 1 to 95% and is preferably 50–70%. The particle size of the particulate matter can range from 0.1 microns to 500 microns, and is preferably from 1 to 150 microns. The outer coat may be a spray coat of 5–100 mg per tablet, most preferably 20–50 mg per tablet. The outer coat is preferably a pressed coat of 7–10 mm diameter, most preferably 8–9 mm with a weight of 150 to 250 mg.

In a more preferred embodiment, the outer coat is further coated with a third coat, which is an enteric coat as known in the art. The enteric (third) coat is optional. An enteric coating is especially useful if the outer coat is adversely affected by the acid conditions of the stomach. Additional coatings that might be used on top of the outer coat include, but are not limited to, coatings to ease swallowing or mask taste. In U.S. application Ser. No. 09/163,202, and U.S. application Ser. No. 08/948,235, the enteric coat, if present, was adjacent to, and covered, the coating that was adjacent to the core (here termed the inner coating). Here however, the enteric coat, if present, is adjacent to, and covers, the outer coat, and does not contact the inner coat. An enteric coat allows the two pulse gastrointestinal drug delivery system of the invention to resist the acid pH of the stomach before releasing the first pulse of the desired agent and especially, to pass into the intestine before releasing the agent from the outer coat. At the high intestinal pH, the enteric coat dissolves and exposes the outer coat of the drug delivery system to the intestinal environment. A coat that is added to ease swallowing or to mask taste dissolves after swallowing, preferably in the stomach. Whether the coating is an enteric coat or a coat designed to ease swallowing or to mask taste, it is the coat composition that provides such desired property, rather than an agent that is embedded in the coat and such coat is designed to prevent contact between the fluids of the mouth and/or stomach and the outer coat of the invention. Thus while the enteric coat as described in U.S. application Ser. No. 09/163,202, and U.S. application Ser. No. 08/948,235, and the outer coat of the invention both serve to maintain the integrity of the first coat-core structure and to delay release from the same until the intestinal environment is reached, an enteric coating does not have a desired agent for release into the gastrointestinal tract incorporated into it.

In a preferred embodiment, Eudragit® L™ is used as an enteric coat to protect calcium pectinate (which is used in the inner coat) from the effects of the acid pH of the stomach. The enteric coat dissolves in the upper part of the small intestine. The particulate calcium pectinate starts to slowly swell as intestinal fluid enters the coating. After the predetermined amount of time, channels have formed, the core has swollen and the drug is released in a burst upon tablet disintegration. A thinner coat will reduce the delay in drug release and allow delivery of the drug to the distal portion of the small intestine, a thicker coat will lengthen the delay so that the second pulse is released in the colon.

The delivery system of the invention can be used for the delivery of more than one kind of desired agent, especially two different desired agents, one with each pulse, as above. Also, if desired, one or both pulses can release a desired mixture of agents. In a preferred embodiment, the desired agent is a drug.

The outer coating may be designed to delay the start of the imbibing of water by the particulates in the inner coating until the outer coating is breached or dissolved but such design is not an essential feature of the invention. Furthermore, in many embodiments of the invention, the outer core will be an immediate release form so that the added delay may not be particularly relevant.

Drug release is controlled by varying the following parameters: (1) size of the particulate matter in the inner coating; (2) thickness of the inner coating; (3) type of material forming the particulate matter; (4) ratio of particulate matter to non-nonparticulate matter in the inner coat; (5) the type of water-insoluble film forming material used for the inner coat; (6) the amount of swelling of the particulate matter; (7) the intrinsic hydrophilicity of the particulate matter; (8) the rate of swelling of the core; and (9) the salt concentration in the core.

Thus, the drug delivery system of the invention further provides a method for enterally administering a drug or other bioactive compound to a patient in need of such drug whenever it is necessary or desired that such drug be specifically provided locally in the gastrointestinal tract. In the invention, the drug that is in the core is not released solely through channels created in the coating, but is released by a burst that occurs at a predetermined time at which the inner coat is broken and the core tablet disintegrates with simultaneous release of all or most of the drug.

In the two pulse system embodiment of the invention the first pulse is preferably released in the stomach, small intestine or ascending colon with the second pulse being released in a part of the gastrointestinal tract distal to the site of the first pulse (i.e. the small intestine, ascending colon, transverse colon or descending colon, depending on where the first pulse was released and the delay between the pulses). Especially preferable areas for drug release are the duodenum for the first pulse and the colon for the second pulse.

The drug delivery system further provides a method for delivering efficacious levels of one or more drugs designed for local treatment of diseases of particular areas of the alimentary tract. These diseases include, but are not limited to, inflammatory bowel disease, Crohn's disease, colitis, irritable bowel syndrome (IBS), local spasmolytic action, ulceration of the mucosa, diarrhea, constipation, polyps, carcinomas, cysts, infectious disorders, and parasitic disorders. The drug delivery system further provides a method for oral immunization through either the Peyer's Patches or through the colon.

The drug delivery system further offers the ability for targeting the local delivery of agents for photodynamic therapy.

The drug delivery system can be used for the systemic delivery of efficacious levels of drugs through a targeted area of the alimentary canal. Drugs that are better absorbed, and/or show lesser side effects, in the distal parts of the alimentary canal can be directed to those sites. The delivery system allows delivery to the duodenum, jejunum, ileum, ascending colon, transverse colon, and descending colon as the site for systemic drug delivery.

The invention is also directed to a method for the preparation of the drug delivery system. The preferred method of preparation is by the preparation of a suspension of the hydrophilic, water-insoluble particulate in an alcoholic solution of a hydrophobic polymer. This suspension is spray coated onto the core tablet or capsule using conventional pan coating technology.

The delivery system of the invention provides many advantages over the sustained delivery of drugs. First, delivery of a desired agent such as a drug in pulses allows the body time to readjust between doses. The readjustment time helps alleviate the build up of tolerance.

Second, the pulsed delivery of the invention maximizes the targeting and thus delivery of the desired agent such as desired drugs that are poorly absorbed through the membranes of the GI tract. Localizing the release of the drug in space and time allows a relatively large concentration to be presented at the membrane surface for concentration driven diffusion of the drug.

Third, the ability to carefully control the timing of the release between doses of potent drugs or combinations of drugs is a further advantage to the two pulse delivery system of the invention. Patients cannot usually be trusted to take their medicines at exact predetermined times. The timing of potent drugs can improve their efficacy and limit their side effects. The two pulse drug delivery system allows the practitioner to control of the time between the two pulses of the drug and is not dependent on the patient's compliance with a rigorous timing schedule.

Fourth, the two pulse delivery system of the invention allows control over the site at which the second pulse of the drug occurs.

Fifth, the two pulse delivery system of the invention allows for a spatial and temporal separation of the delivery of the two different drugs. This may be advantageous to treat a condition. Drugs that might adversely interact with each other or adversely effect the absorption of each other into the body can be administered together and delivered to separate sites at separate times.

Sixth, the invention is useful for local or targeted delivery of a drug where slow release is undesirable or where a high-peak concentration is necessary. It is also advantageous to improve the absorption of poorly absorbed drugs by providing a strong (steep) concentration gradient across the lumen at a point considered to be suitable, whether in the small intestine or in the colon, although in preferred embodiments the site of drug release of at least the agent in the core is the colon.

Seventh, the invention is especially useful for the delivery of drugs that have a high rate of first pass metabolism. Delivery according to the device of the invention allows such drugs the maximum opportunity to attain efficacious concentrations. By delivering a burst of the drug the concentration attained is able to saturate the metabolic pathways and to reach an efficacious concentration of the drug in the blood. Slow sustained delivery of the drug would deliver it in a fashion which is optimized for destructive metabolism leaving ineffective concentrations of the drug in the body. Since these drugs usually show a short half life requiring multiple administrations, the double pulse tablet is a method of improving dosing regimens for these drugs and thus improving efficacy and patient compliance.

In a preferred embodiment, the first pulse is delivered in the upper gastrointestinal tract (the stomach or the small intestine) in either an "immediate delivery" or a "relatively short sustained delivery" fashion. The time of the second pulse is pre-programmed to a desired delay between the pulses. This delay serves to separate the two pulses of the drug in time and location and to target the second pulse to a specific location along the gastrointestinal tract. The second pulse of drug is delivered in an immediate fashion. The features that allow this capability are an inner core that is capable of absorbing liquid and swelling enough to cause breakage of the coating surrounding said core, the core disintegrating rapidly after the integrity of the coating is breached; a particulate containing coating such that the particles serve as filled channels for the controlled entry of liquid into the core; and an outer layer of drug formulated to delivery drug either in an immediate or sustained fashion.

In a preferred embodiment, the form of the core includes tablets and pellets, especially compressed tablets and matrix tablets. In a highly preferred embodiment of the invention, the delivery system or device is a tablet that contains a core material which is a disintegrating tablet. The tablet is made with standard granulation and tableting techniques and is coated using pan coat technology. Instead of a solution, a suspension of the particulate material in a solution or fine suspension of the polymeric coating material is sprayed on the tablets. The suspension is stirred to keep it relatively homogeneous. Warm or cold air is flowed over the tablets to allow for the film to form and the tablets to dry. Suitable solvents for such polymeric solutions or suspensions are the typical solvents known to those in the art for spray coating tablets and include, but are not limited to, water, ethanol, acetone and isopropanol. Ethanol is the preferred solvent.

In a further preferred embodiment, the diameter of the core is 1–10 mm, preferably 4–6 mm. The core formulation is one that swells without appreciable gel formation. A particularly preferred formulation comprises a drug such as sodium diclofenac or pyridostigmine bromide, a disintegrating agent such as crospovidone, a swelling polymer such as calcium pectinate and a hardness enhancer such as microcrystalline cellulose. In preferred embodiments the calcium pectinate is present from 20–50%, most preferably 30–35%, the crospovidone from 5–15%, most preferably 10–12%, the drug from 0.1–40%, most preferably 2–10%, microcrystalline cellulose 20–60%, most preferably 45–55%, silicone dioxide (as an optional glidant) 0–2%, most preferably 0.5–1%, Eudragit® S or povidone (as an optional granulation binder) 0–3%, most preferably 0.5–2%, and magnesium stearate 0–2%, most preferably 0.5–1%.

Dysfunction of colon motility may be characterized by (i) inability of the colonic motor activity to propel fecal content into the caucad direction (colonic inertia or gastroparesis); and (ii) inability of the colonic motor activity to provide the propulsive force at the time of defecation (colonic pseudo-obstruction). In most of the cases the dysfunction in the colonic motility originates in neurological disorders. Therapy in these cases should therefore be directed towards improving the transit of intraluminal contents, by modulating the neural control systems.

Prokinetic agents, that is, agents that enhance the transit of material through the GI tract, can be administered using the two pulse delivery system of the invention. Prokinetic agents affect the GI motility by action at specific cellular drug-receptor interactions, may interfere with the release of one or more mediators affecting GI motility, such as acetylcholine or dopamine, or may act directly on the smooth muscle. The two pulse drug delivery system of the invention can be used to stimulate treat GI motility by delivering dopamine antagonists, such as metoclopramide and domperidone, or by substances which enhance acetylcholine release, such as metoclopramide and cisapride, or by substances that directly bind to muscarinic receptors on the smooth muscle, such as bethanecol to the patient in need of the same.

Examples of drugs that are especially desirable and that can be delivered using the pulsed delivery system of the invention include agents that need timed doses of a drug or two different drugs that do not depend on the patient's compliance with a dosing schedule. Examples of such drugs include antibiotics such as neomycin, β-lactam antibiotics such as ampicillin and amoxicillin, cephalosporins such as cephalexin and cloxacillin and macrolide antibiotics such as erythromycin, oxybutinin (especially, for incontinence), ondanseteron hydrochloride (especially for preventing nausea), and oxprenolol hydrochloride and propanolol (especially for hypertension and for cardiac arrhythmias). Other drugs include drugs that are poorly absorbed through the membranes of the GI tract. Localizing the release of the drug in space and time allows a relatively large concentration to be presented at the membrane surface for concentration driven diffusion of the drug. Examples of such drugs include protein or peptide drugs, such as insulin, human growth hormone, interleukin II, interferon, calcitonin, colony-stimulating factor, leuprolide, and gonadorelin, bis phosphonate drugs such as disodium clodronate, disodium etidronate, and disodium pamidronate, and polysaccharide drugs such as short chain heparin.

The pulsed delivery is also useful for drugs that have a high rate of first pass metabolism in order to attain efficacious concentrations. By delivering a burst of the drug the concentration attained is able to saturate the metabolic pathways and to leave an efficacious concentration of the drug in the blood. Examples of such drugs include oxpentifylline (especially for peripheral vasodilatation), a dopamine agonist such as bromocryptine mesylate, reversible inhibitors or acetylcholinesterase such as physostigmine, pyridostigmine bromide, and rivastigmine (especially for gastrointestinal motility or for treatment of Alzheimer's disease), and dihydroergotamine (especially, for the treatment of migraine).

Further examples of drugs include drugs for which the body develops tolerance. Delivery of the drug in pulses allows the body to readjust by allowing time in between doses and therefore may alleviate the build up of tolerance. Examples of such drugs include nitroglycerine, isosorbide dinitrate, isosorbide mononitrate and opioid drugs such as morphine. Further examples of drugs include those that need to be delivered to two distinct sites in the gastrointestinal tract during one administration of the drug. Examples of such drugs include mesalazine or corticosteroid drugs (especially for the topical treatment of Crohn's disease in both the small intestine and colon), and prokinetic drugs such as cisapride and metoclopramide (especially for the treatment of upper and lower gastrointestintal (GI) tract motility problems at the same time).

The therapeutic benefits of the delivery system flow from its ability to delivery efficacious levels of a desired agent, for example, a drug to a specific site in the gastrointestinal tract. This allows the local treatment of diseases including, but not limited to, ulcerative colitis, Crohn's disease, colon carcinoma, esophagitis, *Candida esophagitis*, duodenal ulcers, gastric ulcers, Zollinger-Ellison Syndrome (gastrinoma), gastritis, chronic constipation, diarrhea, pancreatitis, local spasms, local infections, parasites, and other changes within the gastrointestinal tract due to effects of systemic disorders (e.g., vascular inflammatory, infectious and neoplastic conditions).

Treatment methods for disease states of the colon can utilize the delivery system of the invention to provide an the immediate release of a drug in the colon. Severe constipation, whether idiopathic or caused by drugs (e.g. morphine, dopamine) or by disease states (e.g. Parkinson's, spinal chord injury, multiple sclerosis, diabetes mellitus) are often caused by dysfunction of colonic motility (Sarna, S. K., *Digest. Dis. & Sci.* 36:827–882 (1991); Sarna, S. K., *Digest. Dis. & Sci.* 36:998–1018 (1991)) and drugs or other agents for the treatment of the same can be administered using the delivery system of the invention. Direct delivery of drugs to these regions enhances the amount of drug absorbed in this region and the amount of drug to which the cells in the region are directly exposed. Direct delivery or targeting of drugs also decreases the systemic distribution of drugs and thereby reduces undesirable and potentially harmful side effects.

The delivery system of the invention is useful for delivery to the colon of any drug that can be absorbed in the colon, such as, inter alia, steroids and xanthines. Propranolol, oxyprenolol, metropolol, timolol, and benazepril are known to be preferentially absorbed in the jejunum while cimetidine, furosemide, hydrochlothiazide, and amoxicillin are known to be preferentially absorbed in the duodenum. For a review, see Rubinstein, A., *Biopharm. Drug Dispos.* 11:465–475 (1990).

Examples of additional agents that can be provided for colonic delivery using the two pulse delivery system of the invention include nonsteroidal anti-inflammatory drugs (NSAID) such as sulindac, diclofenac, flurbiprofen, indomethacin, and aspirin; steroid drugs such as dexamethasone, budesonide, beclomethasone, flucticasone, tioxocortol, and hydrocortisone; contraceptives or steroidal hormones such as estrogen, estradiol and testosterone; immunosuppressants such as cyclosporin; bronchodilators such as theophylline and salbutamol; anti-anginals and anti-hypertensives such as isosorbide dinitrate, isosorbide mononitrate, nitroglycerine, nifedipine, oxyprenolol, diltiazem, captopril, atenolol, benazepril, metoprolol, and vasopril; anti-spasmodic agents such as cimetropium bromide; anti-colitis agents such as 5-aminosalicylic acid; anti-arrhythmia agents such as quinidine, verapamil, procainamide, and lidocaine; anti-neoplastic agents such as methotrexate, tamoxifen, cyclophosphamide, mercaptopurine, and etoposide; protein or peptide drugs such as insulin, human growth hormone, interleukin-II, interferon, calcitonin, colony-stimulating factor, leuprolide, tumor necrosis factor, bone growth factor, melanocyte-stimulating hormone, captopril, somatostatin, somatostatin octapeptide analog, cyclosporin, renin inhibitor, superoxide dismutase, other hormones and vaccines; proteins or peptides containing antigens of tissues under autoimmune attack for absorption via Peyers patches (Cardenas, L. and Clements, J. D., *Clin. Microbiol. Rev.* 5/3: 328–342 (1992), anticoagulants such as heparin or short chain heparin, anti-migraine drugs such as ergotamine; glibenclamide; 5-hydroxytryptamine type$_{1A}$ receptor agonist gepiron; 5HT$_3$ antagonist ondasteron; metkephamid; menthol; antibiotics such as neomycin, β-lactams such as ampicillin and amoxicillin, cephalosporins such as cephalexin and cloxacillin, and macrolides such as erythromycin; PGE$_1$ analogues for protecting the gastroduodenal mucosa from NSAID injury, such as misoprostol; prokinetic drugs such as metoclopramide and cisapride; cholinergic agonists such as bethanecol, carbachol, methacholine and pilocarpine; dopamine antagonists such as metoclopramide and domperidone; and reversible inhibitors of acetylcholinesterase, such as neostigmine and its salts, physostigmine and its salts, and pyridostigmine bromide. Protein drugs, such as LH-RH and insulin, may survive longer and be absorbed better from the colon than from the small intestine. Other drugs have been shown to possess colonic absorption, such as diclofenac, quinidine, theophylline, isosorbide dinitrate, nifedipine, oxprenolol, metoprolol, glibenclamide, 5-hydroxytryptamine type$_{1A}$ receptor agonist gepiron, 5HT$_3$ antagonist ondasteron, metkephamid, menthol, benazepril (ACE inhibitor).

Examples of drugs that are useful for treating various other regions of the alimentary canal and that can be provided using the delivery system of the invention include: for the treatment of Gastro Esophagal Reflux Disease-H2 receptor antagonists (e.g., Tagamet, Zantac) and proton pump inhibitors (e.g., Omeprazole); for the treatment of Candida esophagitis-nystatin or clotrimazole; for the treatment of Duodenal Ulcer-H2 receptor agonists, prostaglandins (e.g., Cytotec, Prostin), and proton pump inhibitors—(e.g., Prilosec, Omeprazole, Sucralfate); for the treatment of Pathological Hypersecretory Conditions, Zollinger-Ellison Syndrome-H2 receptor agonists; for the treatment of Gastritis-H2 receptor agonists, PGE$_1$ analogs for protecting the gastroduodenal mucosa from NSAID injury such as misoprostol, GHR-IH drugs for treating pancreatitis, such as somatostatin, and anti-spasmodic drugs for treating local spasmolytic action such as cimetropium bromide.

High concentrations of a drug obtained by an immediate release of the drug in a predetermined section of the gastrointestinal tract may enhance absorption of poorly-absorbable drugs by means of an enhanced concentration gradient.

The delivery system or delivery device is also useful for diagnostic purposes, such as site-specific delivery of x-ray contrast agents (e.g., barium sulfate, Diatrizoate Sodium, other iodine containing contrast agents) ultrasound contrast agents (e.g., air-containing microspheres), contrast or enhancement agents for magnetic resonance imaging, tomography, or positron emission agents. The delivery system and delivery device are further useful for the delivery of monoclonal antibody markers for tumors.

Specific embodiments of prepared formulations of the compositions of the invention, include, for example, matrix-drug tablets, especially tablets prepared by compression; matrix-drug pellets, either free or packed in gelatine capsules, or any other means allowing oral administration; matrix-drug nanoparticles, either free or packed in gelatine capsules or any other means allowing oral administration; and multi-layered tablets, coated capsules, coated microcapsules, coated pellets or micropellets, coated pellets or micropellets in a capsule, coated pellets or micropellets in a coated capsule, coated pellets, micropellets or microcapsules pressed into a tablet and coated pellets, micropellets or microcapsules pressed into a tablet and further coated. All of the techniques for preparation of such formulations are well known in the art.

The amount of drug can vary as desired for efficacious delivery of the desired drug and in consideration of the patient's age, sex, physical condition, disease, and other medical criteria. In addition, the amount of drug delivered by the system of the invention will depend upon the relative efficacy of the drug. The amount of specific drug necessary for efficacious results in the delivery system and methods of the invention may be determined according to techniques known in the art. For example, recommended dosages such as known in the art (for example, see the *Physicians' Desk Reference*, (E. R. Barnhart, publisher), *The Merck Index*, Merck & Co., New Jersey, and *The Pharmacological Basis of Therapeutics*, A. G. Goodman et al., eds., Pergamon Press, New York), provide a basis upon which to estimate the amount of a drug which has been previously been required to provide an efficacious level of activity.

Examples of drugs whose efficacious amounts for use in the delivery system of the invention may be determined in this manner include each of the previously mentioned drugs.

Tablets and capsules may be prepared and tested by techniques well known in the art, for example, as described in *Remington's Pharmaceutical Sciences*, Mack Publishing Company, and especially in chapter 89, the pharmaceutical preparation and manufacture of "Tablets, Capsules and Pills." In all embodiments, if desired, more than one drug may be supplied to the patient in the same matrix.

In the tablet embodiments, for example, the compositions of the invention may provide a wide range of drug amounts, for example, the amount of drug can vary from about 0.01–95% by weight.

In another embodiment, a compressed tablet is formulated to contain efficacious levels of the desired drug(s) or pharmaceutical compound(s) as in the tablet embodiment, and an amount of the components of the invention that would allow disintegration of the tablet and release of the drug(s) following exposure of the tablet to one or more microorganisms present in the colon. Other suitable embodiments will be known to those of skill in the art.

The following examples further describe the materials and methods used in carrying out the invention. The examples are not intended to limit the invention in any manner.

EXAMPLES 1–7

Materials and Methods

Calcium pectinate powder containing 4% calcium (food grade) was supplied by Genu-Copenhagen Pectin (Denmark). For the preparation of the coating suspension, calcium pectinate underwent fractionation using a sieve shaker (Levy Laboratory Equipment, LTD) and sieve of 149 $\mu$ (ASTM 100, 8" diameter) in order to obtain the fraction of <149 $\mu$ particle size. Emcocel® 90M (microcrystalline cellulose) (BP grade), Eudragit® E 100 (Eud.E), ethylcellulose EC-N100 NF 0100 (EC), magnesium stearate (USP grade), cross polyvinylpyrrolidone (USP grade) (CPVP or Crospovidone), sodium diclofenac (BP grade) and sodium salicylate (USP grade) were purchased from Mendel, Rohm Pharma (Germany), Aqualon (Netherlands), Merck (Germany), Basf, Amoli Organics (India) and Merck (Germany), respectively. Pyridostigmine bromide was purchased from Orgasynth Industries (France). Ethyl alcohol was USP grade.

Granulation or a dry mixing method was used to prepare the blends for compressing in a tablet press. For dry mixing, all components of a formulation except magnesium stearate were mixed manually for 20 to 30 minutes in a polyethylene bag. Then magnesium stearate was added and the blend underwent additional mixing for about 2 to 3 minutes. Granulation will be described for each individual experiment.

Biconvex cores of 8 mm diameter were compressed automatically using a Korsh EK 0 single punch tablet press operated by the Erweka drive unit (AR 400). The weights of cores ranged between 220 to 300 mg depending on the core formulation. The hardness of the cores was tested using a Schleninger-2E Hardness Tester.

Biconvex cores of 9 mm diameter were also compressed automatically using a 15 punch Kilian RLS-15 tablet press fitted with a control unit type ROF-M. The hardness of the latter cores were measured using a Vankel VK200RC hardness tester.

The coating suspension was prepared by dissolving ethylcellulose (4% w/w) (8 g EC/200 g solution), in ethanol and then adding the calcium pectinate powder, to the desired weight ratio. The coating suspension was then kept stirred vigorously throughout the coating process to prevent the calcium pectinate deposition. The coating system consisted of a polyethylene pan coater (~12 cm diameter), an Heidolph (RZR 2051, electronic) driving motor, a peristaltic pump (Masterflex, Digital Console Drive, Cole-Palmer Instrument Company) and a nozzle composed from a "Y" connector tube fixed on one end to the air supply system and on the other to the coating suspension through the peristaltic pump and a stainless steel tip of 1.2 mm fixed at the head of the "Y" connector tube. The coating conditions such as the temperature, spraying rate (flow velocity of the suspension), air pressure (for the suspension spraying), air flow rate of the fan, and the rotation speed of the fan were kept constant throughout the coating process.

Dissolution studies were performed in intestinal fluid TS (phosphate buffer, pH 7.5 without enzymes) using a Vankel 7000 dissolution tester. One tablet was placed in 900 ml intestinal fluid TS and stirred by paddle at 50 RPM. The solutions were kept at 37° C. by a Vankel VK650A heater/circulator. Samples of 3 ml were taken using a Vankel VK8000 Autosampler, at intervals of 30 minutes up to 4 hours, followed by intervals of 1 hour up to 12 hours and finally intervals of 2 hours up to 20 hours. The actual determinations of the release of the drugs (dissolution results) from both coated and uncoated tablet were carried out using a HP 8452A Diode-Array Spectrophotometer. The drugs released from the coated and uncoated tablets were quantified using a calibration curve obtained from the standard solution, in intestinal solution TS, in the concentration range of 0–50 ppm.

EXAMPLE 1

Control of Burst Time by Weight (Thickness) of Coating

Tablets were produced using dry mixing of components. The formulation of the core is given in Table 1 (229-76A). The cores were of 8 mm diameter and had a hardness of 11–12 Kp. The uncoated core underwent disintegration in intestinal TS within several seconds releasing all the diclofenac. The cores were spray coated with different amounts of ethylcellulose:calcium pectinate (1:1 w/w). The results are shown in FIG. 1. An 8 mg coating per tablet gave a delay of 2 hours; 11 mg gave a delay of 4 hours; 17 mg a delay of 9 hours; 20 mg gave a delay of 12 hours. In each case the tablets fully disintegrated after the delay time.

Figure 2:
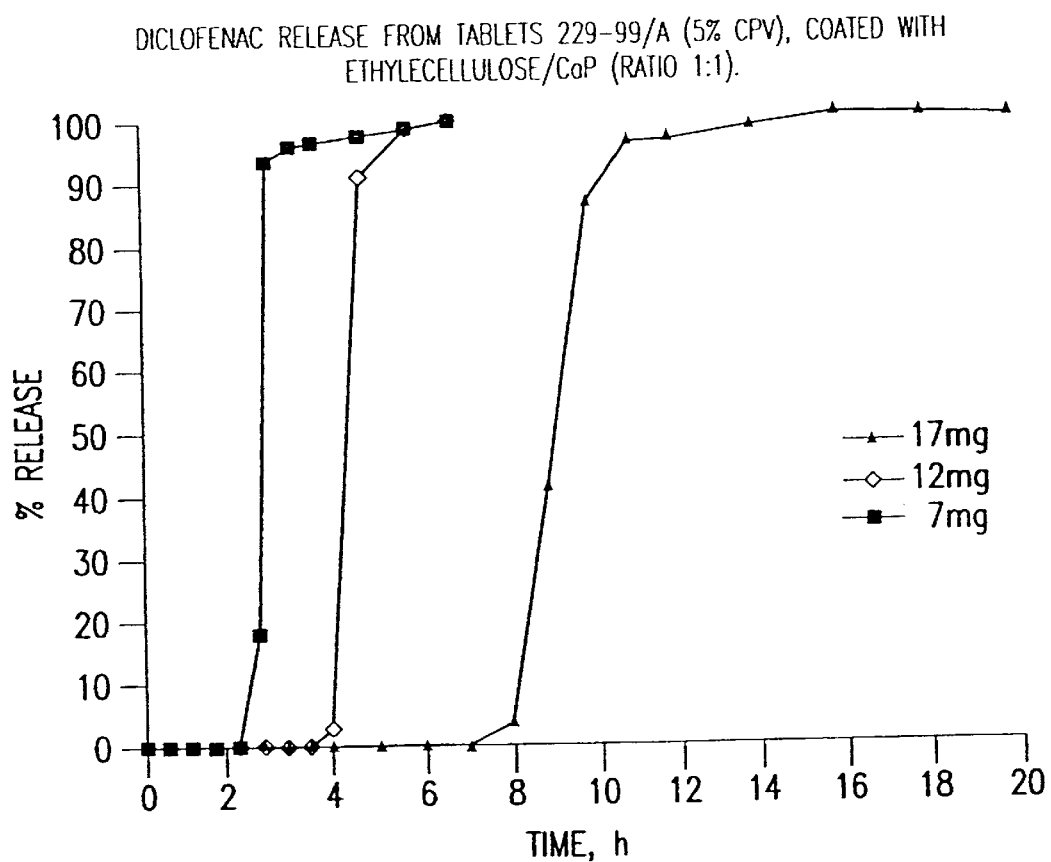
FIG. 2. Diclofenac release from tablets 229-99/A (5% CPV), coated with ethylcellulose/CaP (ratio 1:1).

Reducing the amount of Crospovidone to 5% (formulation 229-99A) gave essentially identical results. In FIG. 2, a 7 mg per tablet coating resulted in a delay of 2 hours; 12 mg resulted in a delay of 4 hours; and 17 mg resulted in a delay of 8 hours, before the drug was released in a burst. Formulations without Crospovidone did not provide a burst at all.

TABLE 1

Tablet Core Formulations

|  | 229-76A | 229-99A |
|---|---|---|
| Ca pectinate % | 59 | 59 |
| Emcocel ® % | 20 | 25 |
| CPVP % | 10 | 5 |
| Na-diclofenac % | 10 | 10 |
| Mg-Stearate % | 1 | 1 |
| Diameter mm | 8 | 8 |
| Hardness kp | 12 | 12 |
| Weight mg | 259.4 | 256.5 |

EXAMPLE 2

Effect of Tablet Hardness

Cores of tablets were made using the dry mixing method and compressed at different compression forces so as to create tablets with different hardness. The formulation was identical to that of 229-76A (Table 1). Tablet cores 229-93B gave a hardness of 11–13 kp while tablet cores 229-93A gave a hardness of 5–8 kp. The cores were spray coated with ethylcellulose:calcium pectinate at a weight/weight ratio of 1:1 as in Example 1.

Figure 3:
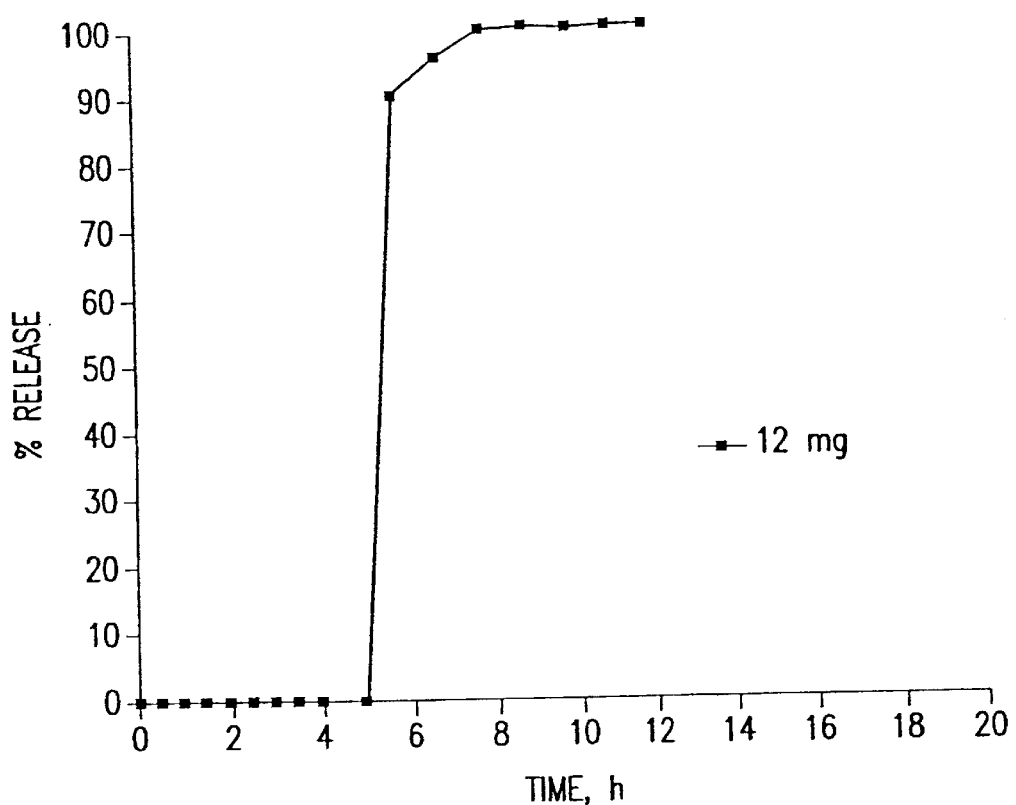
FIG. 3. Diclofenac release from tablets 229-93/B (hardness 11–13), coated with ethylcellolose/CaP (ratio 1:1).
Figure 4:
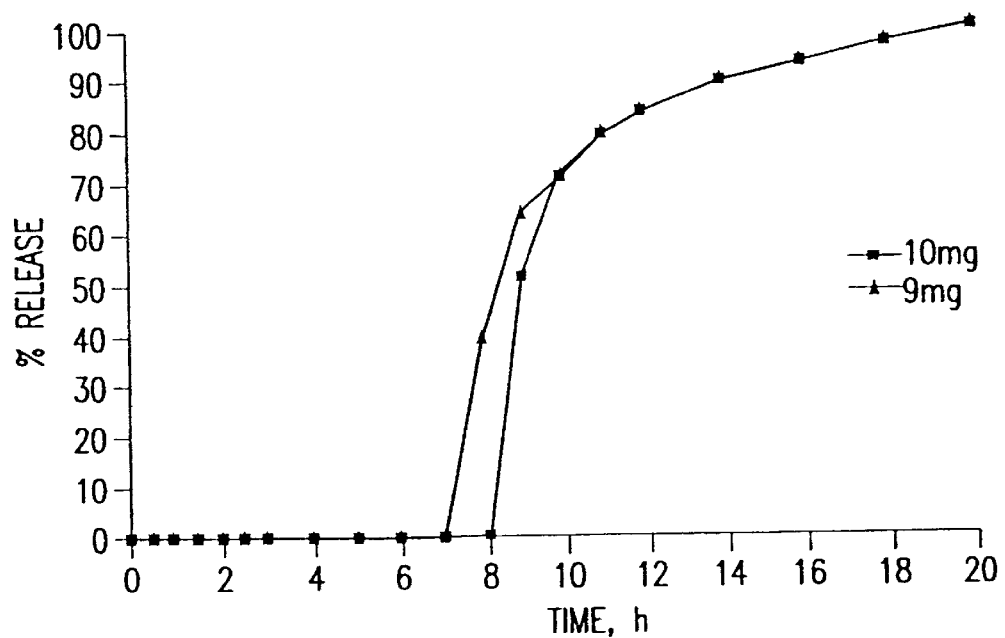
FIG. 4. Diclofenac release from tablets 229-93/A (hardness 5–6), coated with ethylcellulose/CaP (ratio 1:1).

Dissolution studies of coated tablets 229-93B, shown in FIG. 3 showed that a 12 mg coating per tablet gave a five hour delay before the drug was released in a burst. Coated tablets 229-93A did not show a burst of drug release. After a delay of 7–8 hours for a coating level of about 10 mg per tablet, the drug was released in a slow fashion (FIG. 4).

EXAMPLE 3

Effect of Hardness Enhancer (Emcocel®) and Swelling Component (Calcium Pectinate)

Tablet cores were formulated without either Emcocel® (formulation 229-99B, see Table 2), or without the swelling polymer calcium pectinate (formulation 229-99C, see Table 2). The tablets were produced under conditions of compression that gave them almost identical hardness.

TABLE 2

Tablet Core Formulations

|  | 229-99B | 229-99C |
|---|---|---|
| Ca pectinate % | 79 | 0 |
| Emcocel ® % | 0 | 79 |
| CPVP % | 10 | 10 |
| Na-diclofenac % | 10 | 10 |
| Mg-Stearate % | 1 | 1 |
| Diameter mm | 8 | 8 |
| Hardness kp | 12 | 12.5 |
| Weight mg | 255.4 | 224.1 |

The tablets were spray coated as in Example 1. In both cases, the tablets failed to show clean burst drug release. After a delay in drug release which is coating weight dependent, the drug was released in a burst of part of the drug content with the remainder being released slowly.

EXAMPLE 4

Effect of Drug Solubility on the System

Figure 5:
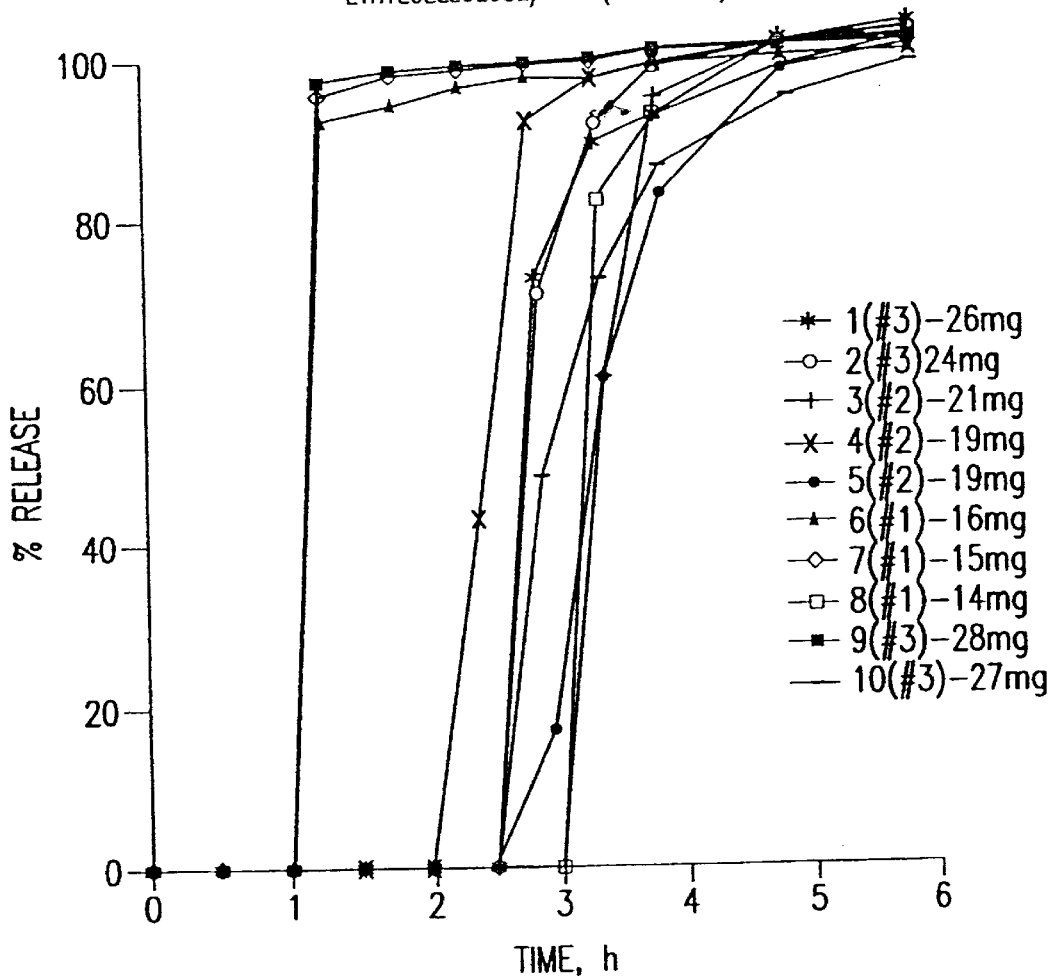
FIG. 5. Sodium salicylate release from tablets 229-113, coated with ethylcellulose/CaP (ratio 1:1).

Tablets were formulated using the highly soluble drug sodium salicylate instead of the partially soluble sodium diclofenac. The formulation used is described in Table 3. The tablets were spray coated with varying thicknesses of ethylcellulose: calcium pectinate (1:1) as in Example 1. FIG. 5 shows the results of the dissolution of these tablets in intestinal TS. The sodium salicylate, being more soluble, causes a quicker entry of water into the tablet bringing about a lowering in lag times for a given coating thickness (compare FIGS. 1 and 5). A 15 mg coating gave only one hour delay time, a 19 mg coating per tablet gave a two hour delay to the drug burst while a 24 mg coating gave a 2.5–3 hour delay. The osmotic drive for water entry is higher if the drug (a salt) is present in higher concentrations in the tablet. To prove this explanation we obtained similar results by formulating tablets of sodium diclofenac with the addition of calcium chloride (Table 3). These tablets were also spray coated as in Example 1. A coating of 19 mg gave a delay to burst of one hour when compared to a delay of 9 hours for a 17 mg coating seen in Example 1.

TABLE 3

Tablet Core Formulations

|  | 229-113 | 229-85B |
|---|---|---|
| Ca pectinate % | 59 | 59 |
| Emcocel ® % | 20 | 25 |
| CPVP % | 10 | 0 |
| $CaCl_2$ % | 0 | 5 |
| Na-diclofenac % | 0 | 10 |
| sodium salicylate % | 10 | 0 |
| Mg-Stearate % | 1 | 1 |
| Diameter mm | 8 | 8 |
| Hardness kp | 12 | 9.5 |
| Weight mg | 262.7 | 293.8 |

EXAMPLE 5

Cores Made with Granulation

Tablet cores were produced using a wet granulation method. The advantage of wet granulation over dry mixing is one of improved uniformity of content for low concentration, potent drugs, and of enhanced batch to batch reproducibility of the process. The granulation also improves the flowability of the powder and the hardness of the obtained tablets. The granulation was carried out as follows: 5.4 g of low viscosity ethylcellulose (e.g. nf-7) was dissolved in 90 ml ethanol, 265 g calcium pectinate was mixed with 15.75 g Crospovidone. The ethylcellulose solution was added slowly. The mixture was well mixed in a mortar and pestle and then dried at 60–65 degrees for 1.5 hours and at 40 degrees for overnight.

Low viscosity ethylcellulose (0.9 g) was dissolved in 15 ml ethanol. Diclofenac (45 g) was mixed with 2.7 g of Crospovidone and the ethylcellulose solution was added. The mixture was mixed with a mortar and pestle and dried overnight at 40 degrees. The granulates were then mixed with the remainder of the components and tablets pressed.

TABLE 4

Tablet Core Formulation

|  | 263-129 |
|---|---|
| Ca pectinate Granulate % | 28.3 |
| Emcocel ® (90M) % | 50 |
| CPVP % | 10 |

TABLE 4-continued

Tablet Core Formulation

|  | 263-129 |
| --- | --- |
| Na-diclofenac granulate % | 10.7 |
| Mg-Stearate % | 1 |
| Diameter mm | 7 |
| Hardness kp | 10 |
| Weight mg | 204.7 |

Figure 6:
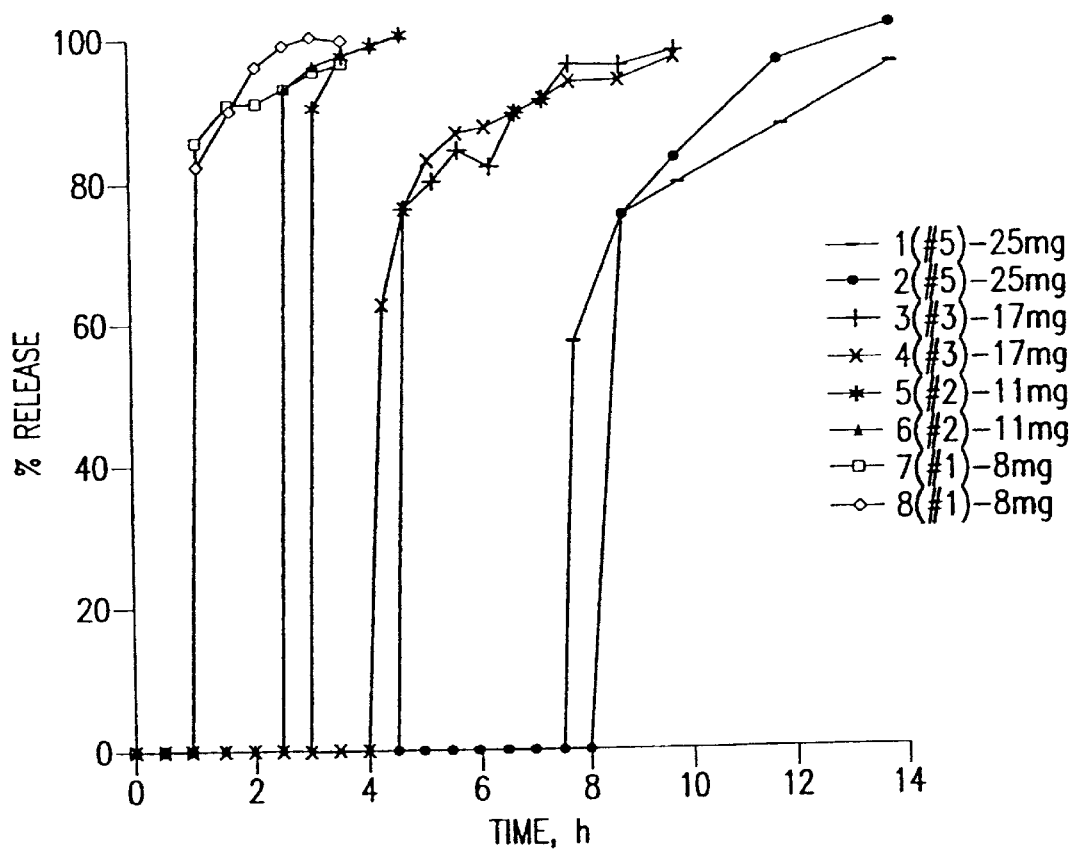
FIG. 6. Diclofenac release from tablets 263-129 (granulated CaP+CPV+EC, granulated diclofenac+CPV+EC; 50% Emcocel®; D=7 mm), coated with ethocel 20/CaP (ratio 1:1).

The granulated calcium pectinate swells more efficiently than the calcium pectinate powder allowing a lowering of the percentage of calcium pectinate in the formulation. Tablets of formulation 263-129 (Table 4) were pressed and were coated with ethylcellulose; calcium pectinate (1:1). The dissolution was studied in intestinal TS. The results are shown in FIG. 6. Tablets coated with 8 mg per table gave a one hour delay to burst. Tablets coated with 11 mg gave a 2.5–3 hour delay. Tablets coated with 17 mg gave a delay of 4–4.5 hours. 25 mg gave a 7.5 to 8 hour delay.

EXAMPLE 6

Control of Burst Time by Changing EC: CaP Ratio

Figure 7:
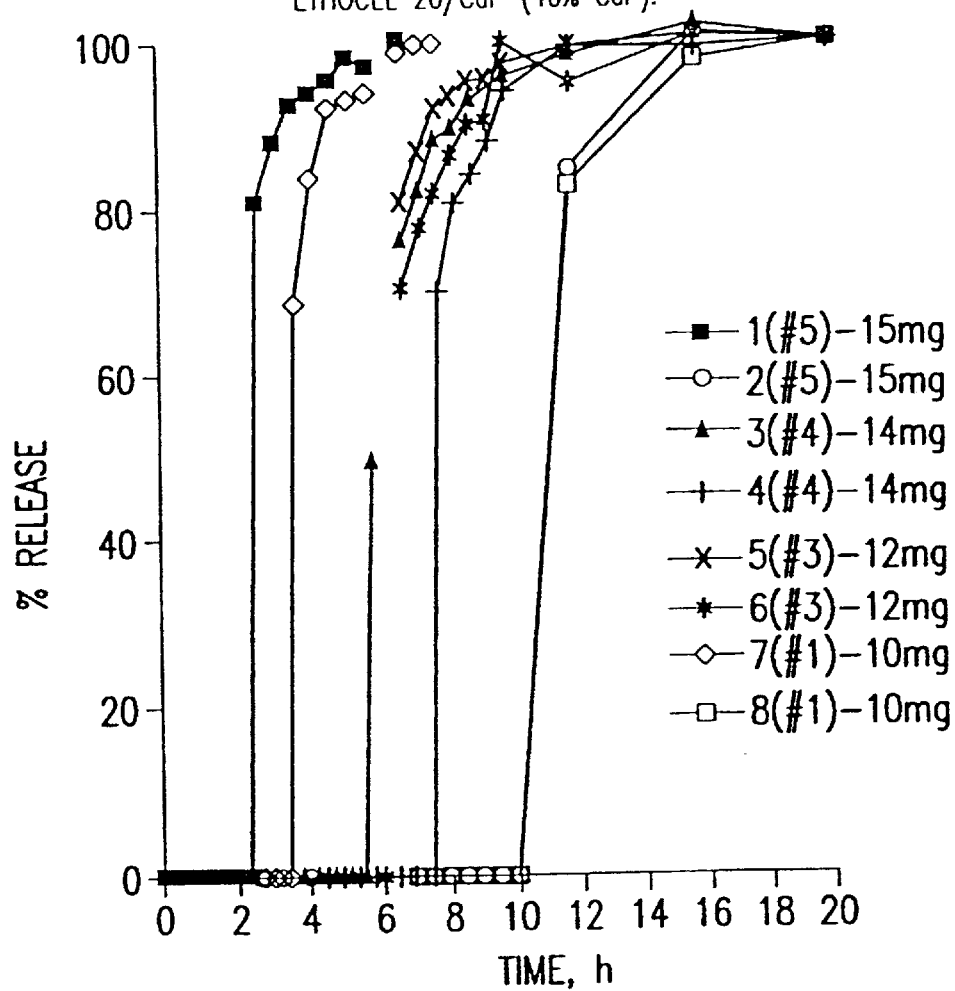
FIG. 7. Diclofenac release from tablets 263-123 (granulated CaP+CPV+EC, granulated diclofenac+CPV+EC; 50% Emcocel®; D=7 mm), coated with ethocel 20/CaP (40% CaP).
Figure 8:
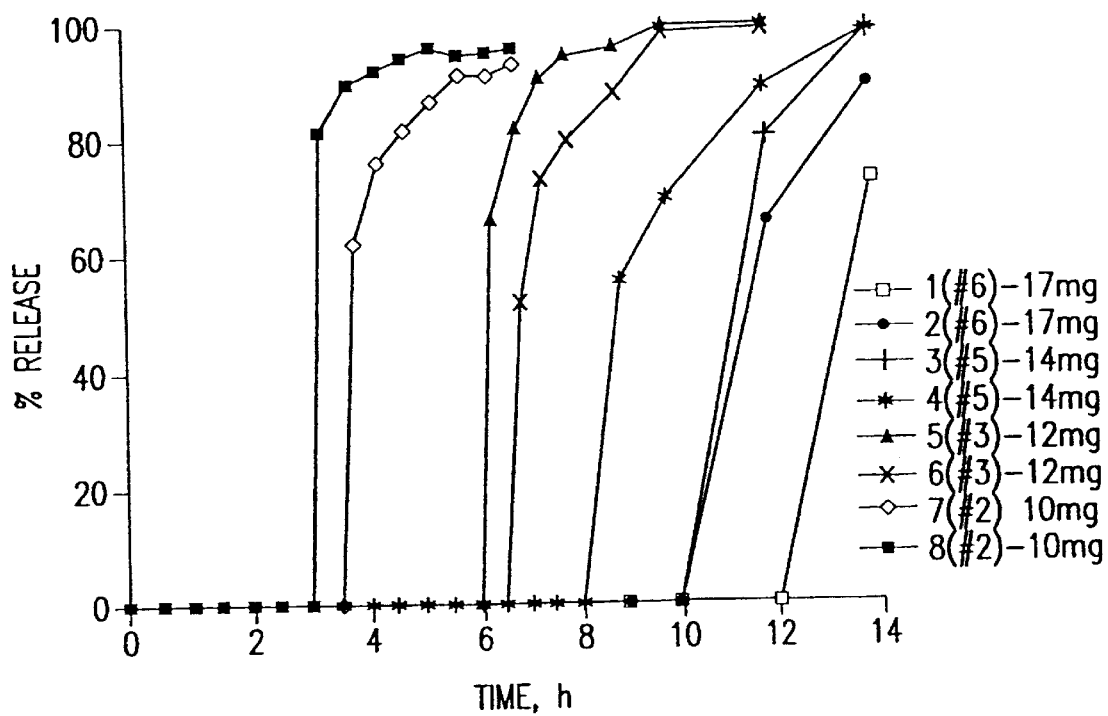
FIG. 8. Diclofenac release from tablets 263-123 (granulated CaP+CPV+EC, granulated diclofenac+CPV+EC; 50% Emcocel®; D=7 mm), coated with ethocel 20/CaP (45% CaP).
Figure 9:
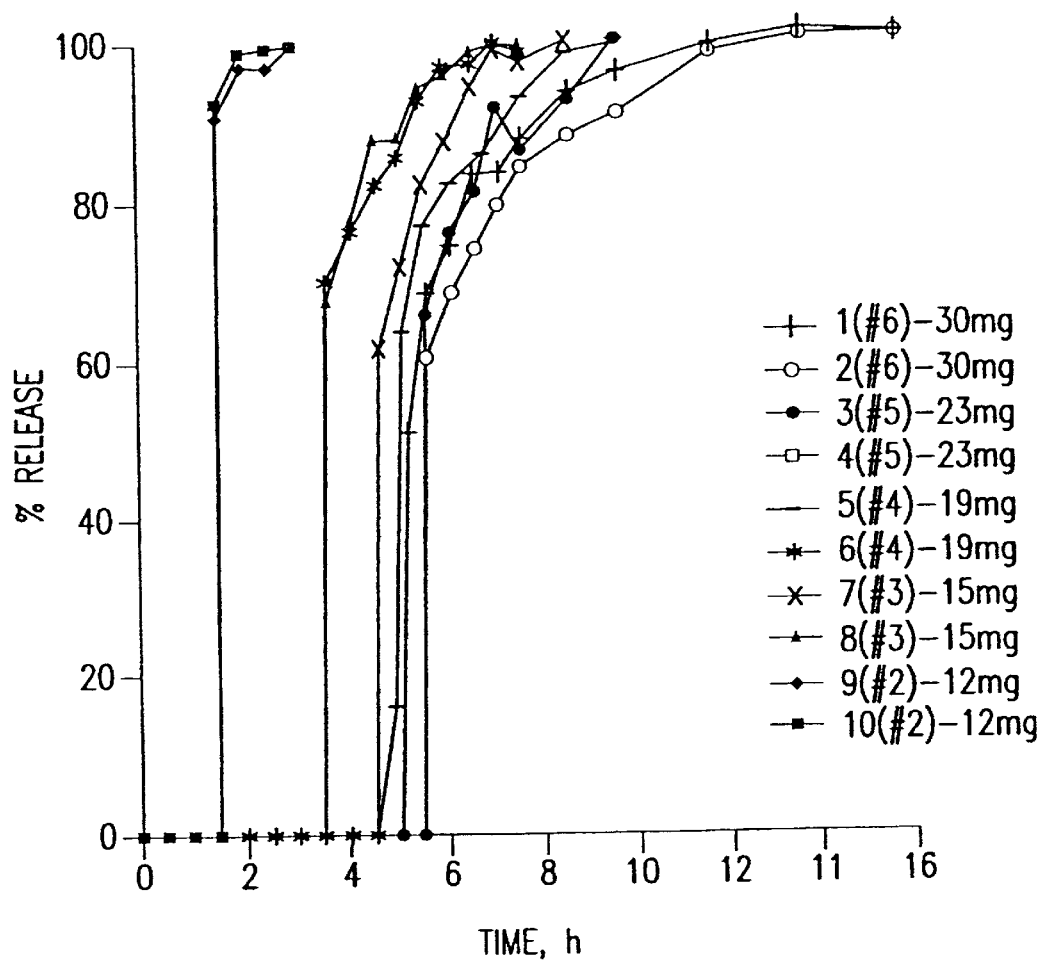
FIG. 9. Diclofenac release from tablets 263-123 (granulated CaP+CPV+EC, granulated diclofenac+CPV+EC; 50% Emcocel®; D=7 mm), coated with ethocel 20/CaP (55% CaP).
Figure 10:
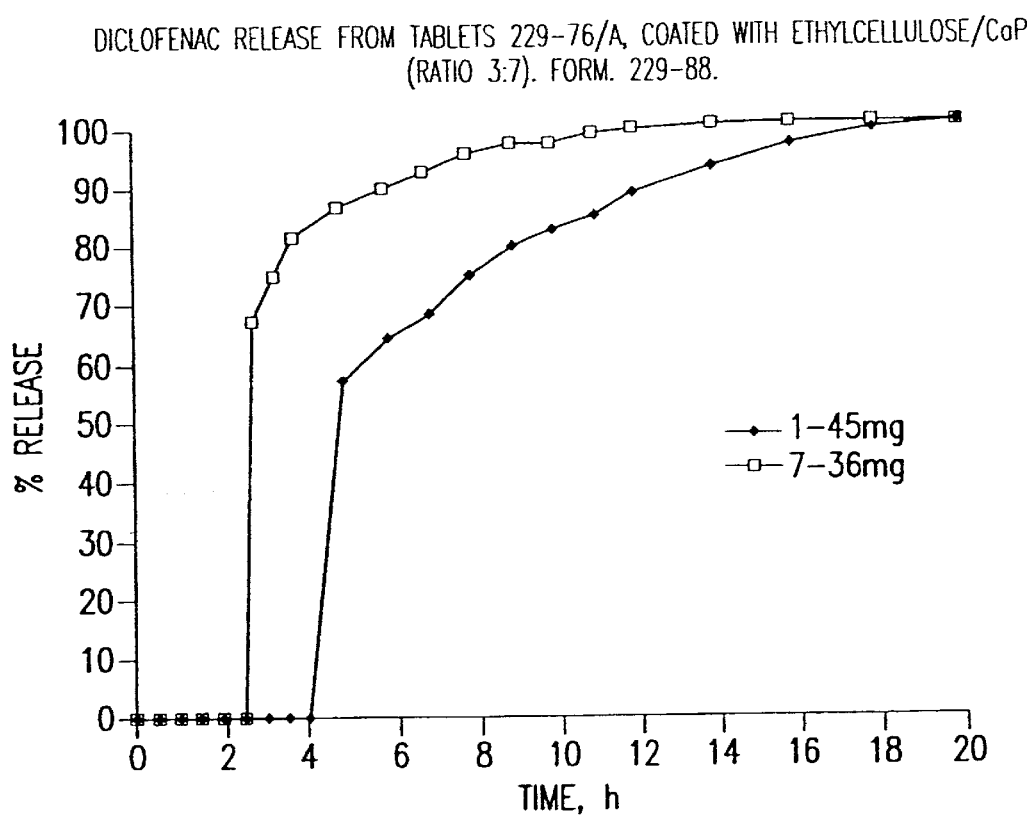
FIG. 10. Diclofenac release from tablets 229-76/A, coated with ethylcellulose/CaP (ratio 3:7).

An alternate method to coating thickness for controlling the time of delay to the burst release of the drug is by controlling the amount of calcium pectinate in the coating. Tablet cores of formulation 263-129 (Table 4) were coated with ethyl cellulose: calcium pectinate, with the content of calcium pectinate varying from 40% to 55%. FIG. 7 shows the results obtained for a coating containing 40% calcium pectinate, FIG. 8 for 45%, FIG. 9 for 50%, and FIG. 10 for 55%. The results show that for each coating type, the length of the delay to burst release of the drug can be controlled by the coating thickness. The results show that for a given coating thickness, there is a shorter delay when there is a higher percentage of calcium pectinate in the coating. Table 5 is a collection of the data for time of delay as a function of the % calcium pectinate.

TABLE 5

Delay of Drug Release as a Function of % CaP in Coating

| coating weight (mg) | % calcium pectinate | delay (hours) |
| --- | --- | --- |
| 12 | 40 | 7 |
| 12 | 45 | 6 |
| 11 | 50 | 3 |
| 12 | 55 | 1.5 |
| 15 | 40 | 10 |
| 14 | 45 | 9 |
| 17 | 50 | 4 |
| 15 | 55 | 3.5 |
| 25 | 50 | 8 |
| 23 | 55 | 5 |

Furthermore, tables of formulation 229-76A (Table 1) were coated with films of calcium pectinate content of 50% and 70%. The results of the delay in drug release for 50% calcium pectinate in the coating is shown in FIG. 1, and for 70% in FIG. 10. With 70% calcium pectinate in the coating one needs a thick coating to be able to obtain a delay of 4 hours.

EXAMPLE 7

Pyridostigmine Bromide Delayed Total Release Tablets (Batch 350-80)

Eudragit® S100, 1.6 grams, was dissolved in 10 ml ethanol. Pyridostigmine bromide, 2.5 grams, was added to the ethanol solution which was stirred until dissolution was complete. Calcium pectinate, 40 grams, was mixed with 2.4 grams of crosspovidone in a mortar and pestle while the ethanolic solution of eudragit® S100 and pyridostigmine bromide was slowly added. After the mixture was well mixed, it was dried at 40° C. for 16 hours and then at 80° C. for 8 hours. The granules were sieved and the fraction <420 $\mu$ was used.

The pyridostigmine-containing granules were mixed with 1.4 grams of silicone dioxide, Aerosil® R972, for 5 minutes to improve their flow properties. The mixture was transferred to a polyethylene bag to which 14 grams crosspovidone and 68.6 grams of microcrystalline cellulose, Emcocel® 90 M, were added. The blend was mixed for 20–30 minutes. Magnesium stearate, 1.24 grams, was added and the blend mixed for another 2–3 minutes. Biconvex 8 mm cores were pressed automatically in a Wick Ges.mbh single punch tablet press. The cores weighed 250 mg and had a hardness of 10 Kp.

Figure 11:
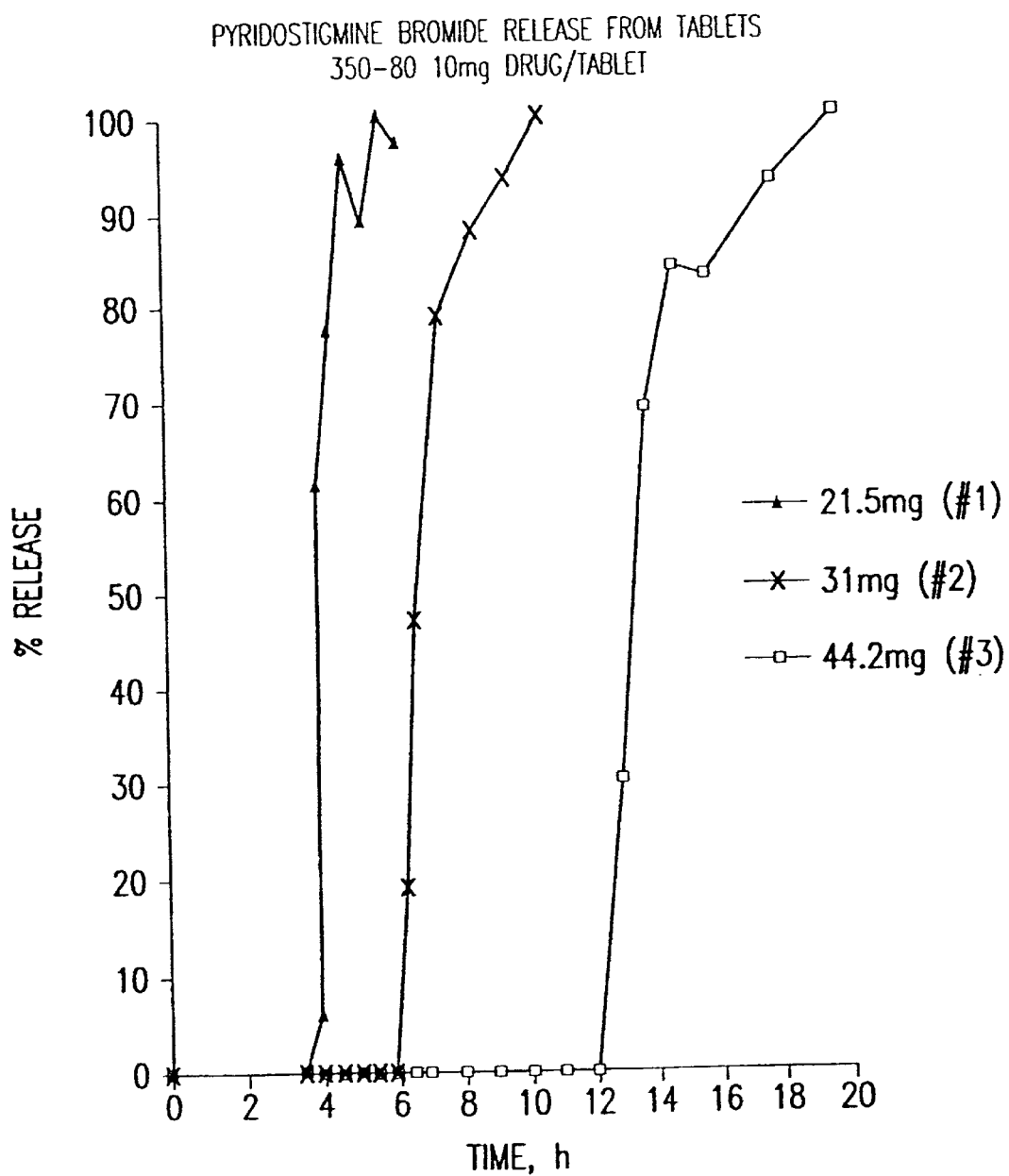
FIG. 11. Pyridostigmine Bromide Release from Tablets 350-80 (10 mg drug/tablet) coated with ethylcellulose/CaP (ratio 1:1).

The cores were coated with ethylcellulose: calcium pectinate 1:1 as described in the previous examples and were tested for their dissolution in intestinal TS solution. The results of the dissolution test are shown in FIG. 11. Tablets coated with 21.5 mg of coating gave a 4 hour delay until the immediate release of the drug content. Tablets coated with 31 mg gave a delay of 6.5 hours to the burst drug release, while those coated with 44.2 mg gave 13 hours to the burst delivery of the drug.

EXAMPLE 8

Pyridostigmine Delayed Total Release Tablets (Water Granulation)

Povidone (Kollidon® 90F) (30 grams) was dissolved in 450 ml water to make the granulation solution. Low methoxy calcium pectinate (1350 grams) and crospovidone (Kollidon® CL) (12 grams) were mixed and then granulated in a high shear granulator, with the granulation solution. Pyridostigmine (150 grams) was added to the wet mass which is then further granulated for several minutes. The wet granulate was dried in a fluidized bed dryer at 60° C. The dry granulate was milled through a 0.5 mm screen.

The pyridostigmine containing granulate (1.1 kg) was mixed with microcrystalline cellulose (Avicel® PH102) (1.18 kg), crospovidone (0.22 kg), and talc (0.04 kg) for fifteen minutes. Magnesium stearate (0.01 kg) was added and the mixture mixed for a few minutes more. Convex round tablets of 8 mm diameter were pressed in a multi-punch automatic tablet press. The tablets weighed 255 mg, had a hardness of 7 Kp and contained 10 mg pyridostigmine bromide each.

The coating suspension was prepared by dissolving 13.65 grams ethyl cellulose in 273 gm ethanol. Calcium pectinate of particle size <150 $\mu$ (13.65 grams) was suspended in the solution. The tablets were coated with this suspension to a weight gain of ~9 mg for each tablet.

These tablets were further coated with a standard enteric coating using methacrylic copolymer type C with ethyl citrate as plasticizer and talc as a glidant.

Figure 12:
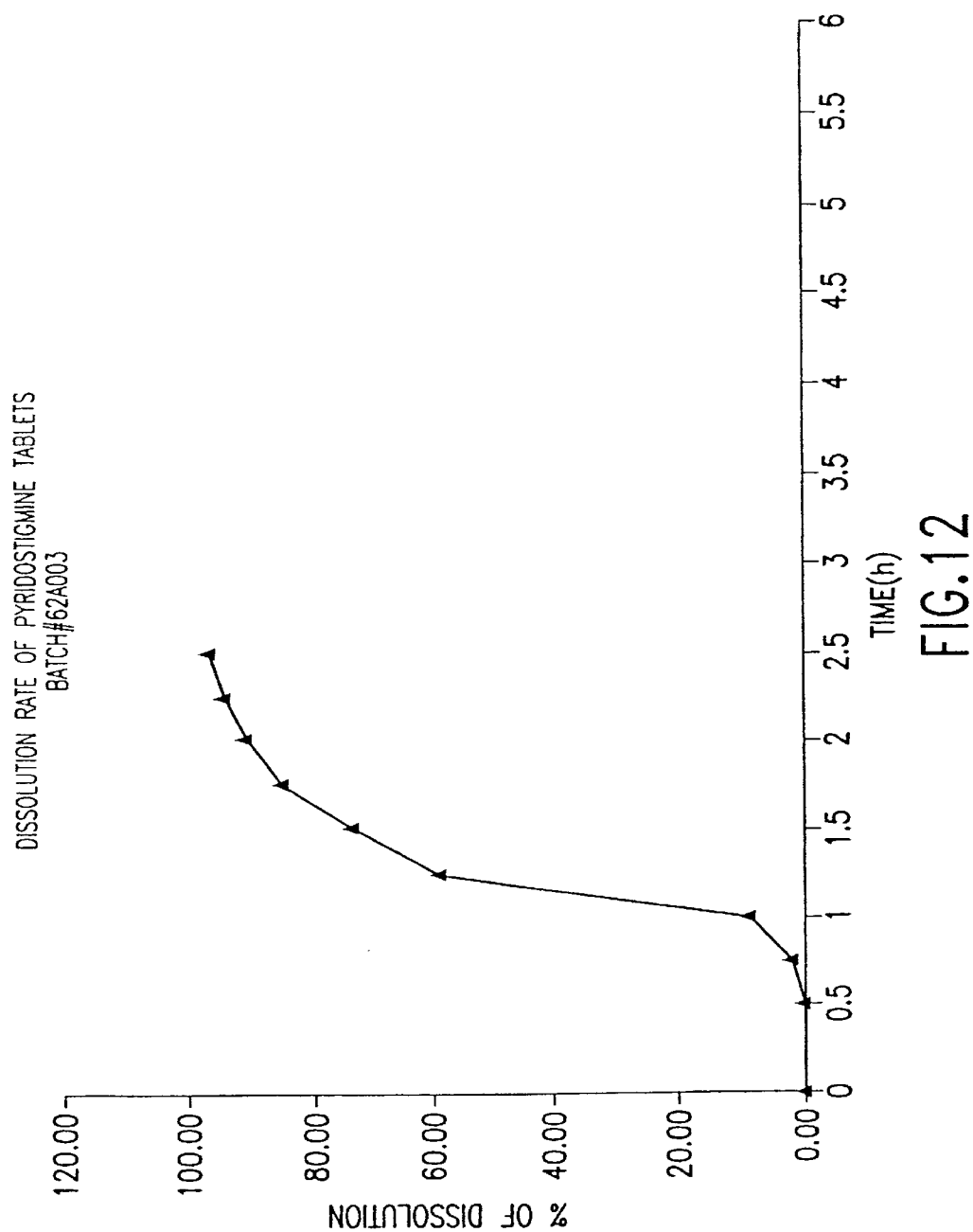
FIG. 12. Pyridostigmine Release from Tablets made with an Aqueous Granulation.

This formulation was tested for its in vitro release pattern by placing it in a USP method 2 dissolution bath containing 900 ml of intestinal TS buffer without enzymes at 37° C. Samples were taken at prearranged times and studied for pyridostigmine bromide content using UV spectrophotometry at 270 nm. The in vitro release of the pyridostigmine tablets produced by the water granulation process is shown in FIG. 12.

EXAMPLE 9

Double Burst Pulse Tablets of Pyridostigmine Bromide

Inner Tablets

Pyridostigmine bromide (3.67 grams), eudragit® S (1.6 grams), crospovidone (2.4 grams) and calcium pectinate (40 grams) were granulated in 10 grams ethanol, dried and sieved as in Example 7. The granules (39 grams) were mixed with silicon dioxide (Aerosil® 200) (1.0 gram), crospovidone (10 grams), microcrystalline cellulose (Emcocel® 90M) (49 grams) and magnesium stearate (1 gram) by the procedure described in example 7. Biconvex cores of 5 mm diameter were pressed automatically in a Wick Ges.mbh single punch press. The cores thus formed weighed 69 mg, had a hardness of 5.3 Kp and contained 3.0 mg pyridostigmine bromide each. These tables were coated at different coating levels to give different delay times.

Coating

The inner tablets were spray coated with ethylcellulose (Ethocel 20):calcium pectinate (<106 $\mu$) (2:3 w/w). Tablets of formulation 376-46/2 were coated with 8 mg of the coating per tablet while tablets of formulation 376-46/4 were coated with 14 mg per tablet.

Outer Tablet Formulation

Pyridostigmine bromide (1.6 grams), eudragit® S (1.3 grams), crospovidone (2.4 grams) and calcium pectinate (40 grams) were granulated in 10 grams ethanol, dried at 35° C. overnight and 80° C. for nine hours. The dried granulate was sieved and the fraction <420 $\mu$ was used. The granules (39 grams) were mixed with silicon dioxide (Aerosil® 200) (1.0 gram) for five minutes, crospovidone (10 grams), and microcrystalline cellulose (Emcocel® 90M) (49 grams) were added and the mixture was mixed for 20–30 minutes. Magnesium stearate (1 gram) was added and the blend was mixed for another 2–3 minutes.

This mixture was pressed on the cores described above. The total diameter in both cases was 9.0 mm. An outer layer of 227 mg was added to 376-46/2 formulations to yield 3.0 mg of pyridostigmine bromide contained in the outer coating to give formulation 376-63 while 220 mg were added to formulation 376-46/4 resulting in 3.0 mg pyridostigmine in the outer coat to give formulation 376-67.

In vitro Release of Drug

Figure 13:
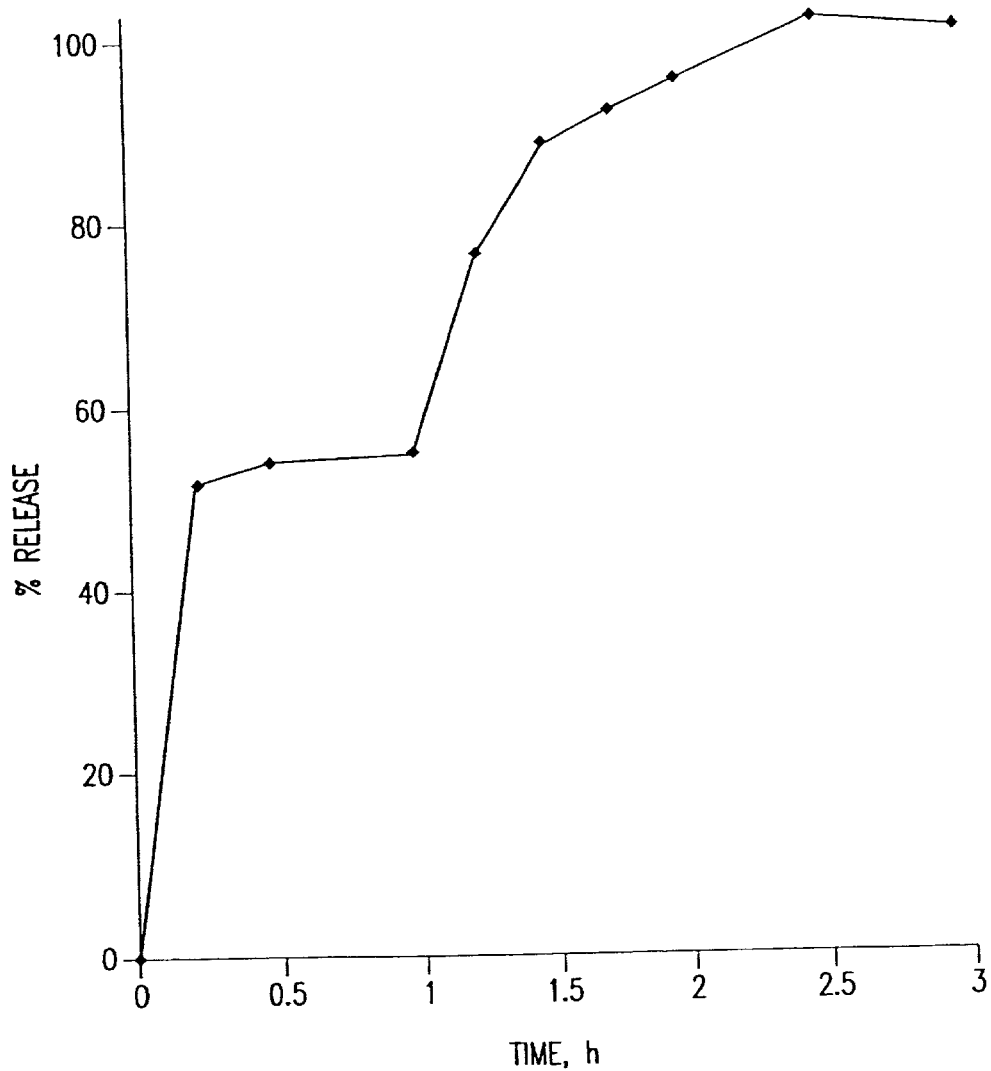
FIG. 13. Pyridostigmine Release from Double Pulse Tablets with Immediate Release of the First Pulse and a One Hour Delay to the Second Pulse.
Figure 14:
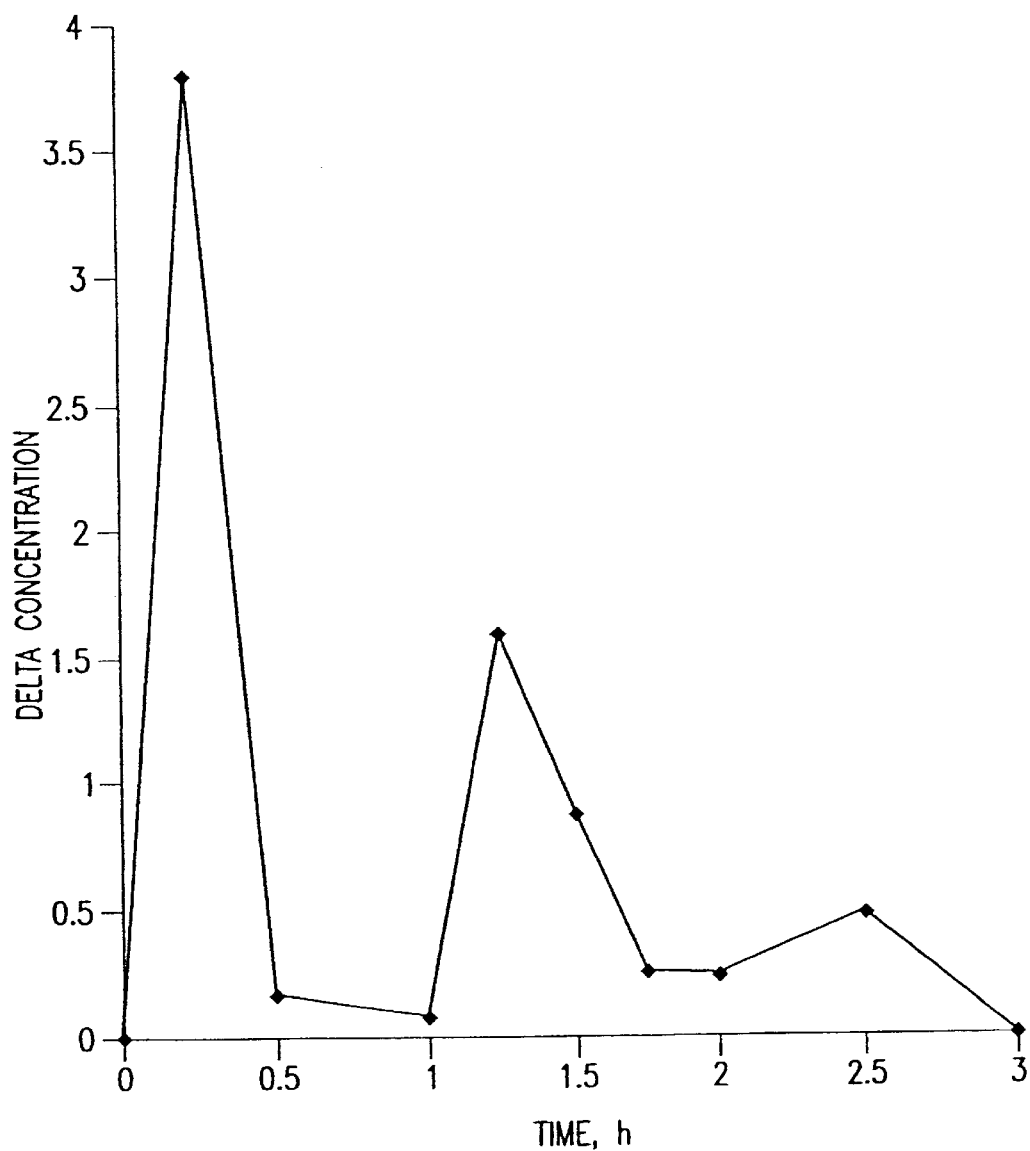
FIG. 14. Differential Concentration of Pyridostigmine from Double Pulse Tablets with Immediate Release of the First Pulse and a One Hour Delay to the Second Pulse.
Figure 15:
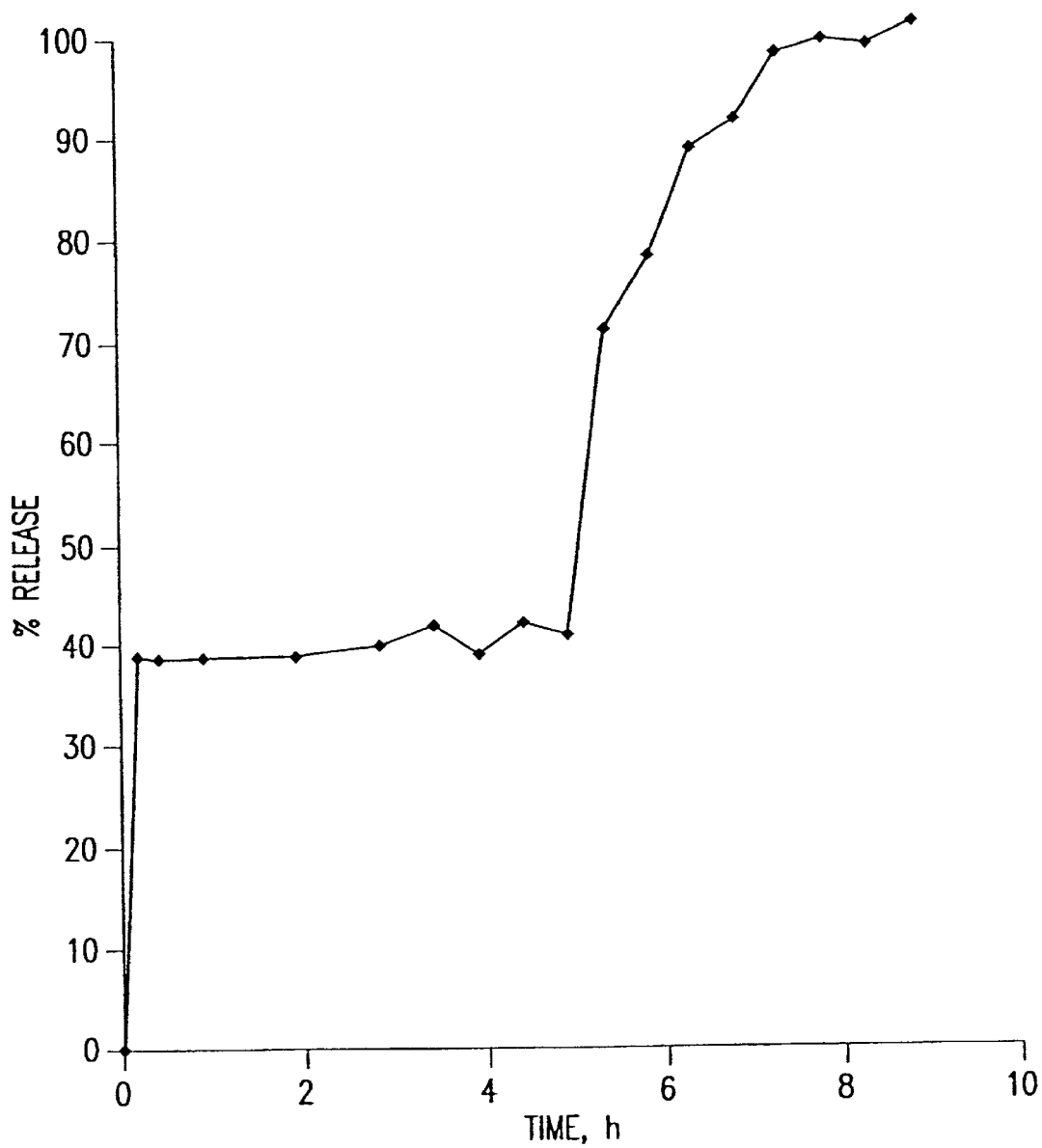
FIG. 15. Pyridostigmine Release from Double Pulse Tablets with Immediate Release of the First Pulse and a Five Hour Delay to the Second Pulse.
Figure 16:
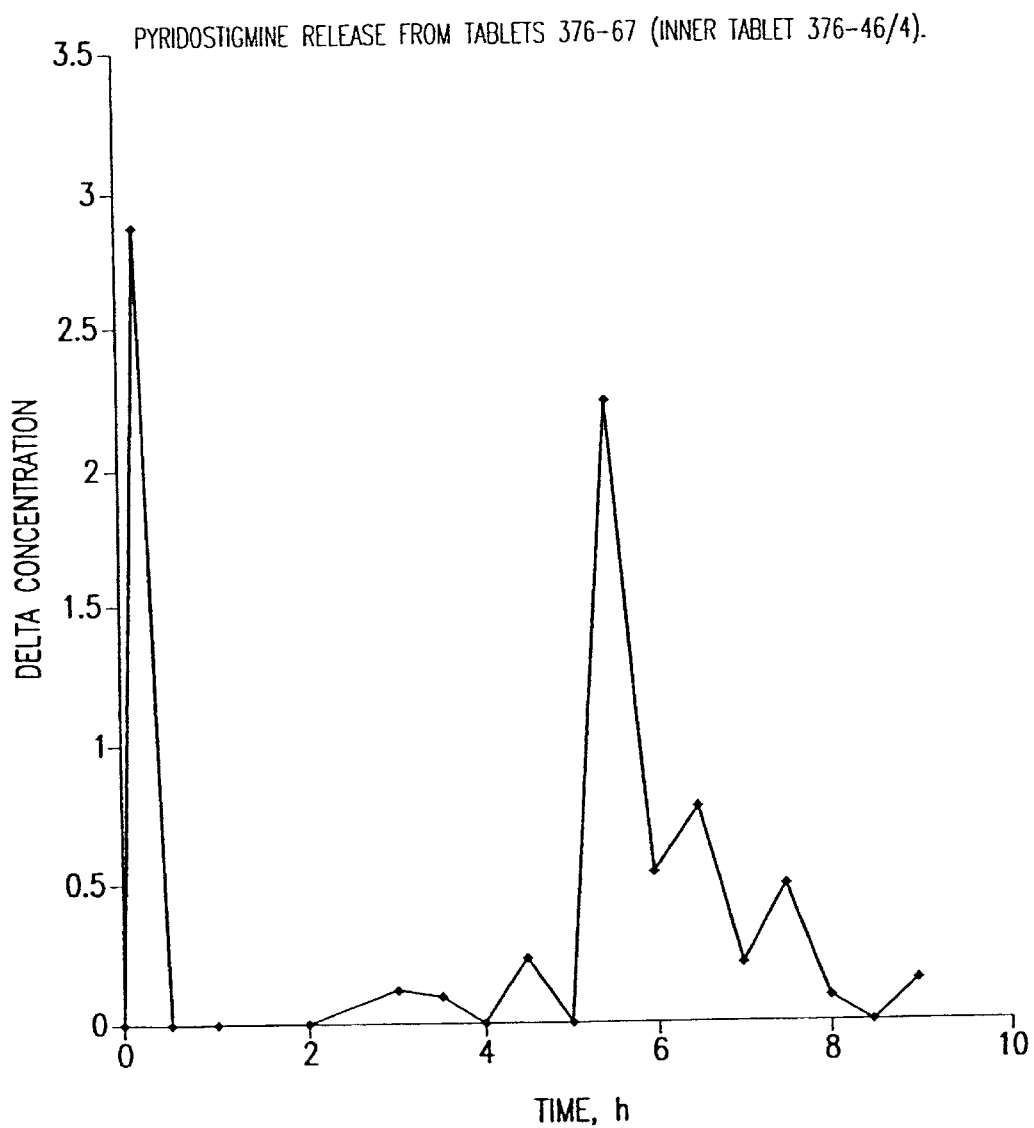
FIG. 16. Differential Concentration of Pyridostigmine from Double Pulse Tablets with Immediate Release of the First Pulse and a Five Hour Delay to the Second Pulse.

Formulations 376-63 and 376-67 were tested for their in vitro release patterns by placing them in a USP method 2 dissolution bath containing 900 ml of intestinal TS buffer without enzymes at 37° C. For formulation 376-63 samples, 3 ml were taken at 0.25, 0.5, 1.0, 1.25, 1.5, 1.75, 2.0, 2.5 and 3 hours while for formulation 376-67, the samples were taken at 0.25, 0.5, 1, 2, 3, 3.5, 4, 4.5, 5, 5.5, 6, 6.5, 7, 7.5, 8, 8.5 and 9 hours. The samples were analyzed by UV spectrophotometry at 270 nm for pyridostigmine bromide content against a standard curve. The results of the average release of pyridostigmine bromide from formulation 376-63 is shown in FIG. 13 with the difference of concentration versus time (to accentuate the pulse nature of the release) plotted in FIG. 14. The corresponding results for formulation 376-67 are given in FIGS. 15–16. One can see that for both formulations, one can obtain the desired two pulse burst release pattern. In both cases, the first pulse was obtained after only several minutes. For formulation 376-63, the delay to the second pulse was one hour while for formulation 376-67, the delay to the second pulse was five hours.

EXAMPLE 10

Double Burst Pulse Tablets of Sodium Diclofenac

Granulate I

Calcium pectinate (60.2 grams), crospovidone (3.6 grams) and ethylcellulose 7 (1.2 grams) were granulated in 20 ml ethanol. The granulate was dried at 35° C. overnight and at 80° C. for 9 hours and sieved through a 420 $\mu$ sieve.

Granulate II

Diclofenac sodium (12.2 grams), crospovidone (0.6 grams), and ethylcellulose 7 (0.2 grams) were granulated in 4 ml ethanol, dried and sieved as for granulate I.

Inner Tablet

Granulate I (32.5 grams) and granulate II (6.3 grams) were mixed in a polyethylene bag. Crospovidone (10.0 grams), and microcrystalline cellulose (Emcocel® 90M) (50.0 grams) were added and mixed well for 20–30 minutes. Magnesium stearate (1.0 gram) was added and the blend mixed for 2–3 minutes more. Biconvex round tablets of 6 mm diameter were pressed automatically in a Wick Ges.mbh single punch press. The cores thus formed weighed 100 mg, had a hardness of 8.4 Kp and contained 5 mg of sodium diclofenac each. These tablets were coated at different coating levels to give different delay times.

Coating

The inner tablets were spray coated with ethylcellulose (Ethocel 20):calcium pectinate (<150 $\mu$) (1:1 w/w). Tablets of formulation 370-140/2 were coated with 6 mg of the coating per tablet while tablets of formulation 370-140/5 were coated with 12 mg per tablet.

Outer Tablet Formation

Granulate I (37.1 grams), granulate II (1.9 grams), crospovidone (10.0 grams), and microcrystalline cellulose (Emcocel® 90M) (50.0 grams) were mixed for 20–30 minutes. Magnesium stearate (1 gram) was added and the blend mixed for a further few minutes. This mixture was pressed on the coated cores described above. The total diameter in both cases was 9.0 mm. An outer layer of 275 mg was added to 370-140/2 formulation with 5 mg of sodium diclofenac contained in the outer coating to give formulation 376-64 while 278 mg were added to formulation 370-140/5 to give 5 mg sodium diclofenac in the outer coat thus producing formulation 376-66.

In vitro Release of Drug

Formulations 376-64 and 376-66 were tested for their in vitro release patterns by placing them in a USP method 2 dissolution bath containing 900 ml of intestinal TS buffer without enzymes at 37° C. For formulation 376-64 samples, 3 ml were taken at 0.25, 0.5, 1.0, 1.25, 1.5, 1.75, 2.0, 2.5 and 3 hours while for formulation 376-66, the samples were taken at 0.25, 0.5, 1, 2, 3, 3.5, 4, 4.5, 5, 5.5, 6, 6.5, 7, 7.5, 8, 8.5 and 9 hours. The samples were analyzed by UV spectrophotometry at 276 nm for sodium diclofenac content against a standard curve.

Figure 17:
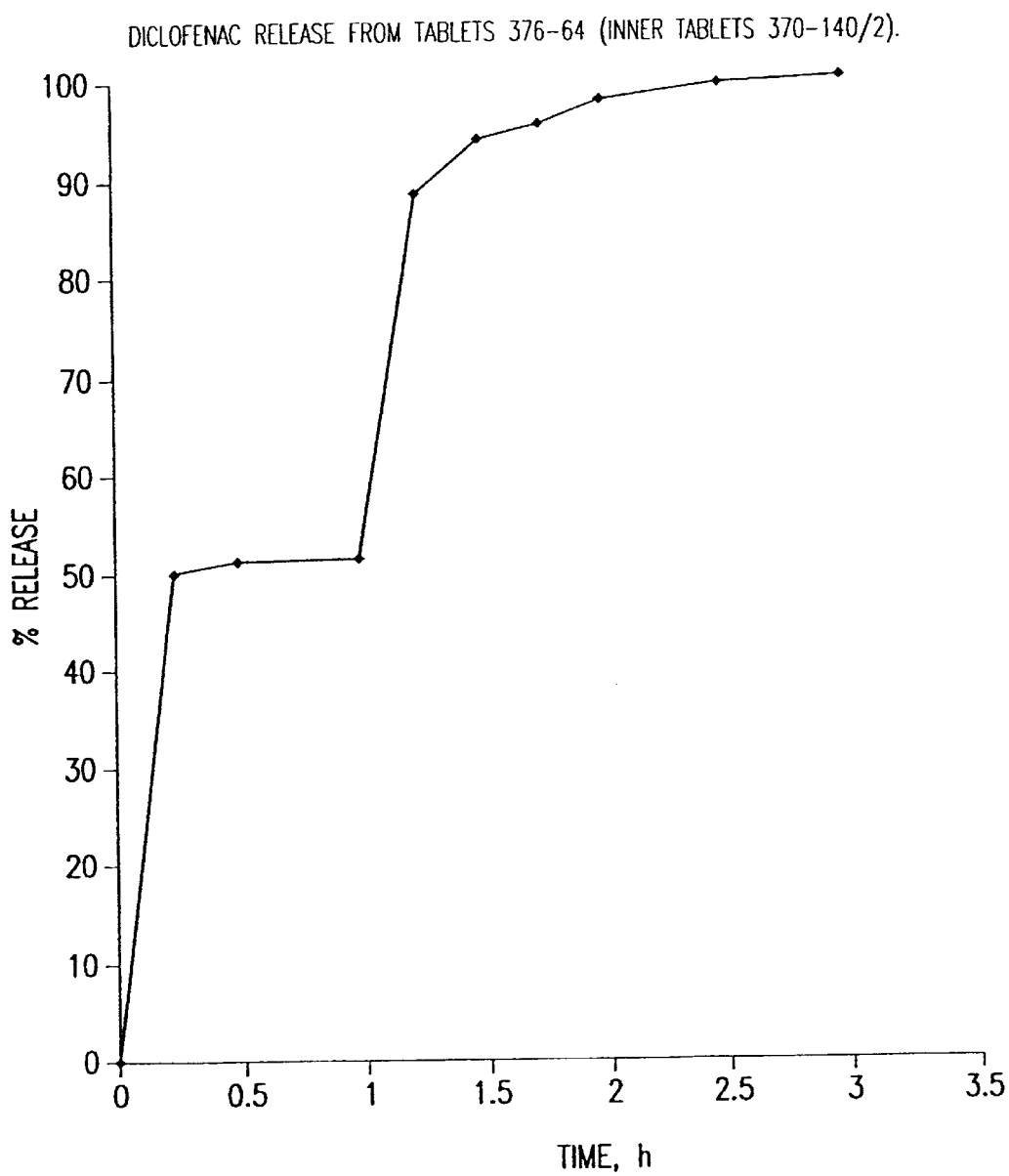
FIG. 17. Sodium Diclofenac Release from Double Pulse Tablets with Immediate Release of the First Pulse and a One Hour Delay to the Second Pulse.
Figure 18:
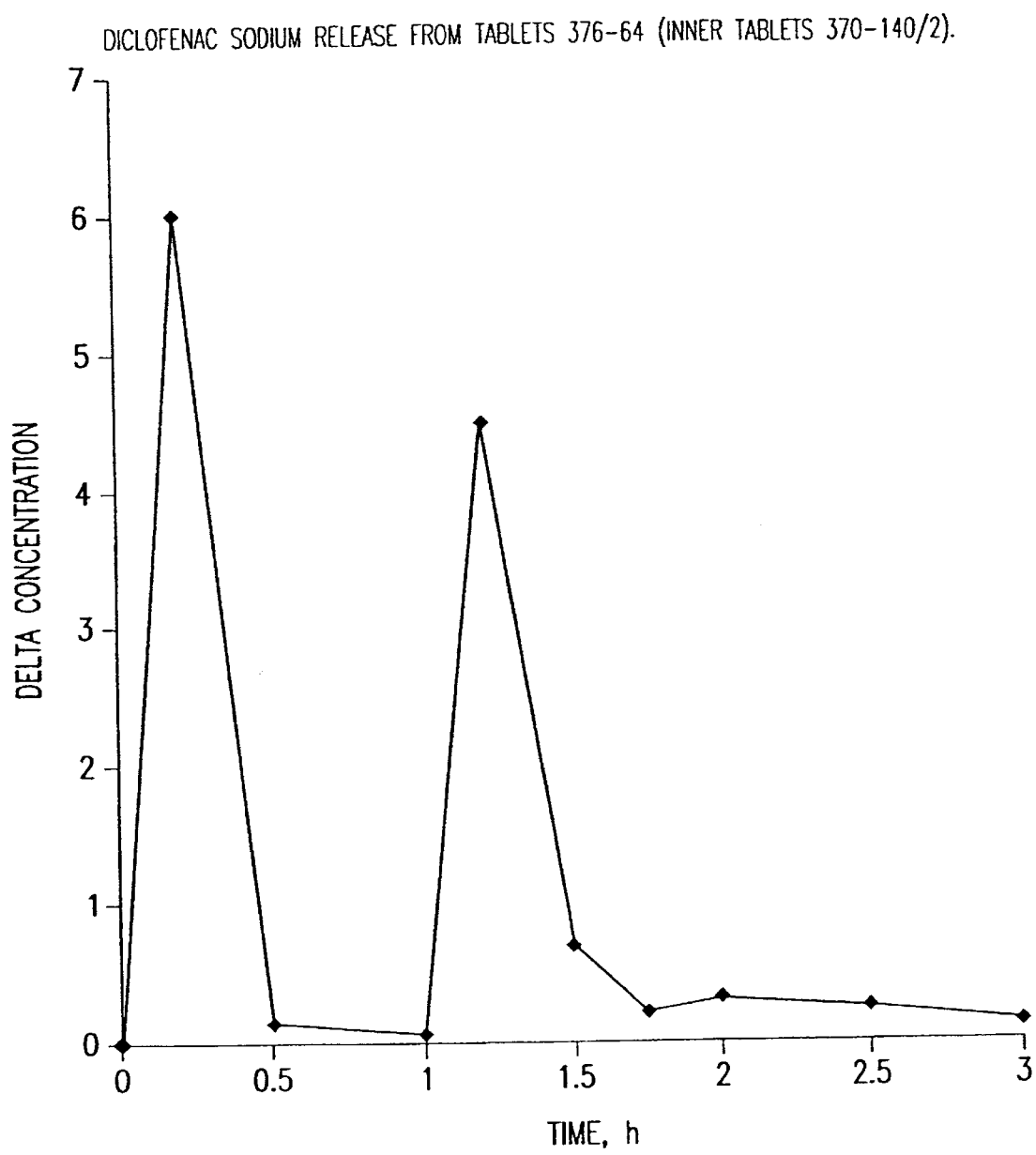
FIG. 18. Differential Concentration of Sodium Diclofenac from Double Pulse Tablets with Immediate Release of the First Pulse and a One Hour Delay to the Second Pulse.
Figure 19:
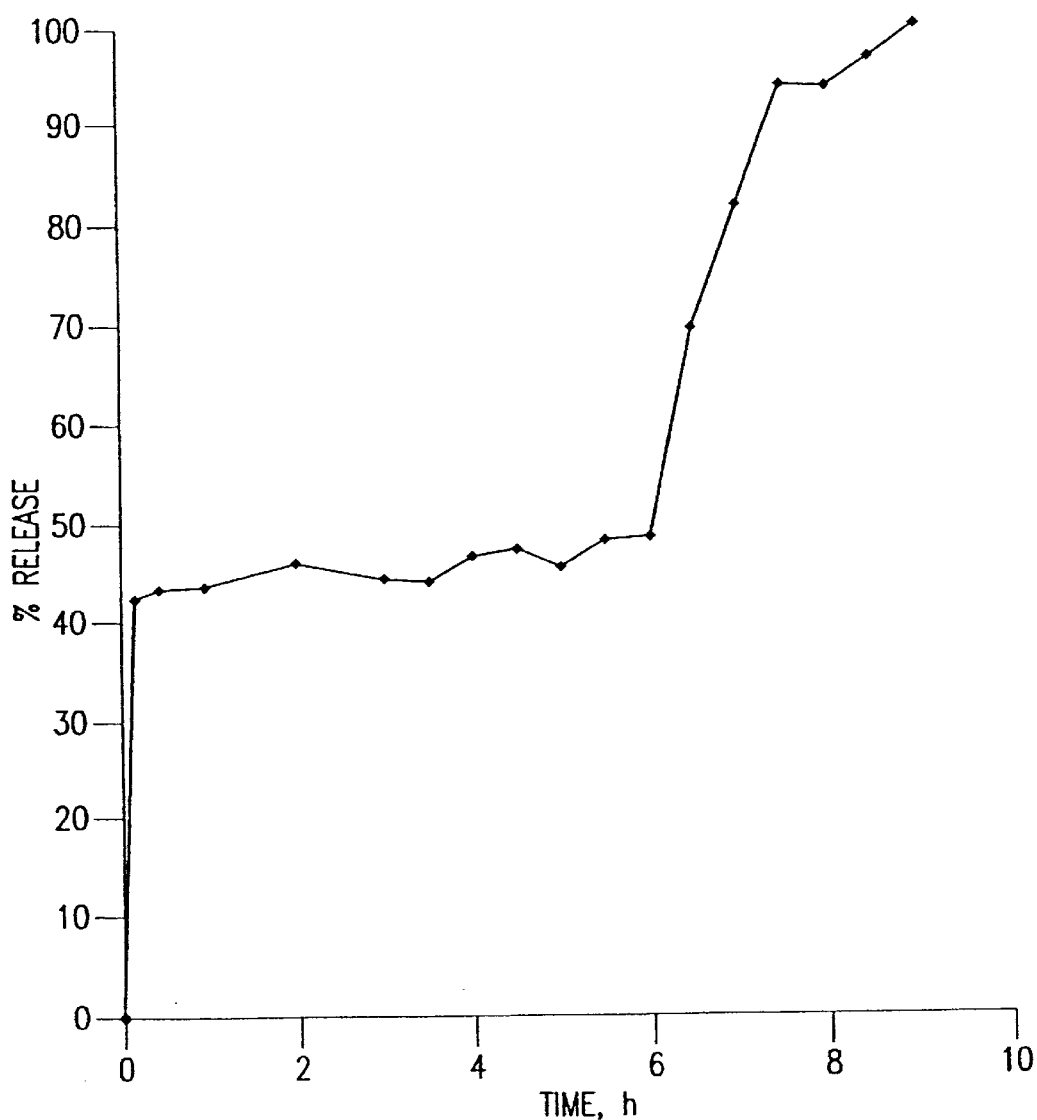
FIG. 19. Sodium Diclofenac Release from Double Pulse Tablets with Immediate Release of the First Pulse and a Six Hour Delay to the Second Pulse.
Figure 20:
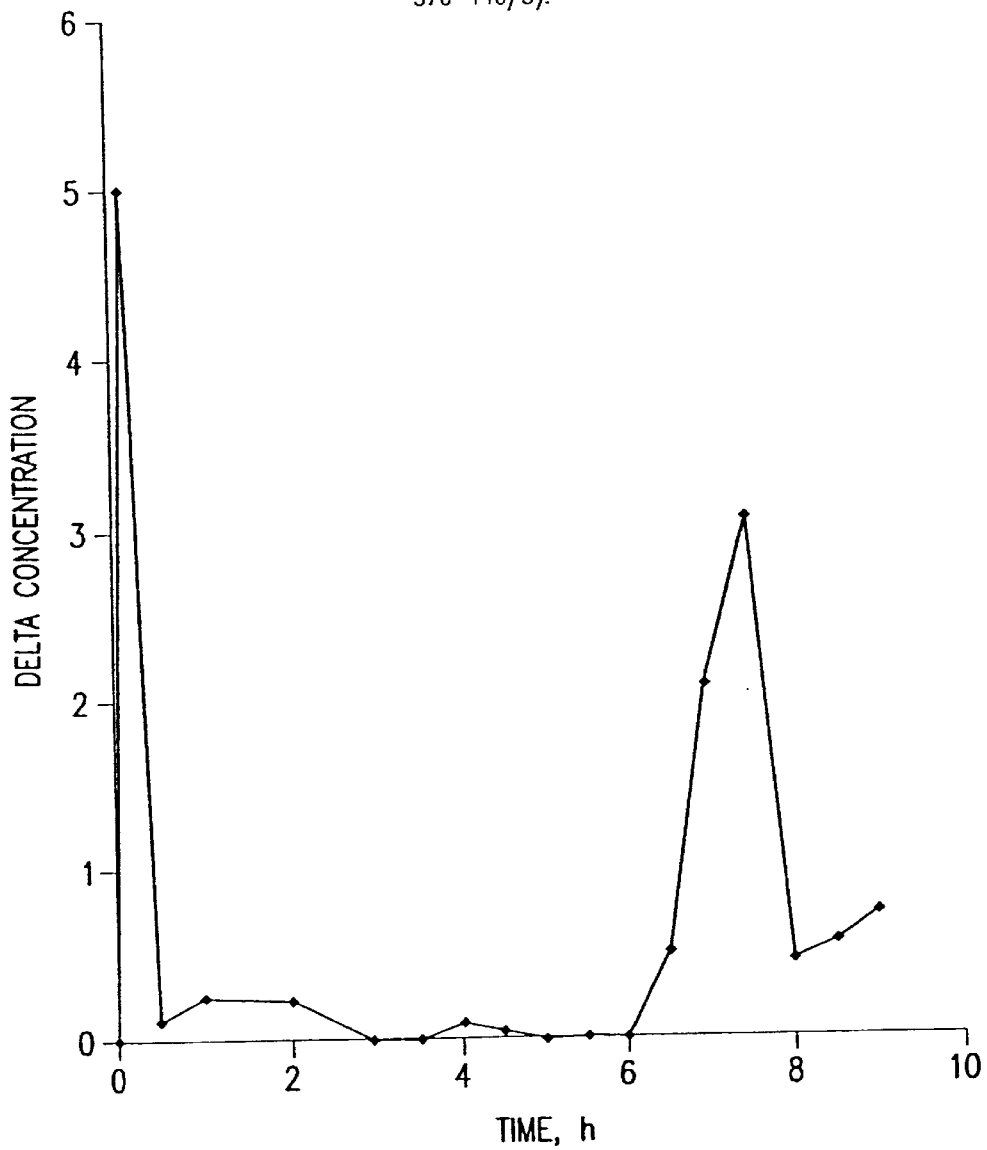
FIG. 20. Differential Concentration of Sodium Diclofenac from Double Pulse Tablets with Immediate Release of the First Pulse and a Six Hour Delay to the Second Pulse.

The results of the average release of sodium diclofenac from formulation 376-64 is shown in FIG. 17 with the difference of concentration versus time (to accentuate the pulse nature of the release) plotted in FIG. 18. The corresponding results for formulation 376-66 are given in FIGS. 19 and 20. One can see that for both formulations, one can obtain the desired two pulse burst release pattern. In both cases the first pulse was obtained after only several minutes. For formulation 376-64 the delay to the second pulse was one hour while for formulation 376-66 the delay to the second pulse was six hours.

EXAMPLE 11

Double Pulse Tablets (Short Sustained Release Followed by Burst Release) of Pyridostigmine Bromide Inner Tablets Pyridostigmine bromide, eudragit® S, and calcium pectinate were granulated in ethanol, dried and sieved as in Example 7. The granules were mixed with silicon dioxide (Aerosil® 200), crospovidone, microcrystalline cellulose and magnesium stearate by the procedure described in Example 7. Biconvex cores of 6 mm diameter (formulation 376-8/2) as well as of 5 mm diameter (formulation 376-41/1) were pressed automatically in a Wick Ges.mbh single punch press. The 6 mm cores thus formed weighed 101.5 mg, had a hardness of 9.5 Kp and contained 3.0 mg pyridostigmine bromide each. The 5 mm cores each weighed 69.4 mg, had a hardness of 6.3 Kp and contained 2.1 mg pyridostigmine bromide.

Coating

Tablets of formulation 376-8/2 were spray coated with ethylcellulose (Ethocel 20): calcium pectinate (<150 $\mu$) as in Example 7, while tablets of formulation 376-46/1 were spray coated with ethycellulose (Ethocel 20):calcium pectinate (<106 $\mu$m) at a ratio of 1:1. Tablets of formulation 376-8/2 were coated with 14 mg of the coating per tablet while tablets of formulation 376-41/1 were coated with 5.4 mg per tablet.

Outer Tablet Formulation

Lactose monohydrate (70 gram) and starch (30 grams), were granulated with a solution of 1 gram povidone K90 and 2.2 grams pyridostigmine bromide in 10 ml water. The granulate was dried in a fluidized bed drier at 70–75° C. and sieved. The fraction <420 $\mu$ was used.

Granulated lactose (49.5 grams), was mixed with 40 grams low methoxy pectin, and 10 grams PVP K90 for 20–30 minutes in a polyethylene bag. Magnesium stearate (0.5 grams) was added and mixed for a further 2 minutes. This mixture was pressed on the coated cores formulation 376-8/2. The total diameter was 9.0 mm. To formulation 376-8/2, with a 6 mm core, 287 mg were added as an outer layer, to produce formulation 376-39A which contains 2.9 mg pyridostigmine bromide in the outer layer.

Granulated lactose (39.5 grams), was mixed with 50 grams low methoxy pectin, and 10 grams PVP K30 for 20–30 minutes in a polyethylene bag. Magnesium stearate (0.5 grams) was added and mixed for a further 2 minutes. This mixture was pressed on the coated cores formulation 376-41/1. The total diameter was 9.0 mm. To formulation 376-41/1, with a 5 mm core, was added 253 mg as an outer layer to produce formulation 376-42A which contains 2.1 mg pyridostigmine bromide in the outer layer.

In vitro Release of Drug

Figure 21:
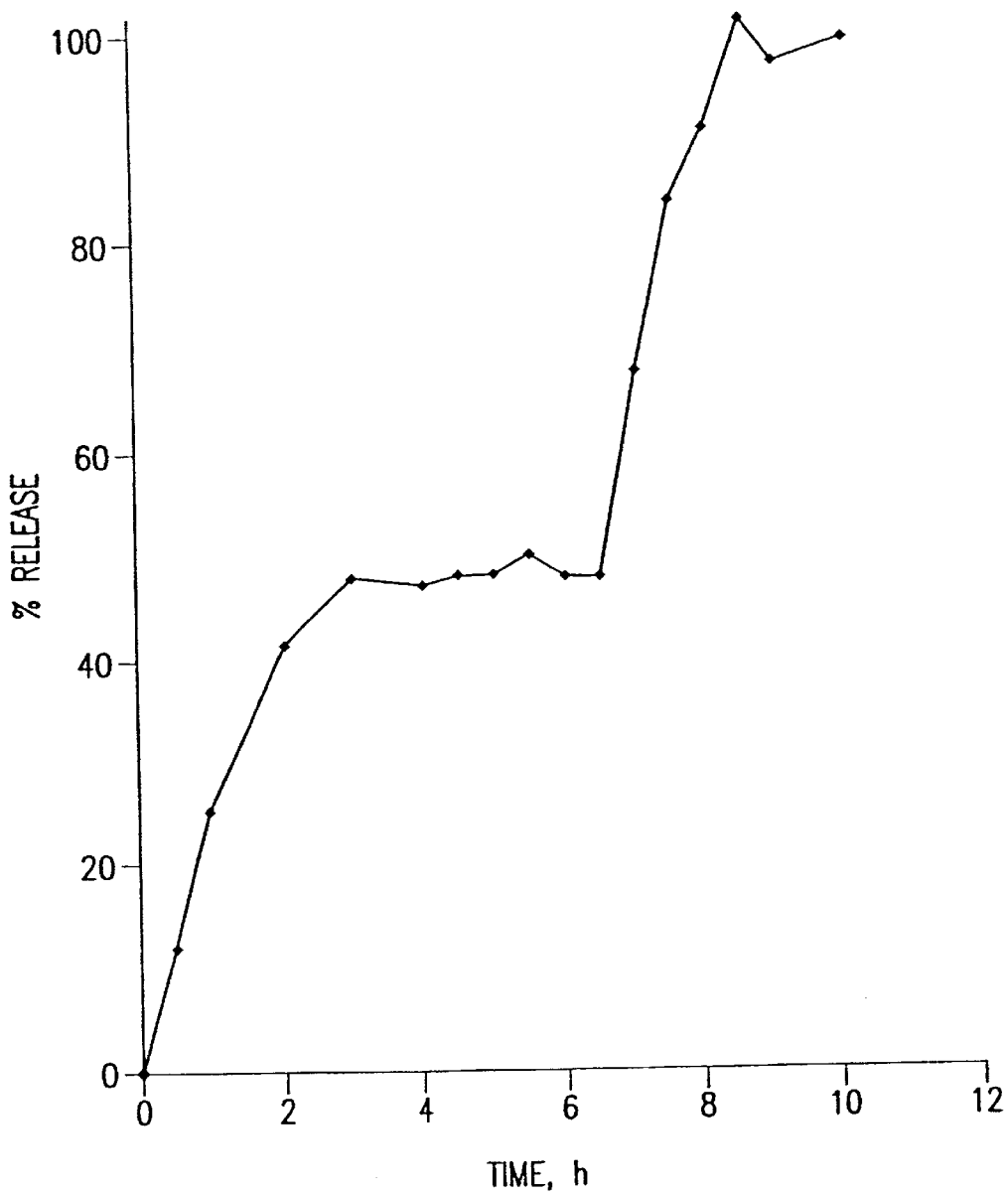
FIG. 21. Pyridostigmine Release from Double Pulse Tablets with a Three Hour Sustained Release for the First Pulse and a Six Hour Delay to the Second Pulse –6 mm Diameter Core.
Figure 22:
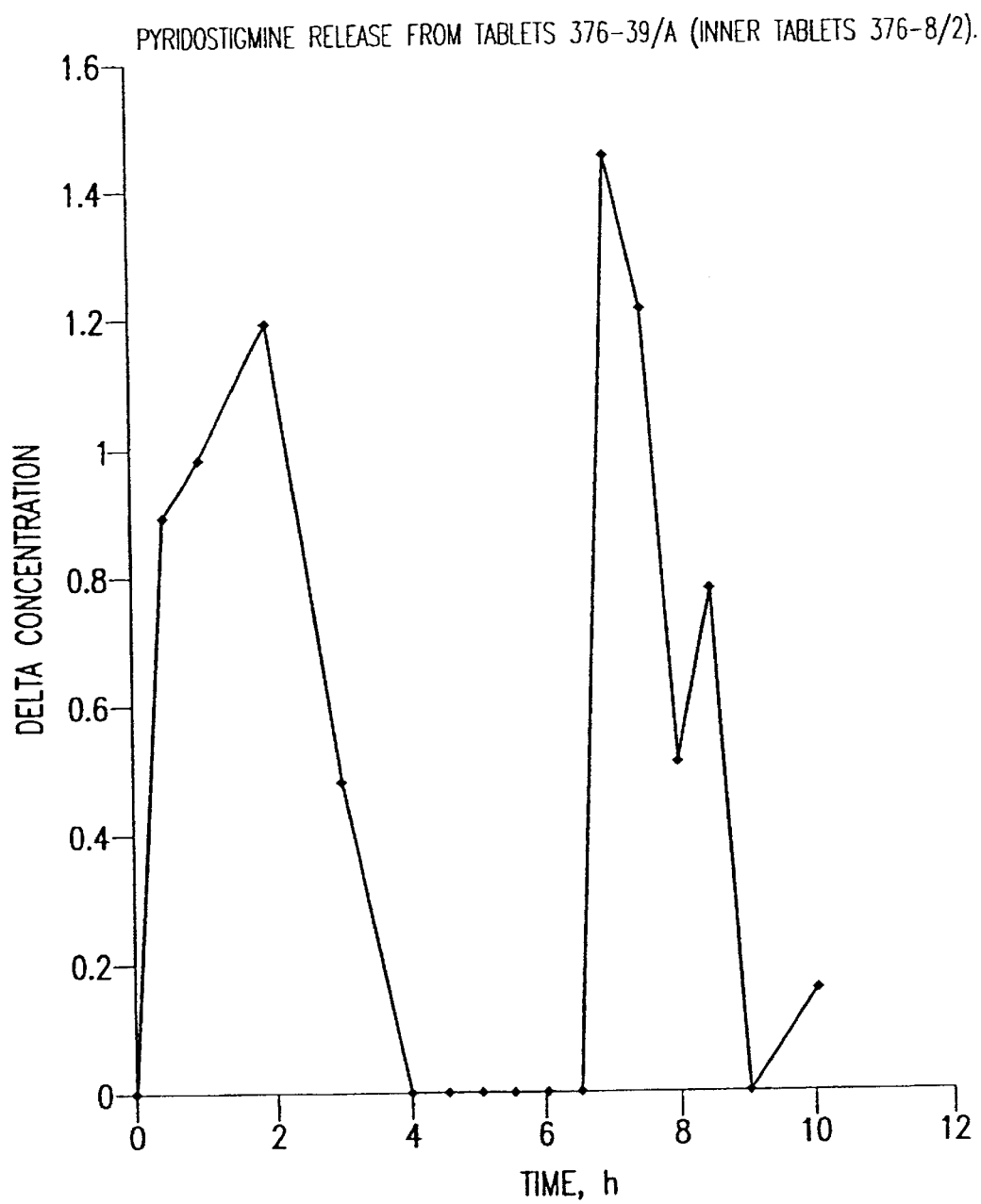
FIG. 22. Differential Concentration of Pyridostigmine from Double Pulse Tablets with a Three Hour Sustained Release for the First Pulse and a Six Hour Delay to the Second Pulse –6 mm Diameter Core.
Figure 23:
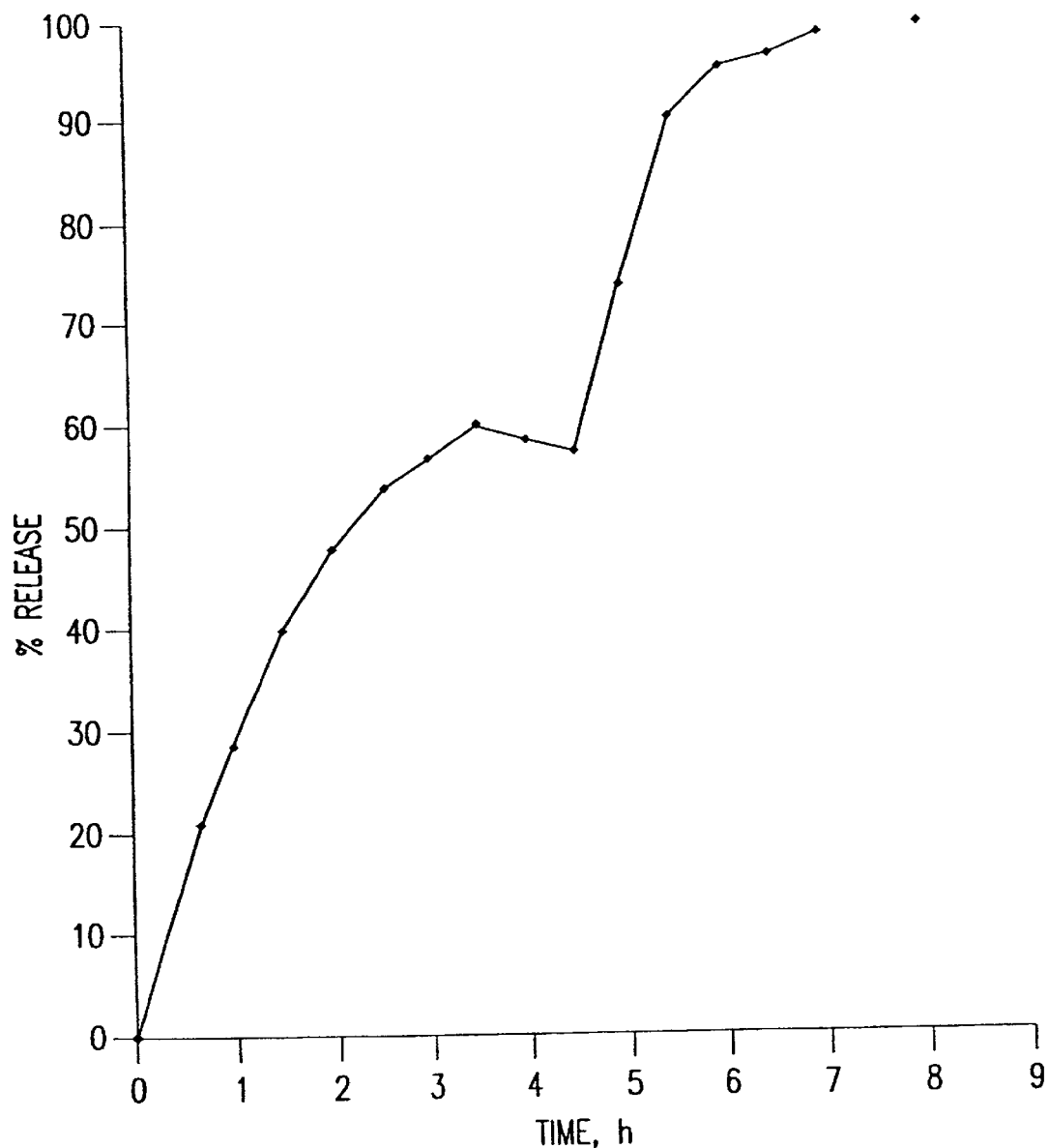
FIG. 23. Pyridostigmine Release from Double Pulse Tablets with a Three Hour Sustained Release for the First Pulse and a Five Hour Delay to the Second Pulse –5 mm Diameter Core.
Figure 24:
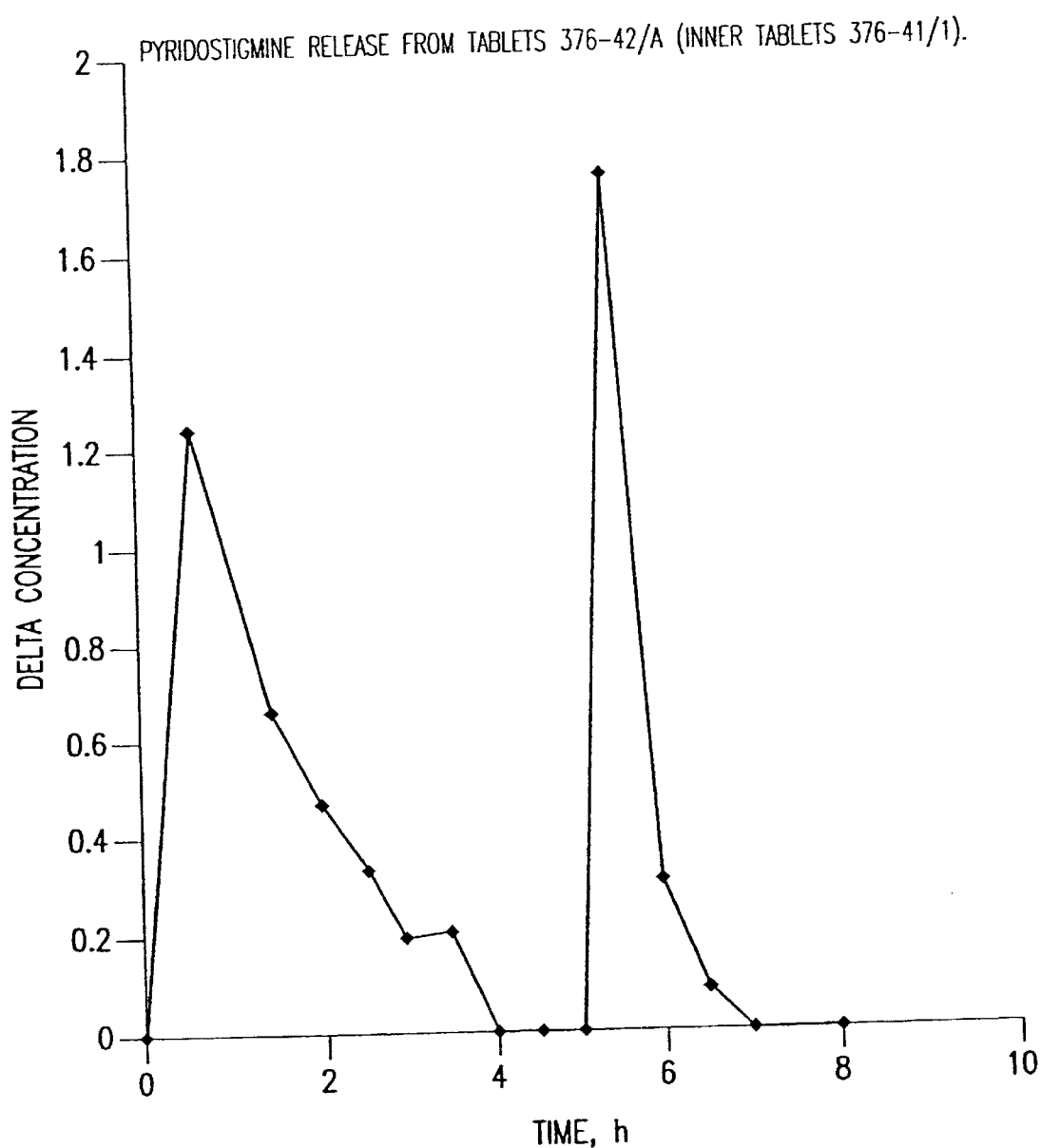
FIG. 24. Differential Concentration of Pyridostigmine from Double Pulse Tablets with a Three Hour Sustained Release for the First Pulse and a Five Hour Delay to the Second Pulse –5 mm Diameter Core.

Formulations 376-39A and 376-42A were tested for their in vitro release patterns by placing them in a USP method 2 dissolution bath containing 900 ml of intestinal TS buffer without enzymes at 37° C. Samples, 3 ml, were taken at 0.5, 1, 2, 3, 3.5, 4, 4.5, 5, 5.5, 6, 6.5, 7, 7.5, 8, 8.5, 9 and 10 hours. The samples were analyzed by UV spectrophotometry at 270 nm for pyridostigmine bromide content against a standard curve. The results of the average release of pyridostigmine bromide from formulation 376-39A is shown in FIG. 21 with the difference of concentration versus time (to accentuate the pulse nature of the release) plotted in FIG. 22. The corresponding results for formulation 376-42A are given in FIGS. 23 and 24. One can see that for both formulations, (i.e. for cores of 6 mm diameter and cores of 5 mm diameter) one can obtain the desired short sustained release pattern of the first pulse over three hours and a burst release of the second pulse after a five to six hour delay.

Discussion of Exemplary Material

Particles of calcium pectinate in a film of ethylcellulose are capable of dramatically altering the properties of the barrier film and give a new dimension to the control of release of soluble drugs from a matrix. A disintegrating tablet is incapable of targeting the delivery of a drug without a proper coating. This coating must prevent diffusion of drug from the tablet and control the intake of liquid into the core so as to control the time and place of tablet disintegration. The core must be capable of breaching the coating at a predetermined time and then disintegrating.

To allow for targeted delivery of soluble drugs a barrier to diffusion is necessary. This barrier must allow for control over the release of the drug to a timed point so that little or no drug is released before desired. The combination of non-water-soluble, but hydrophilic, particles in a hydrophobic coating allows for control of water entry into the tablet and thereby controlled time of disintegration. It has been shown that controlling several parameters (the percent of the particles, the particle size, the film thickness, the identity of the polymer, the identity of the particulate material, and the composition of the core), the time of release of drug from an immediate delivery disintegrating tablet can be controlled. The general trend is as follows:

1. Composition of the core: The more soluble components, whether drug or salts, in the core, the higher the osmotic pressure of the liquid across the membrane, and the faster the liquid crosses through the channels in the membrane into the core.
2. Percent of particles: The higher the percent of hydrophilic, non-soluble particulates embedded in the hydrophobic polymer, the earlier the release of the drug. This is thought to be because more channels are formed through which the liquid can enter the core.
3. Particle size of the particle: The smaller the particle size, the faster the release of drug for a given percent of particles. The smaller particles means that there are numerically more particles for a given weight percentage. The particles also have a larger total surface area so that more interaction among the particles embedded in the film is possible, possibly leading to more channels for liquid entry into the core.
4. Film thickness: The thicker the film, the slower the release of the soluble drug. Thicker films require a longer time for swelling of the hydrophilic insoluble particles across the entire cross section of the hydrophobic barrier film.
5. Identity of the polymer and particulate: The more hydrophobic the polymer, the longer the release time when all other parameters are kept the same. It will take longer for the hydrophilic channels to form when the polymer is more hydrophobic. The more hydrophilic and swellable the particulate, the faster the release when all other parameters are kept the same, since liquid enters the core through the swollen hydrophilic channels causing the core to swell and burst the coating. The more the particulate swells the larger the channels. The more hydrophilic the particulate, the faster the channels form and the more efficient they are at allowing the liquid to diffuse through them.

It is important to have many parameters that allow control of the immediate total release of a drug since each drug—matrix combination is unique and the characteristics of the various sites in the gastrointestinal tract are also unique. The present invention allows one to tailor the design of the film coating to the needs of any system.

The present invention allows one to control the delivery of two pulses of a drug. By using the core and coating described herein to give the controlled timing of the second pulse one can make a two pulse system by overlaying the core and coating with another layer of drug containing material. This layer may be a disintegrating layer, or a sustained released layer and may be a pressed coat layer or a spray coat layer. The first pulse of drug is obtained from the outer layer which is designed according to accepted pharmaceutical practice while the second pulse of the drug is obtained from the coated core of this invention.

Having now fully described the invention, it would be understood by those with skill in the art that the invention may be performed within a wide and equivalent range of conditions, parameters, and the like, without affecting the spirit or scope of the invention or any embodiment therefore. All references cited herein are incorporated herein fully by reference for their relevant teachings.

What is claimed is:

1. A two pulse delivery device for delivering one or more active agents to the gastrointestinal tract of a subject in need of the same, wherein said device comprises:
   a. a core comprising said one or more active agents and a core material that swells in the presence of an aqueous liquid;
   b. an inner coat that surrounds said core, wherein said inner coat has an outer surface and comprises water-insolubic hydrophilic particulate matter embedded in a water-insoluble carrier such that in the presence of an aqueous liquid, said particulate matter forms channels in said inner coat that interconnect said core with said outer surface of said inner coat and wherein said inner coat bursts when said core is swollen, thereby releasing said one or more active agents from said core, wherein said water-insoluble hydrophilic particulate matter and said water-insoluble carrier both include at least one polyssacharide, and wherein said inner coat does not contain an active agent; and
   c. an outer coat that surrounds said outer surface of said inner coat, wherein said outer coat comprises one or more active agents which may be identical to or different from the one or more active agents that are present in said core, said outer coat comprising at least one excipient for controlling release of said one or more active agents and at least one polysaccharide;
wherein release of said one or more active agents from said core and release of said one or more active agents from said outer coat are separated by a predetermined period of time, controlled according to at least a thickness of said inner coat and a relative concentration of said water-insoluble hydrophilic particulate matter of said inner coat.

2. The device of claim 1, wherein said outer coat is further coated with an enteric coating for delaying initiation of release of said one or more agents from said outer coat until the device enters said upper small intestine.

3. The device of claim 1, wherein said polysaccharide of said particulate matter comprises at least one polysaccharide selected from the group consisting of a water-insoluble polysaccharide, a water-insoluble cross-linked polysaccharide, a water-insoluble polysaccharide metal salt and a polysaccharide rendered insoluble by interaction with a poly-cation or poly-anion.

4. The device of claim 1, wherein said core further comprises a disintegrant, and wherein said inner coat is relatively rigid, such that said core disintegrates after said inner coat bursts.

5. The delivery device of claim 4, further comprising a high osmotic gradient across said coating for enhancing uptake of said liquid to said core.

6. The delivery device of claim 4, wherein said core further comprises a hardness enhancer.

7. The delivery device of claim 4, wherein said core material comprises a swellable, non-hydrogel forming water insoluble polymer.

8. The delivery device of claim 4, wherein said relative rigidity of said coating is such that the area under the stress-strain curve of units of energy per area of coating where said coating does not tear is in a range of from about 0.009 to about 0.21 MPa.

9. The delivery device of claim 4, wherein said swellable core material includes at least one derivative of cellulose.

10. The device of claim 9, wherein said at least one derivative of cellulose is selected from the group consisting of cross linked polyvinylpyrrolidone (crospovidone), crosslinked caboxymethylcellulose sodium (cross carmellose), pregelatinized starch, and sodium carboxymethyl starch.

11. The device of claim 1, wherein said swellable core comprises microcrystalline cellulose and a disintegrant.

12. The device of claim 1, wherein said swellable core comprises microcrystalline cellulose and cross linked polyvinylpyrrolidone.

13. The device of claim 12, wherein a ratio of microcrystalline cellulose and cross linked polyvinylpyrrolidone is in a range of from about 1:1 to about 10:1.

14. The device of claim 1, wherein said swellable core comprises microcrystalline cellulose and cross linked carboxymethycellulose sodium.

15. The device of claim 1, wherein said swellable core further comprises an absorption enhancer.

16. The device of claim 1, wherein said water-insoluble hydrophilic particulate matter further comprises an insoluble metal salt of pectin.

17. The device of claim 16, wherein said insoluble metal salt of pectin is selected from the group consisting of calcium pectinate, zinc pectinate, aluminum pectinate, ferric pectinate and ferrous pectinate.

18. A method of delivering an active agent to the gastrointestinal tract of a subject, wherein said method comprises oral administration of a two pulse delivery device for delivery of one or more active agents to said gastrointestinal tract of said animal, said device comprising:
   a. a core comprising said one or more active agents and a core material that swells in the presence of an aqueous liquid;
   b. an inner coat that surrounds said core, wherein said inner core has an outer surface and comprises water-insoluble hydrophilic particulate matter embedded in a water-insoluble carrier such that in the presence of an aqueous liquid, said particulate matter forms channels in said inner coat that interconnect said core with said outer surface of said inner coat and wherein said inner coat bursts when said core is swollen, thereby releasing said one or more active agents from said core, wherein said water-insoluble hydrophilic particulate matter and said water-insoluble carrier both include at least one polysaccharide, and wherein said inner coat does not contain an active agent; and
   c. an outer coat that surrounds said outer surface of said inner coat, wherein said outer coat comprises one or more active agents which may be identical to or different from the one or more active agents that arc present in said core, said outer coat comprising at least one excipient for controlling release of said one or more active agents, wherein said water-insoluble hydrophilic particulate matter and said water-insoluble carrier both include at least one polysaccharide;

wherein release of said one or more active agents from said core and release or said one or more active agents from said outer coat are separated by a predetermined period of time, controlled according to at least a thickness of said inner coat and a relative concentration of said water-insoluble hydrophilic particulate matter of said inner coat.

19. The method of claim 18, wherein said outer coat is further coated with an enteric coating for delaying initiation of release of said one or more agents from said outer coat until said device enters said upper small intestine.

20. The method of claim 18, wherein said polysaccharide of said particulate matter comprises at least one polysaccharide selected from the group consisting of a water-insoluble polysaccharide, a water-insoluble cross-linked polysaccharide, a water-insoluble polysaccharide metal salt and a polysaccharide rendered insoluble by interaction with a poly-cation or poly-anion.

21. The method of claim 18, wherein said core further comprises a disintegrant, and wherein said inner coat is relatively rigid, such that said core disintegrates after said inner coat bursts.

22. The method of claim 19, further comprising a high osmotic gradient across said coating for enhancing uptake of said liquid to said core.

23. The method of claim 19, wherein said core further comprises a hardness enhancer.

24. The method of claim 18, wherein said core material comprises a swellable, non-hydrogel forming water insoluble polymer.

25. The method of claim 18, wherein said relative rigidity of said coating is such that the area under the stress-strain curve of units of energy per area of coating where said coating does not tear is in a range of from about 0.009 to about 0.21 MPa.

26. The method of claim 18, wherein said swellable core material includes at least one derivative of cellulose.

27. The method of claim 26, wherein said at least one derivative of cellulose is selected from the group consisting of cross linked polyvinylpyrrolidone (crospovidone), crosslinked caboxymethylcellulose sodium (cross carmellose), pregelatinized starch, and sodium carboxymethyl starch.

28. The method of claim 18, wherein said swellable core comprises microcrystalline cellulose and a disintegrant.

29. The method of claim 18, wherein said swellable core comprises microcrystalline cellulose and cross linked polyvinylpyrrolidone.

30. The method of claim 29, wherein a ratio of microcrystalline cellulose and cross linked polyvinylpyrrolidone is in a range of from about 1:1 to about 10:1.

31. The method of claim 18, wherein said swellable core comprises microcrystalline cellulose and cross linked carboxymethylcellulose sodium.

32. The method of claim 18, wherein said swellable core further comprises an absorption enhancer.

33. The method of claim 18, wherein said water-insoluble hydrophilic particulate matter further comprises an insoluble metal salt of pectin.

34. The method of claim 18, wherein said insoluble metal salt of pectin is selected from the group consisting of calcium pectinate, zinc pectinate, aluminum pectinate, ferric pectinate and ferrous pectinate.

35. The method of claim 18, wherein said active agent is selected from the group consisting of a non-steroidal anti-inflammatory agent (NSAID), a steroid, a contraceptive, a steroidal hormone, an immunosuppressant, a bronchodilator, an anti-anginal, an anti-hypertensive, an anti-spasmodic agent, an anti-colitis agent, an anti-arrhythmia agent, an anti-neoplastic agent, a protein, a peptide, a hormone, a vaccine, an anti-coagulant, an anti-migraine agent, glibenclamide, a 5-hydroxytryptamine type 1A receptor agonist, a 5HT3 antagonist, metkepyhamid, menthol, an antibiotic, a prostaglandin E1 analog, a prokinetic drug, a cholinergic agonist, a dopamine antagonist, and a reversible inhibitor of acetylcholinesterase.

36. A two pulse delivery device for delivering one or more active agents to the gastrointestinal tract of a subject in need of the same, wherein said device comprises:
   a. a core comprising said one or more active agents and a core material that swells in the presence of an aqueous liquid;
   b. an inner coat that surrounds said core, wherein said inner core does not contain a drug and wherein said inner core has an outer surface and comprises water-insoluble hydrophilic particulate matter embedded in a water-insoluble carrier such that in the presence of an aqueous liquid, said particulate matter forms channels in said inner coat that interconnect said core with said outer surface of said inner coat for controlling the entry of aqueous liquid to said core, and wherein said inner coat bursts when said core is swollen, thereby releasing said one or more active agents from said core, such that said inner coat controls release of said one or more active agents from said core, wherein said water-insoluble hydrophilic particulate matter and said water-insoluble carrier both include at least one polysaccharide, and wherein said inner coat does not contain an active agent; and
   c. an outer coat that surrounds said outer surface of said inner coat, wherein said outer coat comprises one or more active agents which may be identical to or different from the one or more active agents that are present in said core, said outer coat comprising at least one excipient for controlling release or said one or more active agents and at least one polysaccharide, wherein said inner coat physically separates said outer coat from said inner core;

wherein release of said one or more active agents from said core and release of said one or more active agents from said outer coat are separated by a predetermined period of time, controlled according to at least a thickness of said inner coat and a relative concentration of said water-insoluble hydrophilic particulate matter of said inner coat, and such that release of said one or more active agents from said outer coat is controlled separately from said release of said one or more active agents from said core.

* * * * *